(12) United States Patent
Kjellman et al.

(10) Patent No.: US 12,397,044 B2
(45) Date of Patent: *Aug. 26, 2025

(54) METHOD FOR IMPROVING THE BENEFIT TO A SUBJECT OF A THERAPY OR THERAPEUTIC AGENT

(71) Applicant: HANSA BIOPHARMA AB, Lund (SE)

(72) Inventors: Christian Kjellman, Lund (SE); Sofia Jarnum, Lund (SE); Lena Winstedt, Lund (SE)

(73) Assignee: HANSA BIOPHARMA AB, Lund (SE)

( * ) Notice: Subject to any disclaimer, the term of this patent is extended or adjusted under 35 U.S.C. 154(b) by 407 days.

This patent is subject to a terminal disclaimer.

(21) Appl. No.: 17/191,634

(22) Filed: Mar. 3, 2021

(65) Prior Publication Data

US 2021/0260173 A1 Aug. 26, 2021

Related U.S. Application Data

(63) Continuation of application No. 15/328,879, filed as application No. PCT/EP2015/065895 on Jul. 10, 2015, now Pat. No. 10,973,889.

(30) Foreign Application Priority Data

Jul. 25, 2014 (GB) ..................... 1413240

(51) Int. Cl.
| | | |
|---|---|---|
| *A61K 38/48* | (2006.01) | |
| *A61K 35/22* | (2015.01) | |
| *A61K 39/395* | (2006.01) | |
| *C07K 16/00* | (2006.01) | |
| *C12N 9/24* | (2006.01) | |
| *C12N 9/52* | (2006.01) | |

(52) U.S. Cl.
CPC .......... *A61K 38/4873* (2013.01); *A61K 35/22* (2013.01); *A61K 39/395* (2013.01); *C07K 16/00* (2013.01); *C12N 9/2402* (2013.01); *C12N 9/52* (2013.01); *C12Y 302/01096* (2013.01); *C07K 2317/21* (2013.01); *C07K 2317/52* (2013.01); *C07K 2317/54* (2013.01); *Y02P 20/582* (2015.11)

(58) Field of Classification Search
None
See application file for complete search history.

(56) References Cited

U.S. PATENT DOCUMENTS

| | | | | |
|---|---|---|---|---|
| 8,133,483 B2 * | 3/2012 | Bjorck | ............... | A61K 19/02 424/800 |
| 8,323,908 B2 * | 12/2012 | Allhorn | ............... | G01N 33/6857 435/7.1 |
| 9,493,752 B2 * | 11/2016 | Collin | ............... | C12N 9/2402 |
| 10,696,959 B2 * | 6/2020 | Kjellman | ............... | A61P 37/06 |
| 10,758,597 B2 * | 9/2020 | Kjellman | ............... | A61P 43/00 |
| 10,973,889 B2 * | 4/2021 | Kjellman | ............... | C07K 16/00 |
| 11,214,784 B2 * | 1/2022 | Kjellman | ............... | A61K 38/48 |
| 11,524,057 B2 * | 12/2022 | Kjellman | ............... | A61K 38/48 |
| 11,667,905 B2 * | 6/2023 | Kjellman | ............... | A61P 25/00 435/220 |
| 2004/0247579 A1 | 12/2004 | Sykes | | |
| 2023/0181701 A1 * | 6/2023 | Kjellman | ............... | A61P 37/00 424/93.21 |

FOREIGN PATENT DOCUMENTS

| | | |
|---|---|---|
| WO | 2006/131347 A2 | 12/2006 |
| WO | 2008/071418 | 6/2008 |
| WO | 2009/033670 | 3/2009 |
| WO | 2013/037824 | 3/2013 |
| WO | 2013/110946 | 8/2013 |

OTHER PUBLICATIONS

"Pulmonology" edited by A.G. Chuchalina, Moscow, GEOTAR-Media, 2009, pp. 938-939.
Abu Jawdeh BG et al. "Desensitization in kidney transplantation: review and future perspectives." Clin Transplant. Apr. 2014; 28(4):494-507.
Agniswamy J et al. "Insight of host immune evasion mediated by two variants of group a Streptococcus Mac protein." J Biol Chem. Dec. 10, 2004; 279(50):52789-96.
Akesson P et al. "Low antibody levels against cell wall-attached proteins of Streptococcus pyogenes predispose for severe invasive disease." J Infect Dis. Mar. 1, 2004; 189(5):797-804.
Akesson P et al. "IdeS, a highly specific immunoglobulin G (IgG)-cleaving enzyme from Streptococcus pyogenes, is inhibited by specific IgG antibodies generated during infection" Infect Immun. Jan. 2006;74(1):497-503.
Albert H et al. "In vivo enzymatic modulation of IgG glycosylation inhibits autoimmune disease in an IgG subclass-dependent manner." Proc Natl Acad Sci U S A. Sep. 30, 2008; 105(39):15005-9.
Allhorn, Maria et al., "Human IgG/FcγR Interactions Are Modulated by Streptococcal IgG Glycan Hydrolysis," PLoS One. 2008; 3(1): e1413, 21 pages.

(Continued)

*Primary Examiner* — Phuong Huynh
(74) *Attorney, Agent, or Firm* — Norton Rose Fulbright US LLP

(57) ABSTRACT

The invention relates to a method for improving the benefit of a therapy or a therapeutic agent to a subject. The method comprises administering to the subject an agent which reduces Fc receptor binding of serum IgG molecules in the subject; and subsequently administering said therapy or said therapeutic agent to the subject. The invention also relates to a method for reducing the effect of pathogenic autoantibodies in a subject, the method comprising (a) administering to the subject an agent which reduces Fc receptor binding of serum IgG molecules in the subject and optionally (b) subsequently subjecting the subject to a treatment which removes endogenous autoantibodies. The invention also relates to a kit for carrying out a method of the invention.

11 Claims, 39 Drawing Sheets

Specification includes a Sequence Listing.

(56) References Cited

OTHER PUBLICATIONS

Anonymous: "Structural Biochemistry/proteins/Enzyme-Linked Immunoabsorbent Assay (ELISA)—Wikibooks, open books for an open world." Oct. 29, 2012 (Oct. 29, 2012) [retrieved Feb. 29, 2016] https://en.wikibooks.org/wiki/Structural_Biochemistry/Proteins/Enzyme-Linked_Immunoabsorbent_Assay_(ELISA), 4 pages.
Baruah K et al. "Selective deactivation of serum IgG: a general strategy for the enhancement of monoclonal antibody receptor interactions." J Mol Biol. Jun. 29, 2012; 420(1-2):1-7.
Brezski RJ et al. "Tumor-associated and microbial proteases compromise host IgG effector functions by a single cleavage proximal to the hinge." Proc Natl Acad Sci U S A. Oct. 20, 2009; 106(42):17864-9.
Chica et al., Curr Opin Biotechnol. 16(4):378-84 (Year: 2005).
Chinese Office Action dated May 27, 2020 in Chinese Patent Application No. 201580049441.3, 34 pages.
Cornell LD et al. "Positive crossmatch kidney transplant recipients treated with eculizumab: outcomes beyond 1 year." Am J Transplant. May 2015; 15(5):1293-302.
Ge, Baolin et al., eds. "Immunosuppressive measures for rejection" Practical Pathophysiology, 1995, pp. 270-274.
Getts, Daniel R et al., "Current landscape for T-cell targeting in autoimmunity and transplantation," Immunotherapy, vol. 3, No. 7, Jul. 1, 2011 (Jul. 1, 2011) pp. 853-870.
Hardy I et al. "Anti-CD79 Antibody Induces B Cell Anergy That Protects against Autoimmunity." J Immunol. Feb. 15, 2014; 192(4):1641-50.
Hirose M et al. "Enzymatic autoantibody glycan hydrolysis alleviates autoimmunity against type VII collagen." J Autoimmun. Dec. 2012; 39(4):304-14.
International Search Report for corresponding international application PCTEP2015065895, mailed Mar. 1, 2016, 8 pages.
Ismail N et al. "Plasmapheresis." 3rd edn. J.T. Daugirdas, P.G. Blake, and T.S. Ing, editors. Lippincott Williams Wilkins, Philadelphia. Handbook of dialysis 2001 231-262.
Iyer HS et al. "Transplanting the highly sensitized patient: trials and tribulations." Curr Opin Nephrol Hypertens. Nov. 2013;22(6):681-8.
Jahnmatz M et al. "Optimization of a human IgG B-cell ELISpot assay for the analysis of vaccine-induced B-cell responses." J Immunol Methods. May 31, 2013; 391(1-2):50-9.
Johansson BP et al. "IdeS: a bacterial proteolytic enzyme with therapeutic potential." PLoS One. Feb. 27, 2008; 3(2):e1692.
Johansson Soderberg J "The streptococcal IgG degrading enzyme IdeS: studies on host-pathogen interactions", 2012 Umeå University medical dissertations. ISSN 0346-6612; 1491.
Jordan SC et al. "Evaluation of intravenous immunoglobulin as an agent to lower allosensitization and improve transplantation in highly sensitized adult patients with end-stage renal disease: report of the NIH IG02 trial." J Am Soc Nephrol. Dec. 2004;15(12):3256-62.
Jordan SC et al. "Intravenous immune globulin treatment inhibits crossmatch positivity and allows for successful 10 transplantation of incompatible organs in living-donor and cadaver recipients." Transplantation. Aug. 27, 2003; 76(4):631-6.
Liu, Gentao et al., eds., "Structure and function of antibodies" Current Pharmacology, 2008, p. 740.
Macklin PS et al. "A systematic review of the use of rituximab for desensitization in renal transplantation." Transplantation. Oct. 27, 2014; 98(8):794-805.
Moll S et al. "Humoral rejection of organ allografts." Am J Transplant. Nov. 2005; 5(11):2611-8.
Montgomery RA et al. "Consensus opinion from the antibody working group on the diagnosis, reporting, and risk assessment for antibody-mediated rejection and desensitization protocols." Transplantation. Jul. 27, 2004; 78(2):181-5.

Montgomery RA et al. "Desensitization in HLA-incompatible kidney recipients and survival", N Engl J Med. Jul. 28, 2011; 365(4):318-26.
Montgomery RA et al. "HLA incompatible renal transplantation." Curr Opin Organ Transplant. Aug. 2012;17(4):386-92.
Montgomery RA et al. "Plasmapheresis and intravenous immune globulin provides effective rescue therapy for refractory humoral rejection and allows kidneys to be successfully transplanted into cross-match-positive recipients." Transplantation. Sep. 27, 2000; 70(6):887-95.
Nandakumar KS et al. "Blocking of experimental arthritis by cleavage of IgG antibodies in vivo." Arthritis Rheum. Oct. 2007;56(10):3253-60.
Pierson RN 3rd "Antibody-mediated xenograft injury: mechanisms and protective strategies." Transpl Immunol. Jun. 2009;21(2):65-9.
Ryan MH et al. "Proteolysis of purified IgGs by human and bacterial enzymes in vitro and the detection of specific proteolytic fragments of endogenous IgG in rheumatoid synovial fluid." Mol Immunol. Apr. 2008;45(7):1837-46.
Singh et al., Curr Protein Pept Sci. 18: 1-11 (Year: 2017).
Su YF et al. "The deficient cleavage of M protein-bound IgG by IdeS: insight into the escape of *Streptococcus pyogenes* from antibody-mediated immunity." Mol Immunol. Oct. 2011;49(1-2):134-42.
Sun, Jiangli et al., eds., "Plasma exchange and immunoadsorption" Urology, 2013, pp. 194-197.
Terasaki PI et al. "Predicting kidney graft failure by HLA antibodies: a prospective trial." Am J Transplant. Mar. 2004;4(3):438-443.
Tradtrantip L et al. "Therapeutic cleavage of anti-aquaporin—4 autoantibody in neuromyelitis optica by an IgG-selective proteinase." Mol Pharmacol. Jun. 2013;83(6):1268-75.
Vafia K et al. "Enzymatic change of autoantibody glycosylation modulates Fc gamma R expression and reverts pathogenic effects of autoantibodies already bound to their skin target." J Investigative Dermatology. 2012 vol. 132, S51.
Vincents B et al. "Enzymatic characterization of the streptococcal endopeptidase, IdeS, reveals that it is a cysteine protease with strict specificity for IgG cleavage due to exosite binding." Biochemistry. Dec. 14, 2004; 43(49):15540-9.
Vindebro R et al. "Rapid IgG heavy chain cleavage by the streptococcal IgG endopeptidase IdeS is mediated by IdeS monomers and is not due to enzyme dimerization." FEBS Lett. Jun. 19, 2013;587(12):1818-22.
Vo AA et al. "Analysis of subcutaneous (SQ) alemtuzumab induction therapy in highly sensitized patients desensitized with IVIG and rituximab." Am J Transplant. Jan. 2008; 8(1):144-9.
Vo AA et al. "Efficacy, outcomes, and cost-effectiveness of desensitization using IVIG and rituximab." Transplantation. Mar. 27, 2013; 95(6):852-8.
Vo AA et al. "Rituximab and intravenous immune globulin for desensitization during renal transplantation." N Engl J Med. Jul. 17, 2008; 359(3):242-51.
Von Pawel-Rammingen U et al. "IdeS, a novel streptococcal cysteine proteinase with unique specificity for immunoglobulin G." EMBO J. Apr. 2, 2002; 21(7):1607-15.
Wenig K et al. "Structure of the streptococcal endopeptidase IdeS, a cysteine proteinase with strict specificity for IgG." Proc Natl Acad Sci U S A. Dec. 14, 2004; 101(50):17371-6.
Witkowski et al., Biochemistry 38(36): 11643-50 (Year: 1999).
Yang R et al. "Successful treatment of experimental glomerulonephritis with IdeS and EndoS, IgG-degrading streptococcal enzymes." Nephrol Dial Transplant. Aug. 2010;25(8):2479-86.

\* cited by examiner

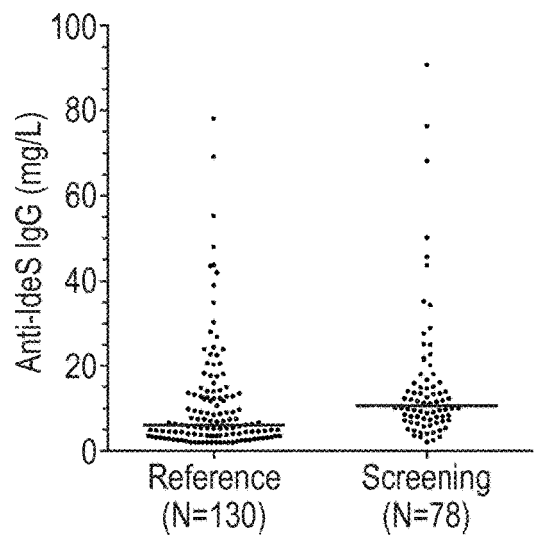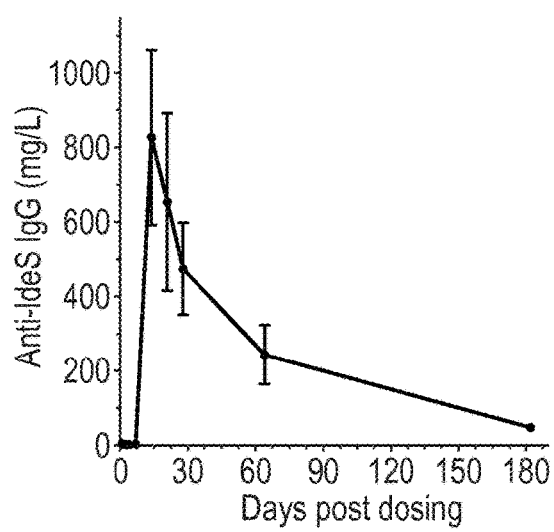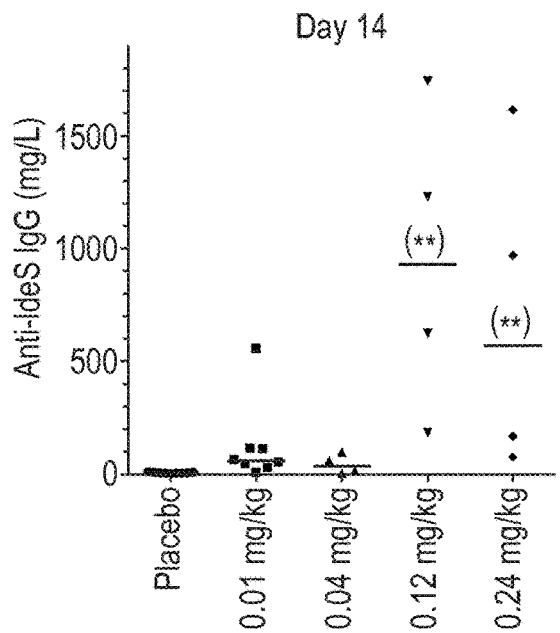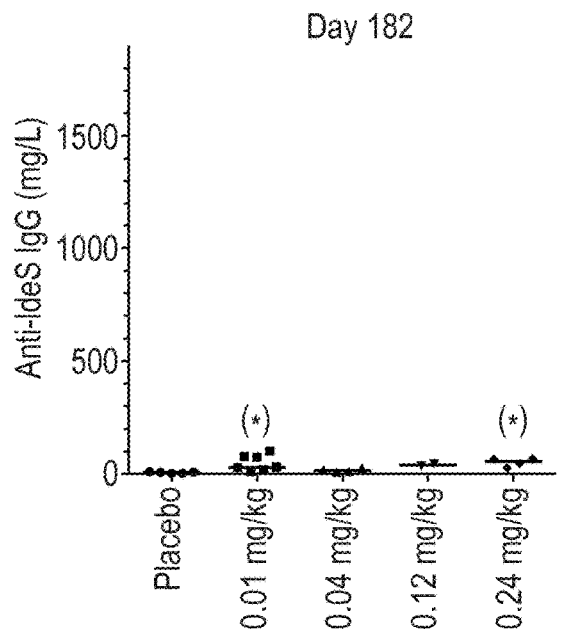

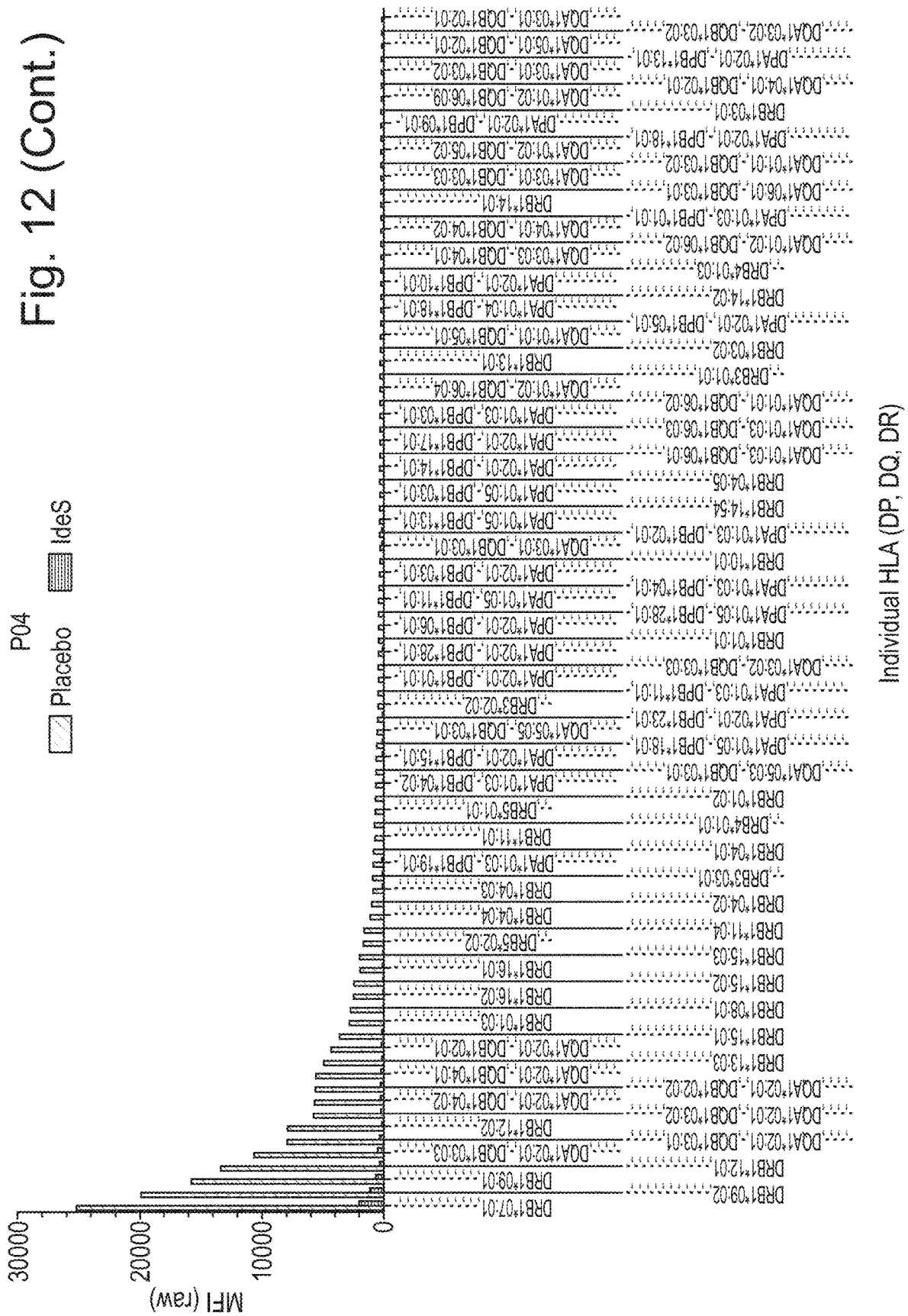

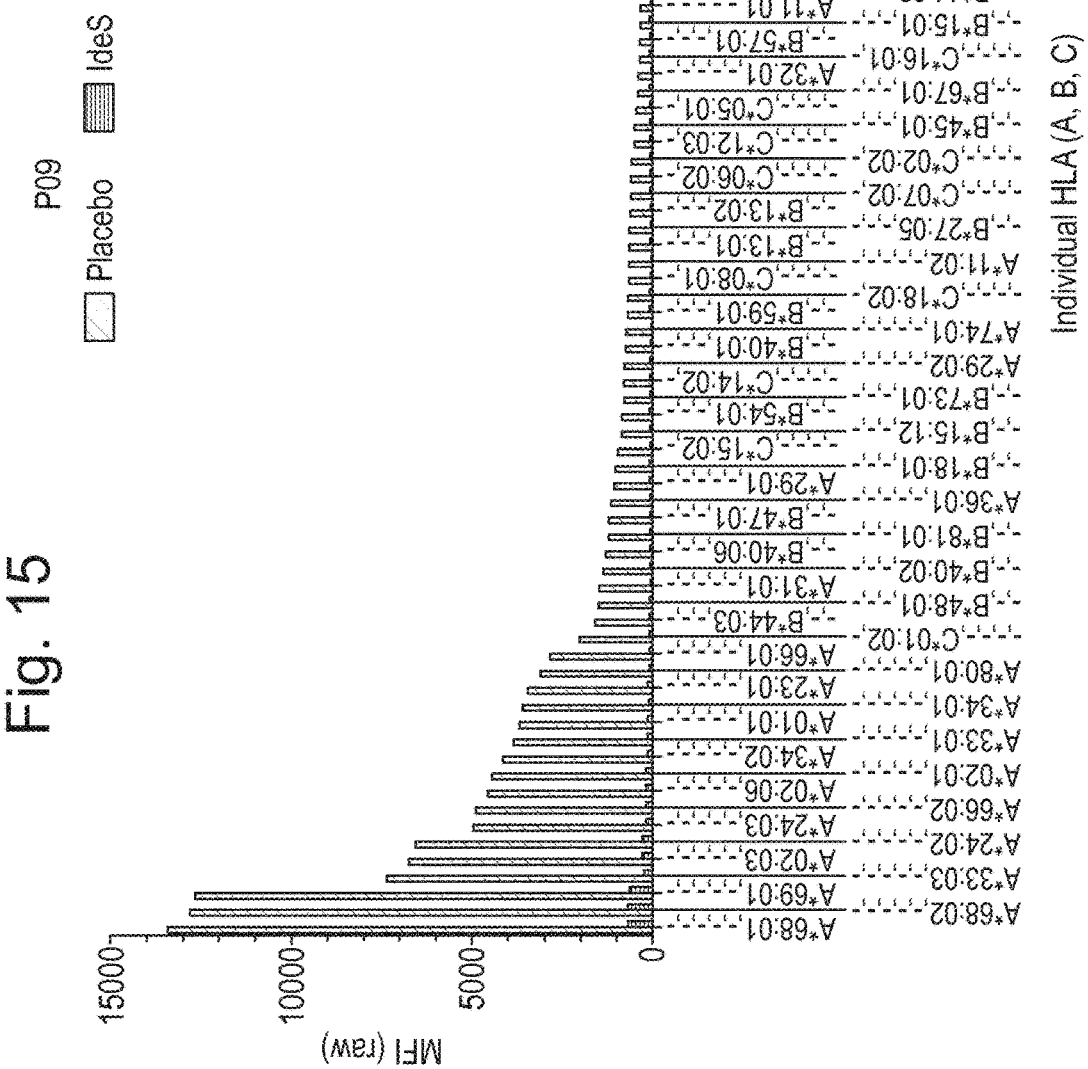

Proliferation
(BrdU incorporation)

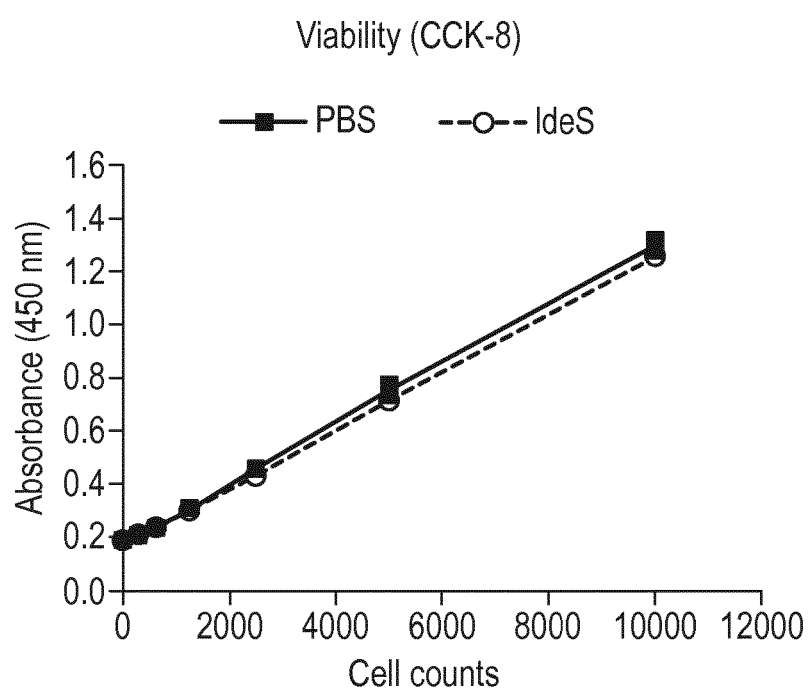

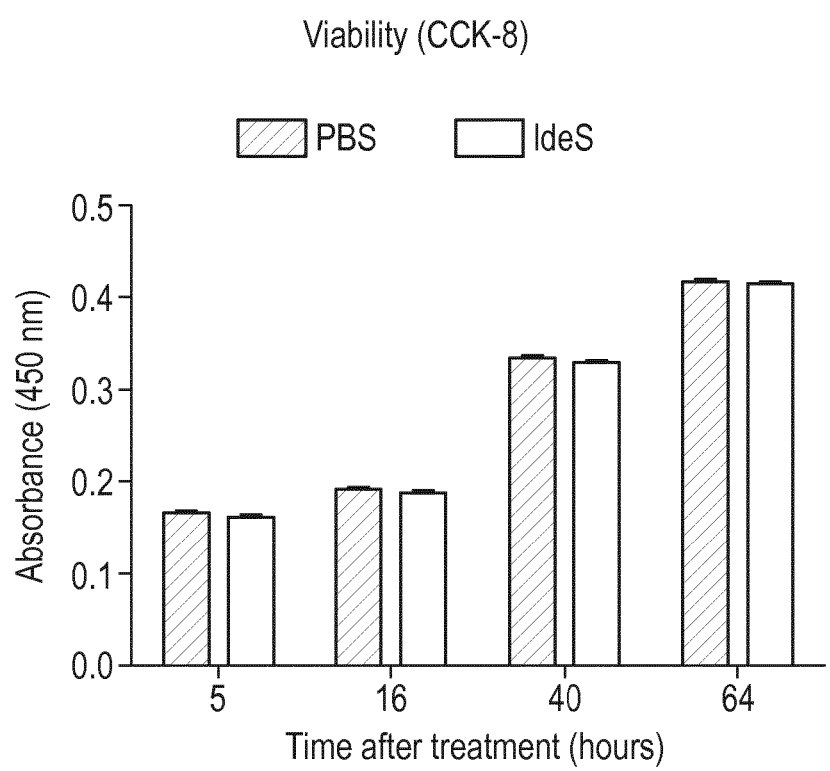

Fig. 31
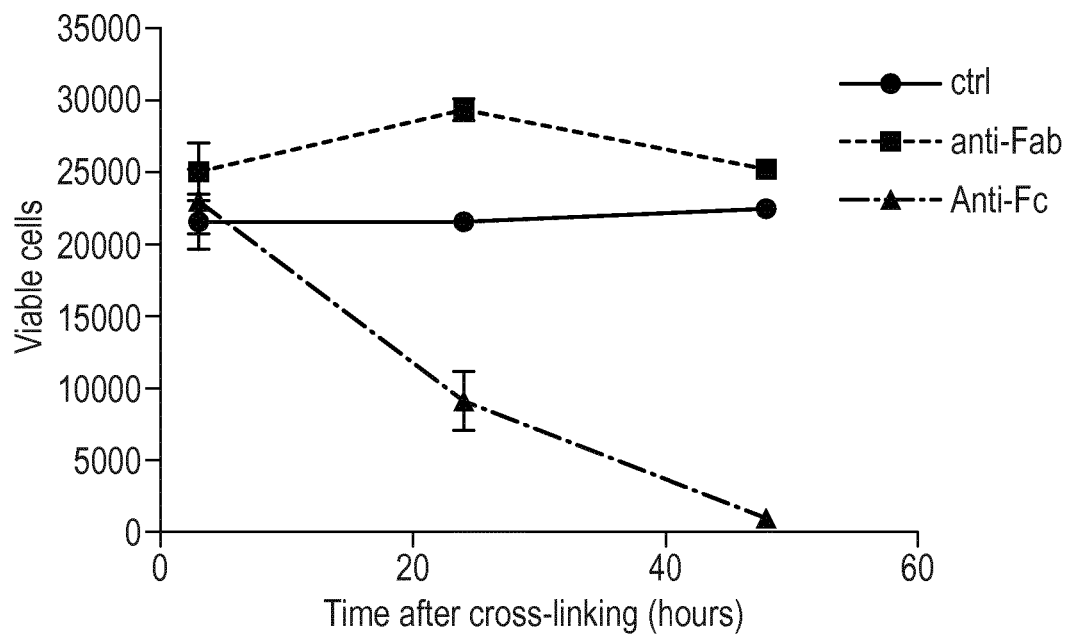
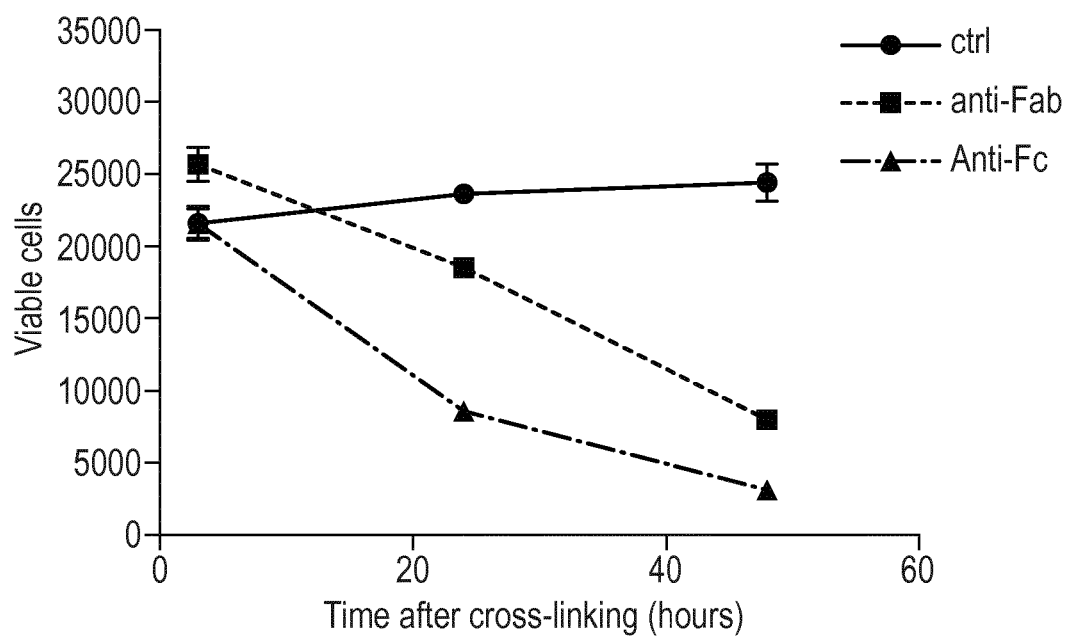

METHOD FOR IMPROVING THE BENEFIT TO A SUBJECT OF A THERAPY OR THERAPEUTIC AGENT

CROSS-REFERENCE TO RELATED APPLICATIONS

The present application is a continuation of U.S. patent application Ser. No. 15/328,879, filed Jan. 24, 2017, which is now U.S. Pat. No. 10,973,889, issued Apr. 13, 2021, which is a national stage entry under 35 U.S.C. § 371 of International Application No. PCT/EP2015/065895, filed Jul. 10, 2015, which claims the benefit of United Kingdom Application No. 1413240.1, filed Jul. 25, 2014, the entire contents of which are incorporated by reference in their entireties for all purposes herein.

SEQUENCE LISTING

This application contains a Sequence Listing which has been submitted electronically in ASCII format and is hereby incorporated by reference in its entirety for all purposes. Said ASCII copy, created Jan. 28, 2016, is named pctep2015065895-seql.txt and is 13,515 bytes in size.

FIELD OF THE INVENTION

The invention relates to a method for improving the benefit of a therapy or a therapeutic agent to a subject. The method comprises (a) administering to the subject an agent which reduces Fc receptor binding of serum IgG molecules in the subject; and (b) subsequently administering said therapy or said therapeutic agent to the subject. The invention also relates to a method for reducing the effect of pathogenic autoantibodies in a subject, the method comprising (a) administering to the subject an agent which reduces Fc receptor binding of serum IgG molecules in the subject and optionally (b) subsequently subjecting the subject to a treatment which removes endogenous autoantibodies. The invention also relates to a kit for carrying out a method of the invention.

BACKGROUND TO THE INVENTION

Antibodies are components of the immune system, which recruit other immune system elements to particular targets within the body. Antibodies are specific to target antigens through the specificity of the Fab domains. Antibodies recruit other elements of the immune system through the interaction of the antibody fragment crystallisable (Fc) domain with Fc receptors (FcRs) expressed on the surface of immune cells. The predominant antibodies in mammalian serum are usually of the immunoglobulin G (IgG) class: IgG1, IgG2, IgG3 and IgG4. These antibodies bind the human FcRs: FcγRI, RγIIa, RγIIb, RγIIIa and FcγRn, and the complement Fc receptor Clq. The efficacy of the recruitment of the cellular immune system by IgG molecules is influenced by the affinity of the Fc to the FcR(s). The interaction between the Fc domain of an antibody and an FcR is important both for the action of antibodies which are administered as therapeutic agents and also of antibodies which play a pathogenic role in various autoimmune conditions including antibody-mediated transplant rejection.

SUMMARY OF THE INVENTION

The inventors have surprisingly shown that it is possible to use an agent to completely, rapidly, temporarily and safely eliminate Fc receptor binding by all or substantially all IgG molecules in the serum of a patient. This creates a window of a defined length in which, if a therapeutic antibody is administered, it will have enhanced efficacy because it does not need to compete for binding to Fc receptors with endogenous IgG. Thus, in one embodiment, the method may be used to treat a disease which is treated by a therapeutic antibody.

The window of defined length may also be used to administer a therapy, such as an organ transplant, which would otherwise be ineffective due to the action of anti-donor IgG antibodies present in the serum of the patient. Thus, in one embodiment, the method may be used to desensitize a patient prior to organ transplantation.

Thus, the present invention provides a method for improving the benefit to a subject of a therapy or a therapeutic agent, the method comprising (a) administering to the subject an agent which reduces Fc receptor binding of serum IgG molecules in the subject; and (b) subsequently administering said therapy or said therapeutic agent to the subject; wherein:
  the amount of said agent administered is sufficient to eliminate Fc receptor binding by all or substantially all IgG molecules present in the serum of the subject; and
  steps (a) and (b) are separated by a time interval which is sufficient for Fc receptor binding by substantially all IgG molecules present in the serum of the subject to be eliminated.

The said interval may typically be of at least 30 minutes and at most 21 days.

The invention may also be used to remove or to reduce the effect of antibodies in a subject. This may be particularly helpful in a patient suffering from an autoimmune disease which is wholly or partly mediated by pathogenic autoantibodies, such as Guillain-Barre syndrome or Goodpastures syndrome. Thus the invention also relates to a method for removing or reducing the effect of antibodies in a subject, the method comprising (a) administering to the subject an agent which reduces Fc receptor binding of serum IgG molecules in the subject, and optionally (b) subsequently subjecting the subject to a treatment which removes endogenous autoantibodies; wherein
  steps (a) and (b) are separated by a time interval of at least 2 weeks; and
  said treatment which removes endogenous autoantibodies is plasmapharesis or immunoadsoprtion, or is administration of an agent (such as an anti-FcRn antibody) which prevents recycling of antibodies in serum by the FcRn receptor, thereby reducing antibody half-life.

The invention also provides a method for assessing the quantity of intact IgG in a sample taken from an individual, the method comprising:
  (i) incubating the sample with a first agent which specifically binds to the F(ab')$_2$ portion of IgG;
  (ii) incubating the sample with a second agent which specifically binds to the Fc portion of IgG;
  (iii) determining the concentration of intact IgG in the sample by determining the presence of both agents The invention also provides a kit for carrying out a method of the invention.

BRIEF DESCRIPTION OF THE FIGURES

FIG. 2A is a graph showing the monitoring of proteinuria in subjects given placebo (n=9). FIG. 2B is a graph showing the monitoring of proteinuria in subjects given a single dose of 0.24 mg/kg BW IdeS (n=4).

FIG. 3A is a graph comparing serum IdeS concentration one minute before end of infusion versus dose levels of IdeS (0.01, 0.04, 0.12, and 0.24 mg/kg BW) (logarithmic scale: circles individual concentrations). Analyte: peptide LFEYFK (n=20). FIG. 3B is a graph comparing serum concentration of mean values of four peptides (AFPYLSTK, AIYVTDSDS-NASIGMK, GGIFDAVFTR and LFEYFK) versus time profiles up to 24 hours after infusion of 0.12 or 0.24 mg/kg BW IdeS (n=8).

FIG. 4A shows the results of SDS-PAGE analysis of serum from subjects dosed with 0.12 mg/kg BW IdeS. FIG. 4B shows the results of SDS-PAGE analysis of serum from subjects dosed with 0.24 mg/kg BW IdeS. FIGS. 4A and 4B show protein banding patterns at pre-dosing, 14 min, 20 min, 1, 2, 6 and 24 hours after dosing. FIG. 4C shows the results of analyzing IgG recovery in serum from one subject in the 0.24 mg/kg BW group at pre-dosing, 2 hours, 24 hours, 7 days, 14, 21, 28 and 35 days after dosing. Arrows to the right in each figure show the different bands in the IgG-marker containing a mix of human IgG, scIgG, F(ab')$_2$ and Fc. Lines to the left in each figure show the molecular mass of the kD standard. The gels show a representative subject in the 0.12 and 0.24 mg/kg BW IdeS dose groups.

FIG. 8A is a graph showing the phagocytosis level before and 24 hours after dosing of 0.24 mg/kg BW IdeS vs. placebo treated subjects. Pre-dose phagocytosis level for each individual was set to 100% and background is spontaneous uptake of beads in the absence of serum, n=4 in the IdeS group and n=2 in the placebo group.

FIG. 8B is a graph showing kinetics of the phagocytic potential in serum is shown for one representative subject in the 0.24 mg/kg BW group at different time-points (pre-dose, 2, 6, 24, 48 hours, 4, 7 and 14 days). The spontaneous uptake of beads in the absence of IgG is shown as an open box. P-value was calculated using Mann-Whitney, ***=P<0.01.

FIGS. 9A-9D. Anti-IdeS antibodies were followed before and throughout the study. Human serum samples were analysed using an IdeS specific CAP-FEIA (ImmunoCAP) assay (Thermo Fisher Scientific) on a Phadia® 250 instrument. The cut-off (LLOQ) for IgG was 2 mg/L. FIG. 9A shows the analysis of samples from 130 human donors (reference) when compared to the 78 healthy human male subjects screened in this study (screening). The highlighted lines show median for the reference group (6.1 mg/L) and the screening group (10.6 mg/L). FIG. 9B is a graph showing kinetics of the anti-IdeS IgG levels shown as a mean for the 0.12 and 0.24 mg/kg groups (n=8; error bars, mean #SEM). No increase in anti-IdeS IgG is seen in any of the subjects prior to day 14. FIG. 9C shows Anti-IdeS IgG levels shown for the separate groups at day 14. FIG. 9D shows Anti-IdeS IgG levels shown for the separate groups at day 182. The lines show median level for each group. P-values were calculated using Kruskal-Wallis, One-Way ANOVA and Dunn's Multiple Comparison: *=P<0.05 and **=P<0.02.

FIG. 20A shows flow cytometry analysis of anti-Fab signal on IgG-type (Nu-DUL-1) and IgM-type (Daudi) of BCR expressing cells after treatment with indicated amounts of IdeS. The y-axis shows mean fluorescent intensity in FL4. FIG. 20B shows flow cytometry analysis of anti-Fab and anti-Fc on the surface of Nu-DUL-1 cells after treatment with different amounts of IdeS.

In FIG. 21A, Heparinized peripheral blood was treated with PBS or different amounts of IdeS. After incubation period plasma was isolated and separated on an SDS-PAGE gel as shown. Intact IgG, scIgG and F(ab')$_2$ fragments are indicated to the right. FIG. 21B is a graph showing the analysis of PBMC's purified from the same PBS or IdeS treated blood when double stained for CD19$^+$ and anti-Fc or anti-Fab.

FIG. 22A is a graph showing that negative selection of B-cells using RosetteSep resulted in >90% CD19$^+$ cells.

FIG. 22B is a graph showing that the F(ab')$_2$ part of surface IgG from CD19$^+$/CD27$^+$ cells is efficiently cleaved by IdeS. The amount of cell-membrane anchored Fc epitopes does not change after IdeS treatment.

FIGS. 23A-23C show the recovery of cells after IdeS treatment. FIG. 23A is a graph showing flow cytometry analysis of anti-Fab on the surface of Nu-DUL-1 cells after treatment with different amounts of IdeS. IdeS was removed and cells were cultured and analyzed after 1 hour and after 24 hours. FIG. 23B is a graph showing the proliferation of cells by measuring BrdU incorporation, where the Nu-DUL-1 cells were treated with different amounts of IdeS or anti-proliferative control substances (cytochalasin D and puromycin) and cultured for 24 hours prior to BrdU 6 hours pulse time. FIG. 23C is a graph showing viability of Nu-DUL-1 cells were treated with PBS or 30 µg/ml IdeS for 24 hours before an intracellular hydrogenase-activity based viability assay (CCK-8) was used as read-out.

FIG. 24A shows flow cytometry analysis of anti-Fab signal on CD19$^+$ cells immediately after PBS or IdeS treatment (30 µg/ml) and after 16 hours of IdeS-free culturing. Double positive cells are found in R2. FIG. 24B shows flow cytometry analysis of anti-Fc signal on CD19$^+$ cells immediately after PBS or IdeS treatment (30 µg/ml) and after 16 hours of culturing. Double positive cells are found in R2 and expressed as percentage of cells in gate P3.

FIG. 25A is a graph showing flow cytometry analysis of anti-Fab signal on enriched B-cells immediately after PBS or IdeS treatment (30 µg/ml) and at indicated time points after treatment. FIG. 25B is a graph showing flow cytometry analysis of anti-Fc signal on enriched B-cells immediately after PBS or IdeS treatment (30 µg/ml) and at different time points after treatment.

FIG. 26 shows IdeS does not affect viability of B-cells. RosetteSep enriched B-cells, containing >90% CD19$^+$ cells were kept in culture for several days after PBS or IdeS (30 µg/ml) treatment and viability was measured using the colorimetric CCK-8 assay.

FIG. 27A is a graph following ERK 1/2 phosphorylation at different time points after stimulation using a phospho-specific antibody in flow cytometry. FIG. 27B is a graph following PLC-γ2 phosphorylation at different time points after stimulation using a phospho-specific antibody in flow cytometry.

FIG. 28A is an image of a filter plate, where the filter plate was seeded with 50 000 or 100 000 cells and treated with/without IdeS and with/without rIL2/R848 on day 0. In one set-up, IdeS was added at day 3 of stimulation with R848 and IL2. FIG. 28B is a graph showing the number of IgA, IgM and IgG producing cells after stimulation with rIL2/R848 in the presence or absence of 30 µg/ml IdeS for 96 hours. FIG. 28C is a graph showing the number of IgG producing cells after stimulation with rIL2/R848 in the presence or absence of 0.3-30 µg/ml IdeS for 72 hours. FIG. 28D is a graph showing the number of IgG producing cells after pre-treating cells for one hour with 0.3-30 µg/ml IdeS prior to removing IdeS and subjected cells to 72 hours of stimulation with rIL2/R848.

FIG. 31 shows B cell viability after antibody cross-linking of IdeS-treated cells (top) and PBS-treated cells (bottom) during a 48 hour assay period.

DESCRIPTION OF THE SEQUENCES

Figure 1:
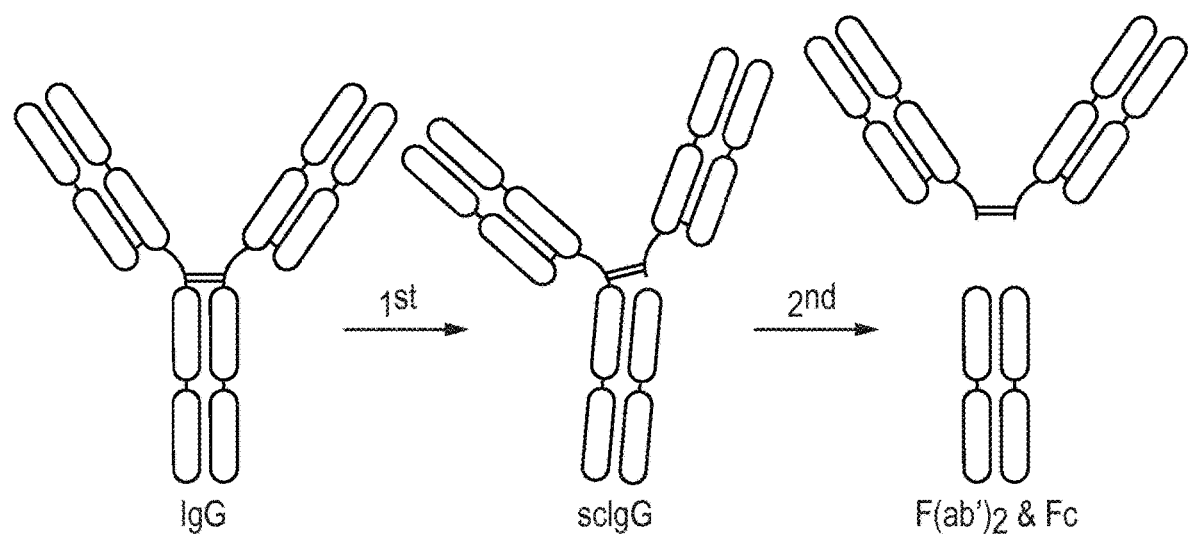
FIG. 1. Schematic representation of IgG cleavage by IdeS. Intact human IgG, regardless of isotype, is cleaved by IdeS in two steps. The first step generates a single-cleaved IgG (scIgG) with one intact heavy chain. The second step generates the fully cleaved products consisting of one F(ab')$_2$ fragment and one homo-dimeric Fc-fragment hold together by non-covalent interactions.

SEQ ID NO: 1 shows the amino acid sequence of mature Immunoglobulin G-degrading enzyme of *S. pyogenes*

(IdeS). This protein is sometimes referred to as MAC1. The full sequence of MAC1 including secretion signal is available as Genbank Accession no. WP_010922160.1.

SEQ ID NO: 2 shows the amino acid sequence of mature Endoglycosidase S (EndoS). Full sequence including secretion signal is available at Genbank Accession no. AAK00850.1.

SEQ ID NO: 3 shows the amino acid sequence of mature MAC2, a variant of IdeS. The full sequence of MAC 2 including secretion signal is available as Genbank Accession no. AFC67907.1.

DETAILED DESCRIPTION OF THE INVENTION

It is to be understood that different applications of the disclosed methods may be tailored to the specific needs in the art. It is also to be understood that the terminology used herein is for the purpose of describing particular embodiments of the invention only, and is not intended to be limiting.

In addition as used in this specification and the appended claims, the singular forms "a", "an", and "the" include plural referents unless the content clearly dictates otherwise. Thus, for example, reference to "a lung" includes "lungs", reference to "an antigen" includes two or more such antigens, reference to "a subject" includes two or more such subjects, and the like.

The terms "patient" and "subject" are used interchangeably and typically refer to a human.

As used herein, "an agent which reduces Fc receptor binding to serum IgG molecules" means an agent which achieves this effect by any suitable mechanism. Various agents are known to reduce the Fc receptor interaction of IgG molecules. These agents are often proteins of bacterial origin and may act in a variety of different ways.

For example, such a protein may be an IgG cysteine protease which cleaves IgG such that the antigen binding domains and Fc interacting domains are separated from each other. In such cases, Fc receptor interaction of serum IgG molecules is reduced because the quantity of intact IgG molecules in the serum is reduced.

As another example, such a protein may be an IgG endoglycosidase which cleaves a glycan structure on the Fc interacting domain of IgG, particularly the N-linked bi-antennary glycan at position Asn-297 (Kabat numbering). This glycan structure has a critical role in Fc receptor binding. Thus, when it is wholly or partially removed by a protein, this will lead to reduced Fc receptor binding by an otherwise intact IgG molecule. In such cases, the reduction in binding preferably results in an increase in the equilibrium binding constant for the IgG: FcγR interaction by a factor of at least two. Preferably, the agent increases the equilibrium binding constant for the IgG: FcγR interaction by a factor of at least two, or at least 3, or at least 4, or at least 5, or at least 6, or at least 7 or at least 8. More preferably, the agent increases the equilibrium binding constant for the IgG: FcγR interaction by a factor of at least eight. An increase in the equilibrium binding constant represents a decrease in the binding between IgG and an FcγR (e.g. between IgG and FcγRIIA).

As used herein, the term "serum IgG molecule" refers to any gamma immunoglobulin (IgG1, IgG2, IgG3 and IgG4) molecule which is present in human tissue prior to a method of the invention being carried out. Such IgG molecules may have been produced endogenously from an individual's B-cells or may be exogenous gamma immunoglobulins which have been administered to a subject prior to the method of the invention being carried out.

As used herein, the term "Fc receptor" refers to Fc gamma immunoglobulin receptors (FcγRs) which are present on cells. In humans, FcγR refers to one, some, or all of the family of receptors comprising FcγRI (CD64), FcγRIIA (CD32A), FcγRIIB (CD32B), FcγRIIIA (CD16a) and FcγRIIIB (CD16b). As used herein, the term FcγR includes naturally occurring polymorphisms of FcγRI (CD64), FcγRIIA (CD32A), FcγRIIB (CD32B), FcγRIIIA (CD16a) and FcγRIIIB (CD16b).

All publications, patents and patent applications cited herein, whether supra or infra, are hereby incorporated by reference in their entirety.

Methods for Improving Benefit of a Therapy or a Therapeutic Agent

The present invention provides a method for improving the benefit to a subject of a therapy or a therapeutic agent. The method comprises two steps, which are referred to herein as steps (a) and (b).

Step (a) comprises administering to the subject an agent which reduces Fc receptor binding of serum IgG molecules in the subject. The amount of the agent administered is preferably sufficient to eliminate Fc receptor binding by all or substantially all IgG molecules present in the serum of the subject.

Step (b) comprises subsequently administering to the subject the said therapy or therapeutic agent.

Steps (a) and (b) are separated by a time interval which is preferably sufficient for Fc receptor binding by all or substantially all IgG molecules present in the serum of the subject to be eliminated. The said interval may typically be of at least 30 minutes and at most 21 days.

The invention also provides an agent which reduces Fc receptor binding of serum IgG molecules in a subject for use in a method for improving the benefit to said subject of a therapy or a therapeutic agent, wherein the method comprises: (a) administering to the subject an amount of the agent sufficient to eliminate Fc receptor binding by all or substantially all IgG molecules present in the serum of the subject; and (b) subsequently administering said therapy or said therapeutic agent to the subject, wherein steps (a) and (b) are separated by a time interval sufficient for Fc receptor binding by substantially all IgG molecules present in the serum of the subject to be eliminated. The said interval may typically be of at least 30 minutes and at most 21 days.

The invention also provides the use of an agent which reduces Fc receptor binding of serum IgG molecules in a subject in the manufacture of a medicament for improving the benefit to said subject of a therapy or a therapeutic agent, wherein said improving comprises: (a) administering to the subject an amount of the agent sufficient to eliminate Fc receptor binding by all or substantially all IgG molecules present in the serum of the subject; and (b) subsequently administering said therapy or said therapeutic agent to the subject, wherein steps (a) and (b) are separated by a time interval sufficient for Fc receptor binding by substantially all IgG molecules present in the serum of the subject to be eliminated. The said interval may typically be of at least 30 minutes and at most 21 days.

Timing and Order of Steps (a) and (b)

Step (a) is conducted before step (b), and steps (a) and (b) are separated by a time interval sufficient for Fc receptor binding by all or substantially all IgG molecules present in the serum of the subject to be eliminated. By "substantially all" it is typically meant that Fc receptor binding by serum IgG is reduced to less than 5% of the level that was present prior to step (a). For example, if the agent administered is (a) is a protease (such as IdeS), the interval will be the time required for the agent to cleave at least 95% of serum IgG in the subject, as measured by any suitable assay. The said interval may typically be of at least 30 minutes and at most 21 days.

The lower limit of the time interval between steps (a) and (b) is determined by the time that it takes for the agent administered in step (a) to eliminate Fc receptor binding by substantially all IgG molecules present in the serum of the subject. This may optionally be determined by testing a serum sample taken from the individual and applying any suitable assay. Some exemplary suitable assays are described in the Examples.

Such an assay may directly test for the presence of IgG molecules in a serum sample that are able to bind to one or more Fc receptors, for example in an ELISA. Alternatively, such an assay may be indirect, in that it may test for the presence of one or more reaction products that are expected to result from the treatment of IgG with the agent administered in step (a). For example, where the agent is an enzyme which cleaves the IgG protein, a serum sample may be assayed for the presence of intact IgG molecules or the fragments which result from cleavage. This may be achieved by any suitable method, such as by separating the molecules and fragments based on molecular weight, e.g. by mass spectrometry or SDS-PAGE, or by specific detection of the molecules or fragments, e.g. by ELISA. Alternatively IgG may be detected by mixing serum from a subject with cells expressing FcgR's and monitoring IgG binding by flow cytometry using fluorochrome conjugated anti-human IgG.

Conventional methods for assessing the quantity of IgG in a sample, such as a serum sample, in a clinical setting rely on nephelometry and turbidimetry because of their speed, ease of use and precision. In both nephelometry and turbidimetry, a light source is projected through a liquid sample within a transparent container. Turbidimetry measures the decrease in the intensity of light and nephelometry measures scatter of light as it passes through the sample, which is proportional to the concentration of the immunoglobulin in the solution. Both principles are based on added anti IgG antibodies that react with antigen in the sample to form an antigen/antibody complex (agglutination). Addition of PEG allows the reaction to progress rapidly to the end point, increases sensitivity, and reduces the risk of samples containing excess antigen producing false negative results. In the case of IgG analysis, the $F(ab')_2$-part of IgG is cross-linked by the anti-IgG antibody and cause the agglutination reaction. However, such methods may not be appropriate when some or all of the IgG present may not be intact. For example, if an IgG cysteine protease (such as IdeS) has been administered to the subject from whom the sample is taken, e.g. in a method of the invention, or if such a protease has been administered to the sample, cleavage fragments such as $F(ab')_2$- and Fc-fragments will be present. This does not affect the agglutination reaction of conventional nephelometry and turbidimetry methods as long as the $F(ab')_2$ fragments are still present in the sample. Due to the shorter half-life of $F(ab')_2$ fragments compared to intact IgG, the agglutination will decrease over time though it is not proportional to the amount of intact IgG present in the sample. Thus, samples affected by the presence of an IgG cysteine protease (such as IdeS) cannot be assessed by conventional methods. The inventors developed a new assay for IgG concentration which is compatible with samples affected by the presence of an IgG cysteine protease (such as IdeS) and may be used in any clinical setting, including (but not limited to) uses in combination with other methods of the invention.

Said method is able to discriminate between intact IgG and IdeS-generated $F(ab')_2$-fragments. This was accomplished by making use of antibodies that detect the different fragments i.e. an anti-Fab antibody and an anti-Fc antibody. The antibodies used in the assay must not be a substrate for the IgG cysteine protease affecting the sample (typically IdeS). This avoids the assay reagents being affected by any active protease which may be present in a sample. This can be accomplished by testing IgG from different species or by using antibody fragments (i.e. Fab fragments or $F(ab')_2$ fragments) in place of whole antibodies. Typically, an anti-$F(ab')_2$ agent is incubated with the sample as a capture reagent. The capture reagent is typically immobilized, for example in the wells of an assay plate. Bound IgG is then detected by incubation with an anti-Fc agent as the detector reagent. Thus, only IgG which possess both Fab and Fc parts will be detected, contrary to the nephelometry and turbidimetry methods. The detector reagent may typically be conjugated directly or indirectly to a moiety to facilitate detection, such as a fluorescent dye or an enzyme which reacts with a chromogenic substrate. The capture and detector reagents can be any other molecule that specifically recognizes the Fab- or Fc-part of IgG and can be used in the reverse order i.e. capture using anti-Fc and detect using anti-Fab. The assay may be conducted in any suitable format, such as a conventional ELISA or Meso Scale Discovery format.

In some cases, such as when the IgG cysteine protease is IdeS, the sample may include intermediate fragments such as scIgG in which only one heavy chain is cleaved, and the $F(ab')_2$ remains attached to the other, intact heavy chain. In such cases, the scIgG fragment may be incorrectly identified by the assay as an intact IgG. Thus, the method may include a complimentary step of assessing the sizes of the fragments present in the sample. Since there are no disulphide bridges between the heavy chains below the hinge region, the Fc-part of the heavy chain in an scIgG fragment will separate from the intact heavy-chain under denaturating conditions as an approximately 20-25 kDa protein. The different fragment sizes can be detected and quantified using any suitable method, such as SDS-PAGE. A specific embodiment of the method, including the optional complimentary step is described in Example 1 (see Efficacy assessment). The method is particularly useful for assessing the efficacy of IdeS in a clinical setting.

Where the agent of step (a) is an enzyme which cleaves a glycan moiety on IgG, a serum sample may be assayed for the presence of IgG molecules which possess either normal or truncated glycans, or for the glycan fragments that result from cleavage. This may be achieved by any suitable method, such as by separating the molecules and/or fragments based on molecular weight, e.g. by mass spectrometry or SDS-PAGE, or by specific detection of the molecules or fragments, e.g. by ELISA.

The lower limit of the time interval between steps (a) and (b) may be selected from: at least 30 minutes, at least 1 hour, at least 2 hours, at least 3 hours, at least 4 hours, at least 5 hours, or at least 6 hours. The lower limit may be shorter than any of the above should it be determined that Fc receptor binding by substantially all IgG molecules present in the serum of the subject has been eliminated at an earlier time point.

The upper limit of the time interval between steps (a) and (b) may be selected independently of the lower limit, and may be determined by the time that it takes for endogenous production of IgG to begin to replace or to completely replace the IgG molecules that were present in the serum of the subject prior to carrying out the method. This may be determined by testing a serum sample taken from the individual and applying any suitable assay, such as those described above with respect to the lower limit. Newly-synthesised IgG typically starts to reappear in serum within 3-4 days, with total replacement complete by around 3 weeks (21 days).

The upper limit of the time interval between steps (a) and (b) may be selected independently from the lower limit, and may be selected from: at most 21 days, at most 18 days, at most 14 days, at most 13 days, at most 12 days, at most 11 days, at most 10 days, at most 9 days, at most 8 days, at most 7 days, at most 6 days, at most 5 days, at most 4 days, at most 3 days, at most 2 days, at most 24 hours, at most 18 hours, at most 12 hours, at most 10 hours, at most 8 hours, at most 7 hours, at most 6 hours, at most 5 hours, at most 4 hours, at most 3 hours, at most 2 hours, or at most 1 hour.

Preferably the time interval between steps (a) and (b) is at most 24 hours, more preferably at most 12 hours, most preferably at most 6 hours, so that steps (a) and (b) may be carried out on the same day or during the same visit to a treatment centre. This is highly advantageous, particularly where access to treatments centres may be limited. As such the time interval between steps (a) and (b) should be long enough for the agent administered in step (a) to eliminate Fc receptor binding by substantially all IgG molecules present in the serum of the subject, but is at most around 6 hours. Thus, the interval between steps (a) and (b) is preferably minutes to 1 hour, 30 minutes to 2 hours, 30 minutes to 3 hours, 30 minutes to 4 hours, 30 minutes to 5 hours, 30 minutes to 6 hours, 1 to 2 hours, 1 to 3 hours, 1 to 4 hours, 1 to 5 hours, 1 to 6 hours, 2 to 3 hours, 2 to 4 hours, 2 to 5 hours, 2 to 6 hours, 3 to 4 hours, 3 to 5 hours, 3 to 6 hours, 4 to 5 hours, 4 to 6 hours, or 5 to 6 hours.

Step (a)

In step (a), an effective amount of an agent which reduces Fc receptor binding of serum IgG molecules in a subject is administered to the subject. By "effective amount" it is meant that the amount of the agent is sufficient to eliminate Fc receptor binding by substantially all IgG molecules present in the serum of the subject.

The Agent

The agent is typically a protein, typically of bacterial origin. The agent may be a protein which has IgG cysteine protease activity, preferably cleaving in the hinge region of the immunoglobulin molecule. An example of such a protein is IdeS (Immunoglobulin G-degrading enzyme of *S. pyogenes*). IdeS is a streptococcal protease with a unique degree of specificity; it cleaves Immunoglobulin G (IgG) antibodies but no other substrate (including IgA, IgD, IgE and IgM). IdeS cleaves human IgG into $F(ab')_2$ and Fc fragments at a defined site COOH-terminally of the hinge region (see FIG. 1). The mature sequence of IdeS is provided as SEQ ID NO: 1. The agent may be a protein comprising or consisting of the amino acid sequence of SEQ ID NO: 1, or may be a homologue thereof from an alternative bacterium.

Alternatively the agent may be a variant of the IdeS protein which comprises or consists of any amino acid sequence which has at least 80%, 85%, 90% or 95% identity with SEQ ID NO: 1 and has IgG cysteine protease activity. A preferred variant is the protein MAC2, the full sequence of which is available as Genbank Accession no. AFC67907.1. The sequence of MAC2 without signal sequence is provided as SEQ ID NO: 3. The agent may be a protein comprising or consisting of the amino acid sequence of SEQ ID NO: 3, or may be a homologue thereof from an alternative bacterium.

A variant of the IdeS protein may comprise or consist of an amino acid sequence in which up to 1, 2, 3, 4, 5, 10, 20, 30 or more, amino acid substitutions, insertions or deletions have been made relative to the amino acid sequence of SEQ ID NO: 1, provided the variant has IgG cysteine protease activity. Said amino acid substitutions are preferably conservative. Conservative substitutions replace amino acids with other amino acids of similar chemical structure, similar chemical properties or similar side-chain volume. The amino acids introduced may have similar polarity, hydrophilicity, hydrophobicity, basicity, acidity, neutrality or charge to the amino acids they replace. Alternatively, the conservative substitution may introduce another amino acid that is aromatic or aliphatic in the place of a pre-existing aromatic or aliphatic amino acid. Conservative amino acid changes are well-known in the art and may be selected in accordance with the properties of the 20 main amino acids as defined in Table 1 below. Where amino acids have similar polarity, this can be determined by reference to the hydropathy scale for amino acid side chains in Table 2.

TABLE 1

Chemical properties of amino acids

| | | | |
|---|---|---|---|
| Ala | aliphatic, hydrophobic, neutral | Met | hydrophobic, neutral |
| Cys | polar, hydrophobic, neutral | Asn | polar, hydrophilic, neutral |
| Asp | polar, hydrophilic, charged (−) | Pro | hydrophobic, neutral |
| Glu | polar, hydrophilic, charged (−) | Gln | polar, hydrophilic, neutral |
| Phe | aromatic, hydrophobic, neutral | Arg | polar, hydrophilic, charged (+) |
| Gly | aliphatic, neutral | Ser | polar, hydrophilic, neutral |
| His | aromatic, polar, hydrophilic, charged (+) | Thr | polar, hydrophilic, neutral |
| Ile | aliphatic, hydrophobic, neutral | Val | aliphatic, hydrophobic, neutral |
| Lys | polar, hydrophilic, charged (+) | Trp | aromatic, hydrophobic, neutral |
| Leu | aliphatic, hydrophobic, neutral | Tyr | aromatic, polar, hydrophobic |

TABLE 2

Hydropathy scale

| Side Chain | Hydropathy |
|---|---|
| Ile | 4.5 |
| Val | 4.2 |
| Leu | 3.8 |
| Phe | 2.8 |
| Cys | 2.5 |

TABLE 2-continued

Hydropathy scale

| Side Chain | Hydropathy |
|---|---|
| Met | 1.9 |
| Ala | 1.8 |
| Gly | −0.4 |
| Thr | −0.7 |
| Ser | −0.8 |
| Trp | −0.9 |
| Tyr | −1.3 |
| Pro | −1.6 |
| His | −3.2 |
| Glu | −3.5 |
| Gln | −3.5 |
| Asp | −3.5 |
| Asn | −3.5 |
| Lys | −3.9 |
| Arg | −4.5 |

Alternatively the agent may be a protein, which comprises or consists of a fragment of SEQ ID NO: 1 or SEQ ID NO: 3, and has IgG cysteine protease activity, preferably wherein said fragment is 100 to 300, 150 to 300 or 200 to 300 amino acids in length. The fragment may be created by the deletion of one or more amino acid residues of the amino acid sequence of SEQ ID NO: 1 or SEQ ID NO: 3. Up to 1, 2, 3, 4, 5, 10, 20, 30, 40 or 50 residues may be deleted, or more. The deleted residues may be contiguous with each other.

Figure 18:
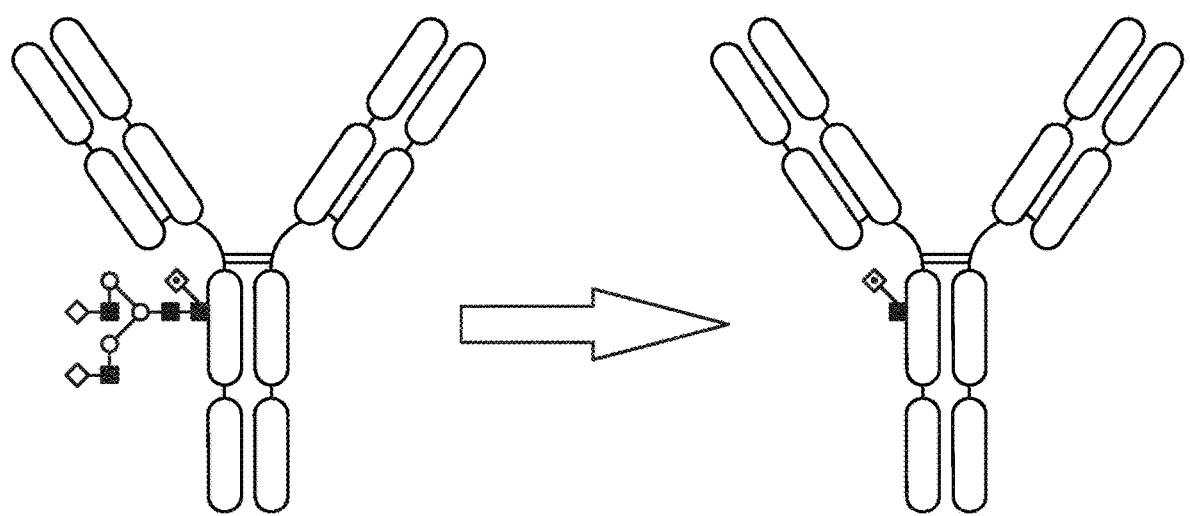
FIG. 18 shows a schematic representation of the cleavage of the N-linked glycan at Asn-297 (Kabat numbering) of IgG by EndoS.

The agent may be a protein which has IgG endoglycosidase activity, preferably cleaving the glycan moiety at Asn-297 (Kabat numbering) in the Fc region of IgG. An example of such a protein is EndoS (Endoglycosidase of *S. pyogenes*). EndoS hydrolyzes the β-1,4-di-N-acetylchitobiose core of the asparagine-linked glycan of normally-glycosylated IgG (see FIG. 18). The mature sequence of EndoS is provided as SEQ ID NO: 2. The agent may be a protein comprising or consisting of the amino acid sequence of SEQ ID NO: 2, or may be a homologue thereof from an alternative bacterium, such as *Streptococcus equi* or *Streptococcus zooepidemicus*, or *Corynebacterium pseudotuberculosis*, *Enterococcus faecalis*, or *Elizabethkingia meningoseptica*. The agent may be CP40, EndoE, or EndoF2.

Alternatively the agent may be a variant of the EndoS protein which comprises or consists of any amino acid sequence which has at least 80%, 85%, 90% or 95% identity with SEQ ID NO: 2 and has IgG endoglycosidase activity. A variant of the EndoS protein may comprise or consist of an amino acid sequence in which up to 1, 2, 3, 4, 5, 10, 20, 30, 40, 50, 60, 70, 80, 90, or more, amino acid substitutions, insertions or deletions have been made relative to the amino acid sequence of SEQ ID NO: 2, provided the variant has IgG endoglycosidase activity. Said amino acid substitutions are preferably conservative. Conservative substitutions are as defined above in respect of SEQ ID NO: 1.

Alternatively the agent may be a protein which comprises or consists of a fragment of SEQ ID NO: 2 and has IgG enodglycosidase activity, preferably wherein said fragment is 400 to 950, 500 to 950, 600 to 950, 700 to 950 or 800 to 950 amino acids in length. A preferred fragment consists of amino acids 1 to 409 of SEQ ID NO: 2, which corresponds to the enzymatically active α-domain of EndoS generated by cleavage by the streptococcal cysteine proteinase SpeB. The fragment may be created by the deletion of one or more amino acid residues of the amino acid sequence of SEQ ID NO: 1. Up to 1, 2, 3, 4, 5, 10, 20, 30, 40, 50, 100, 200, 300, 400, 500 or 550 residues may be deleted, or more. The deleted residues may be contiguous with other.

Any fragment or variant of SEQ ID NO: 2 preferably includes residues 191 to 199 of SEQ ID NO: 2, i.e. Leu-191, Asp-192, Gly-193, Leu-194, Asp-195, Val-196, Asp-197, Val-198 and Glu-199 of SEQ ID NO: 1. These amino acids constitute a perfect chitinase family 18 active site, ending with glutamic acid. The glutamic acid in the active site of chitinases is essential for enzymatic activity. Most preferably, therefore, a variant of SEQ ID NO: 2 contains Glu-199 of SEQ ID NO: 2. The variant of SEQ ID NO: 2 may contain residues 191 to 199 of SEQ ID NO: 2 having one or more conservative substitutions, provided that the variant contains Glu-199 of SEQ ID NO: 2.

Administration and Dose

In step (a), the agent is preferably administered by intravenous infusion, but may be administered by any suitable route including, for example, intradermal, subcutaneous, percutaneous, intramuscular, intra-arterial, intraperitoneal, intraarticular, intraosseous or other appropriate administration routes. The amount of said agent that is administered may be between 0.01 mg/kg BW and 2 mg/kg BW, between 0.04 and 2 mg/kg BW, between 0.12 mg/kg BW and 2 mg/kg BW, preferably between 0.24 mg/kg and 2 mg/kg BW and most preferably between 1 mg/kg and 2 mg/kg BW. The agent may be present in a substantially isolated form. It may be mixed with carriers or diluents (as discussed below) which will not interfere with the intended use and still be regarded as substantially isolated. It may also be in a substantially purified form, in which case it will generally comprise at least 90%, e.g. at least 95%, 98% or 99%, of the protein in the preparation.

Formulations and Compositions

The agent is preferably administered together with one or more pharmaceutically acceptable carriers or diluents and optionally one or more other therapeutic ingredients. The carrier(s) must be 'acceptable' in the sense of being compatible with the other ingredients of the formulation and not deleterious to the recipient thereof. Typically, carriers for injection, and the final formulation, are sterile and pyrogen free.

Formulation of a suitable composition can be carried out using standard pharmaceutical formulation chemistries and methodologies all of which are readily available to the reasonably skilled artisan. For example, the agent can be combined with one or more pharmaceutically acceptable excipients or vehicles. Auxiliary substances, such as wetting or emulsifying agents, pH buffering substances and the like, may be present in the excipient or vehicle. These excipients, vehicles and auxiliary substances are generally pharmaceutical agents that do not induce an immune response in the individual receiving the composition, and which may be administered without undue toxicity. Pharmaceutically acceptable excipients include, but are not limited to, liquids such as water, saline, polyethyleneglycol, hyaluronic acid, glycerol, thioglycerol and ethanol. Pharmaceutically acceptable salts can also be included therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients, vehicles and auxiliary substances is available in Remington's Pharmaceutical Sciences (Mack Pub. Co., N.J. 1991).

Such compositions may be prepared, packaged, or sold in a form suitable for bolus administration or for continuous administration. Injectable compositions may be prepared, packaged, or sold in unit dosage form, such as in ampoules or in multi-dose containers containing a preservative. Compositions include, but are not limited to, suspensions, solutions, emulsions in oily or aqueous vehicles, pastes, and implantable sustained-release or biodegradable formulations. Such compositions may further comprise one or more additional ingredients including, but not limited to, suspending, stabilizing, or dispersing agents. In one embodiment of a composition for parenteral administration, the active ingredient is provided in dry (for e.g., a powder or granules) form for reconstitution with a suitable vehicle (e. g., sterile pyrogen-free water) prior to parenteral administration of the reconstituted composition. The compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides.

Other parentally-administrable compositions which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Step (b)

In step (b), a therapy or therapeutic agent is administered to the subject. The therapy or therapeutic agent will typically be administer or practised in precisely the same fashion as would have been used had step (a) not been conducted first.

Therapeutic Agent

In one embodiment, the therapeutic agent is an antibody which is administered for the treatment of cancer or another disease. The therapeutic agent may be intravenous immunoglobulin (IVIG). In the context of this embodiment, the method may be alternatively described as a method for the treatment of cancer or another disease in a subject, the method comprising (a) administering to the subject an agent which reduces Fc receptor binding of serum IgG molecules in the subject; and (b) subsequently administering to the subject a therapeutically effective amount of an antibody which is a treatment for said cancer or said other disease; wherein:

the amount of said agent administered is sufficient to eliminate Fc receptor binding by substantially all IgG molecules present in the serum of the subject; and steps (a) and (b) are separated by a time interval of at least 2 hours and at most 21 days.

The invention also provides the agent for use in such a method for the treatment of cancer or another disease. The invention also provides use of the agent in the manufacture of a medicament for the treatment of cancer or another disease by such a method.

The cancer may be Acute lymphoblastic leukemia, Acute myeloid leukemia, Adrenocortical carcinoma, AIDS-related cancers, AIDS-related lymphoma, Anal cancer, Appendix cancer, Astrocytoma, childhood cerebellar or cerebral, Basal cell carcinoma, Bile duct cancer, extrahepatic, Bladder cancer, Bone cancer, Osteosarcoma/Malignant fibrous histiocytoma, Brainstem glioma, Brain cancer, Brain tumor, cerebellar astrocytoma, Brain tumor, cerebral astrocytoma/ malignant glioma, Brain tumor, ependymoma, Brain tumor, medulloblastoma, Brain tumor, supratentorial primitive neuroectodermal tumors, Brain tumor, visual pathway and hypothalamic glioma, Breast cancer, Bronchial adenomas/carcinoids, Burkitt lymphoma, Carcinoid tumor, Carcinoid tumor, gastrointestinal, Carcinoma of unknown primary, Central nervous system lymphoma, Cerebellar astrocytoma, Cerebral astrocytoma/Malignant glioma, Cervical cancer, Chronic lymphocytic leukemia, Chronic myelogenous leukemia Chronic myeloproliferative disorders, Colon Cancer, Cutaneous T-cell lymphoma, Desmoplastic small round cell tumor, Endometrial cancer, Ependymoma, Esophageal cancer, Ewing's sarcoma in the Ewing family of tumors, Extracranial germ cell tumor, Childhood, Extragonadal Germ cell tumor, Extrahepatic bile duct cancer, Eye Cancer, Intraocular melanoma, Eye Cancer, Retinoblastoma, Gallbladder cancer, Gastric (Stomach) cancer, Gastrointestinal Carcinoid Tumor, Gastrointestinal stromal tumor (GIST), Germ cell tumor: extracranial, extragonadal, or ovarian, Gestational trophoblastic tumor, Glioma of the brain stem, Glioma, Childhood Cerebral Astrocytoma, Glioma, Childhood Visual Pathway and Hypothalamic, Gastric carcinoid, Hairy cell leukemia, Head and neck cancer, Heart cancer, Hepatocellular (liver) cancer, Hodgkin lymphoma, Hypopharyngeal cancer, Hypothalamic and visual pathway glioma, Intraocular Melanoma, Islet Cell Carcinoma (Endocrine Pancreas), Kaposi sarcoma, Kidney cancer (renal cell cancer), Laryngeal Cancer, Leukemias, Leukemia, acute lymphoblastic (also called acute lymphocytic leukemia), Leukemia, acute myeloid (also called acute myelogenous leukemia), Leukemia, chronic lymphocytic (also called chronic lymphocytic leukemia), Leukemia, chronic myelogenous (also called chronic myeloid leukemia), Leukemia, hairy cell, Lip and Oral Cavity Cancer, Liposarcoma, Liver Cancer (Primary), Lung Cancer, Non-Small Cell, Lung Cancer, Small Cell, Lymphomas, Lymphoma, AIDS-related, Lymphoma, Burkitt, Lymphoma, cutaneous T-Cell, Lymphoma, Hodgkin, Lymphomas, Non-Hodgkin (an old classification of all lymphomas except Hodgkin's), Lymphoma, Primary Central Nervous System, Macroglobulinemia, Waldenström, Malignant Fibrous Histiocytoma of Bone/Osteosarcoma, Medulloblastoma, Melanoma, Melanoma, Intraocular (Eye), Merkel Cell Carcinoma, Mesothelioma, Adult Malignant, Mesothelioma, Metastatic Squamous Neck Cancer with Occult Primary, Mouth Cancer, Multiple Endocrine Neoplasia Syndrome, Multiple Myeloma/Plasma Cell Neoplasm, Mycosis Fungoides, Myelodysplastic Syndromes, Myelodysplastic/Myeloproliferative Diseases, Myelogenous Leukemia, Chronic, Myeloid Leukemia, Adult Acute, Myeloid Leukemia, Childhood Acute, Myeloma, Multiple (Cancer of the Bone-Marrow), Myeloproliferative Disorders, Nasal cavity and paranasal sinus cancer, Nasopharyngeal carcinoma, Neuroblastoma, Non-Hodgkin lymphoma, Non-small cell lung cancer, Oral Cancer, Oropharyngeal cancer, Osteosarcoma/malignant fibrous histiocytoma of bone, Ovarian cancer, Ovarian epithelial cancer (Surface epithelial-stromal tumor), Ovarian germ cell tumor, Ovarian low malignant potential tumor, Pancreatic cancer, Pancreatic cancer, islet cell, Paranasal sinus and nasal cavity cancer, Parathyroid cancer, Penile cancer, Pharyngeal cancer, Pheochromocytoma, Pineal astrocytoma, Pineal germinoma, Pineoblastoma and supratentorial primitive neuroectodermal tumors, Pituitary adenoma, Plasma cell neoplasia/Multiple myeloma, Pleuropulmonary blastoma, Primary central nervous system lymphoma, Prostate cancer, Rectal cancer, Renal cell carcinoma (kidney cancer), Renal pelvis and ureter, transitional cell cancer, Retinoblastoma, Rhabdomyosarcoma, Salivary gland cancer, Sarcoma, Ewing family of tumors, Kaposi Sarcoma, Sarcoma, soft tissue, Sarcoma, uterine, Sézary syndrome, Skin cancer (nonmelanoma), Skin cancer (melanoma), Skin carcinoma, Merkel cell, Small cell lung cancer, Small intestine cancer, Soft tissue sarcoma, Squamous cell carcinoma, Squamous neck cancer with occult primary, metastatic, Stomach cancer, Supratentorial primitive neuroectodermal tumor, T-Cell lymphoma, cutaneous—see Mycosis Fungoides and Sézary syndrome, Testicular cancer, Throat cancer, Thymoma, Thymoma and Thymic carcinoma, Thyroid cancer, Thyroid cancer, Transitional cell cancer of the renal pelvis and ureter, Trophoblastic tumor, Ureter and renal pelvis, transitional cell cancer Urethral cancer, Uterine cancer, endometrial, Uterine sarcoma, Vaginal cancer, Visual pathway and hypothalamic glioma, Vulvar cancer, Waldenström macroglobulinemia and Wilms tumor (kidney cancer).

The cancer is preferably prostate cancer, breast cancer, bladder cancer, colon cancer, rectal cancer, pancreatic cancer, ovarian cancer, lung cancer, cervical cancer, endometrial cancer, kidney (renal cell) cancer, oesophageal cancer, thyroid cancer, skin cancer, lymphoma, melanoma or leukemia.

The antibody administered in step (b) is preferably specific for a tumour antigen associated with one or more of the above cancer types. Targets of interest for an antibody for use in the method include CD2, CD3, CD19, CD20, CD22, CD25, CD30, CD32, CD33, CD40, CD52, CD54, CD56, CD64, CD70, CD74, CD79, CD80, CD86, CD105, CD138, CD174, CD205, CD227, CD326, CD340, MUC16, GPNMB, PSMA, Cripto, ED-B, TMEFF2, EphA2, EphB2, FAP, av integrin, Mesothelin, EGFR, TAG-72, GD2, CAIX, 5T4, a4ß7 integrin, Her2. Other targets are cytokines, such as interleukins IL-I through IL-13, tumour necrosis factors α & β, interferons α, β and γ, tumour growth factor Beta (TGF-β), colony stimulating factor (CSF) and granulocyte monocyte colony stimulating factor (GMCSF). See Human Cytokines: Handbook for Basic & Clinical Research (Aggrawal et al. eds., Blackwell Scientific, Boston, MA 1991). Other targets are hormones, enzymes, and intracellular and intercellular messengers, such as, adenyl cyclase, guanyl cyclase, and phospholipase C. Other targets of interest are leukocyte antigens, such as CD20, and CD33. Drugs may also be targets of interest. Target molecules can be human, mammalian or bacterial. Other targets are antigens, such as proteins, glycoproteins and carbohydrates from microbial pathogens, both viral and bacterial, and tumors. Still other targets are described in U.S. Pat. No. 4,366,241.

By "another disease" it is meant any other disease which is treatable by administration of an antibody. The other disease may be malignant ascites, in which case the antibody which is a treatment for the disease is typically catumaxomab or an antibody which binds to the same target as catumaxomab.

Whether it is a treatment for cancer or another disease, the antibody may be attached directly or indirectly to a cytotoxic moiety or to a detectable label. The antibody may be administered via one or more routes of administration using one or more of a variety of methods known in the art. The route and/or mode of administration will vary depending upon the desired results. Preferred routes of administration for antibodies include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection. Alternatively, an antibody can be administered via a non-parenteral route, such as a topical, epidermal or mucosal route of administration. Local administration is also preferred, including peritumoral, juxtatumoral, intratumoral, intralesional, perilesional, intra cavity infusion, intravesicle administration, and inhalation.

A suitable dosage of an antibody may be determined by a skilled medical practitioner. Actual dosage levels of an antibody may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular antibody employed, the route of administration, the time of administration, the rate of excretion of the antibody, the duration of the treatment, other drugs, compounds and/or materials used in combination with the particular compositions employed, the age, sex, weight, condition, general health and prior medical history of the patient being treated, and like factors well known in the medical arts.

A suitable dose of an antibody may be, for example, in the range of from about 0.1 µg/kg to about 100 mg/kg body weight of the patient to be treated. For example, a suitable dosage may be from about 1 µg/kg to about 10 mg/kg body weight per day or from about 10 µg/kg to about 5 mg/kg body weight per day.

Dosage regimens may be adjusted to provide the optimum desired response (e.g., a therapeutic response). For example, a single bolus may be administered, or step (b) of the method may comprise several divided doses administered over time or the dose may be proportionally reduced or increased as indicated by the exigencies of the therapeutic situation, provided the required interval between steps (a) and (b) is not exceeded. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

The antibody of step (b) may be administered in combination with chemotherapy or radiation therapy. The method may further comprises the administration of an additional anti-cancer antibody or other therapeutic agent, which may be administered together with the antibody of step (b) in a single composition or in separate compositions as part of a combined therapy. For example, the antibody of step (b) may be administered before, after or concurrently with the other agent.

The antibody may be Abagovomab, Abciximab, Actoxumab, Adalimumab, Adecatumumab, Afelimomab, Afutuzumab, Alacizumab pegol, ALD518, Alemtuzumab, Alirocumab, Altumomab pentetate, Amatuximab, Anatumomab mafenatox, Anrukinzumab, Apolizumab, Arcitumomab, Aselizumab, Atinumab, Atlizumab (=tocilizumab), Atorolimumab, Bapineuzumab, Basiliximab, Bavituximab, Bectumomab, Belimumab, Benralizumab, Bertilimumab, Besilesomab, Bevacizumab, Bezlotoxumab, Biciromab, Bimagrumab, Bivatuzumab mertansine, Blinatumomab, Blosozumab, Brentuximab vedotin, Briakinumab, Brodalumab, Canakinumab, Cantuzumab mertansine, Cantuzumab ravtansine, Caplacizumab, Capromab pendetide, Carlumab, Catumaxomab, CC49, Cedelizumab, Certolizumab pegol, Cetuximab, Ch.14.18, Citatuzumab bogatox, Cixutumumab, Clazakizumab, Clenoliximab, Clivatuzumab tetraxetan, Conatumumab, Concizumab, Crenezumab, CR6261, Dacetuzumab, Daclizumab, Dalotuzumab, Daratumomab, Demcizumab, Denosumab, Detumomab, Dorlimomab aritox, Drozitumab, Duligotumab, Dupilumab, Dusigitumab, Ecromeximab, Eculizumab, Edobacomab, Edrecolomab, Efalizumab, Efungumab, Elotuzumab Elsilimomab, Enavatuzumab, Enlimomab pegol, Enokizumab, Enoticumab, Ensituximab, Epitumomab cituxetan, Epratuzumab, Erlizumab, Ertumaxomab, Etaracizumab, Etrolizumab, Evolocumab, Exbivirumab, Fanolesomab, Faralimomab Farletuzumab, Fasinumab, FBTA05, Felvizumab, Fezakinumab, Ficlatuzumab, Figitumumab, Flanvotumab, Fontolizumab, Foralumab, Foravirumab, Fresolimumab, Fulranumab, Futuximab, Galiximab, Ganitumab, Gantenerumab, Gavilimomab, Gemtuzumab ozogamicin, Gevokizumab, Girentuximab, Glembatumumab vedotin, Golimumab, Gomiliximab, GS6624, Ibalizumab, Ibritumomab tiuxetan, Icrucumab, Igovomab, Imciromab, Imgatuzumab, Inclacumab, Indatuximab ravtansine, Infliximab, Intetumumab, Inolimomab, Inotuzumab ozogamicin, Ipilimumab, Iratumumab, Itolizumab, Ixekizumab, Keliximab, Labetuzumab, Lampalizumab, Lebrikizumab, Lemalesomab, Lerdelimumab, Lexatumumab, Libivirumab, Ligelizumab, Lintuzumab, Lirilumab, Lodelcizumab, Lorvotuzumab mertansine, Lucatumumab, Lumiliximab, Mapatumumab, Maslimomab, Mavrilimumab, Matuzumab, Mepolizumab, Metelimumab, Milatuzumab, Minretumomab, Mitumomab, Mogamulizumab, Morolimumab, Motavizumab, Moxetumomab pasudotox, Muromonab-CD3, Nacolomab tafenatox, Namilumab, Naptumomab estafenatox, Narnatumab, Natalizumab, Nebacumab, Necitumumab, Nerelimomab, Nesvacumab, Nimotuzumab, Nivolumab, Nofetumomab merpentan, Obinutuzumab, Ocaratuzumab, Ocrelizumab, Odulimomab, Ofatumumab, Olaratumab, Olokizumab, Omalizumab, Onartuzumab, Oportuzumab monatox, Oregovomab, Orticumab, Otelixizumab, Oxelumab, Ozanezumab, Ozoralizumab, Pagibaximab, Palivizumab, Panitumumab, Panobacumab, Parsatuzumab, Pascolizumab, Pateclizumab, Patritumab, Pemtumomab, Perakizumab, Pertuzumab, Pexelizumab, Pidilizumab, Pinatuzumab vedotin, Pintumomab, Placulumab, Polatuzumab vedotin, Ponezumab, Priliximab, Pritoxaximab, Pritumumab, PRO 140, Quilizumab, Racotumomab, Radretumab, Rafivirumab, Ramucirumab, Ranibizumab, Raxibacumab, Regavirumab, Reslizumab, Rilotumumab, Rituximab, Robatumumab, Roledumab, Romosozumab, Rontalizumab, Rovelizumab, Ruplizumab, Samalizumab, Sarilumab, Satumomab pendetide, Secukinumab, Seribantumab, Setoxaximab, Sevirumab, Sibrotuzumab, Sifalimumab, Siltuximab, Simtuzumab, Siplizumab, Sirukumab, Solanezumab, Solitomab, Sonepcizumab, Sontuzumab, Stamulumab, Sulesomab, Suvizumab, Tabalumab, Tacatuzumab tetraxetan, Tadocizumab, Talizumab, Tanezumab, Taplitumomab paptox, Tefibazumab, Telimomab aritox, Tenatumomab, Teneliximab, Teplizumab, Teprotumumab, TGN1412, Ticilimumab (=tremelimumab), Tildrakizumab, Tigatuzumab, TNX-650, Tocilizumab (=atlizumab), Toralizumab, Tositumomab, Tralokinumab, Trastuzumab, TRBS07, Tregalizumab, Tremelimumab Tucotuzumab celmoleukin, Tuvirumab, Ublituximab, Urelumab, Urtoxazumab, Ustekinumab, Vapaliximab, Vatelizumab, Vedolizumab, Veltuzumab, Vepalimomab Vesencumab, Visilizumab, Volociximab, Vorsetuzumab mafodotin, Votumumab, Zalutumumab, Zanolimumab, Zatuximab, Ziralimumab or Zolimomab aritox.

Preferred antibodies include Natalizumab, Vedolizumab, Belimumab, Atacicept, Alefacept, Otelixizumab, Teplizumab, Rituximab, Ofatumumab, Ocrelizumab, Epratuzumab, Alemtuzumab, Abatacept, Eculizumab, Omalizumab, Canakinumab, Meplizumab, Reslizumab, Tocilizumab, Ustekinumab, Briakinumab, Etanercept, Inlfliximab, Adalimumab, Certolizumab pegol, Golimumab, Trastuzumab, Gemtuzumab, Ozogamicin, Ibritumomab, Tiuxetan, Tostitumomab, Cetuximab, Bevacizumab, Panitumumab, Denosumab, Ipilimumab, Brentuximab and Vedotin.

Therapy

In another embodiment, the therapy is an organ transplant. The organ may be selected from kidney, liver, heart, pancreas, lung, or small intestine.

The subject to be treated may preferably be sensitized or highly sensitised. By "sensitized" it is meant that the subject has developed antibodies to human major histocompatibility (MHC) antigens (also referred to as human leukocyte antigens (HLA)). The anti-HLA antibodies originate from allogenically sensitized B-cells and are usually present in patients that have previously been sensitized by blood transfusion, previous transplantation or pregnancy (Jordan et al., 2003).

Whether or not a potential transplant recipient is sensitized may be determined by any suitable method. For example, a Panel Reactive Antibody (PRA) test may be used to determine if a recipient is sensitized. A PRA score >30% is typically taken to mean that the patient is "high immulogic risk" or "sensitized". Alternatively, a cross match test may be conducted, in which a sample of the potential transplant donor's blood is mixed with that of the intended recipient. A positive cross-match means that the recipient has antibodies which react to the donor sample, indicating that the recipient is sensitized and transplantation should not occur. Cross-match tests are typically conducted as a final check immediately prior to transplantation.

The presence of high titer antibodies against MHC antigens of the potential donor (i.e. donor specific antibodies (DSA)) is a direct contraindication to transplantation because of the risk of acute antibody-mediated rejection. In short, sensitization to donor MHC antigens hampers the identification of a suitable donor. A positive cross-match test is an unambiguous barrier to transplantation. Since approximately one third of patients waiting for kidney transplantation are sensitized, with as many as 15% being highly sensitized, this leads to an accumulation of patients waiting for transplant. In the US, the median time on the waiting list for renal transplantation in 2001-2002 was 1329 days for those with Panel Reactive Antibody (PRA) score 0-9%, 1920 days for those with PRA 10-79%, and 3649 days for those with PRA 80% or greater (OPTN-database, 2011).

One accepted strategy to overcome the DSA barrier is to apply plasma exchange or immune adsorption, often in combination with e.g. intravenous gamma globulin (IVIG) or Rituximab, to lower the levels of DSA to a level where transplantation can be considered (Jordan et al., 2004; Montgomery et al., 2000; Vo et al., 2008a; Vo et al., 2008b). However, plasma exchange, immune adsorption and IVIG treatments have the disadvantage of being inefficient and requiring rigorous planning since they involve repeated treatments over an extended period of time. When an organ from a deceased donor becomes available it has to be transplanted within hours since prolonged cold ischemia time is one of the most important risk factors for delayed graft function and allograft loss in renal transplantation (Ojo et al., 1997).

By contrast, the method of the present invention allows the rapid, temporary and safe removal of DSAs in a potential transplant recipient. Administering the agent just prior to transplantation has the capacity to effectively desensitize a highly sensitized patient, thereby allowing transplantation and avoiding acute antibody-mediated rejection. A single dose of agent prior to transplantation will enable transplantation of thousands of patients with donor specific IgG antibodies.

In the context of this embodiment, the method may be alternatively described as a method for the treatment of organ failure in a subject, the method comprising (a) administering to the subject an agent which reduces Fc receptor binding of serum IgG molecules in the subject; and (b) subsequently transplanting a replacement organ into the subject; wherein:

the amount of said agent administered is sufficient to eliminate Fc receptor binding by substantially all IgG molecules present in the serum of the subject; and steps (a) and (b) are separated by a time interval of at least 2 hours and at most 21 days.

This embodiment may be described as a method for preventing rejection of a transplanted organ in a subject, particularly acute antibody-mediated transplant rejection, the method comprising, at least 2 hours and at most 21 days prior to transplantation of the organ, administering to the subject an agent which reduces Fc receptor binding of serum IgG molecules in the subject, wherein the amount of said agent administered is sufficient to eliminate Fc receptor binding by substantially all IgG molecules present in the serum of the subject. It will be appreciated that administration of the agent and subsequent transplantation are separated by a time interval which is equivalent to the time interval between steps (a) and (b) in the alternative phrasings of the method presented above. Thus, the various upper and lower limits for the time interval between steps (a) and (b) described above apply equally to this time interval. In this embodiment it is particularly preferred that the time interval is short enough to allow the method to be conducted during a single hospital visit. Thus, preferred intervals are 1 to 6 hours or 1 to 12 hours.

The invention also provides use of the agent in such a method of treating organ failure or preventing transplant rejection, particularly acute antibody-mediated transplant rejection. The invention also provides use of the agent in the manufacture of a medicament for the treatment of organ failure or for the prevention of transplant rejection by such a method.

In this embodiment, the method of the invention may additionally comprise a step conducted at or immediately prior to transplantation, which step comprises induction suppression of T cells and/or B cells in the patient. Said induction suppression may typically comprise administering an effective amount of an agent which kills or inhibits T cells, and/or administering an effective amount of an agent which kills or inhibits B cells. Agents which kill or inhibit T cells include Muromonab, Basiliximab, Daclizumab, an antithymocyte globulin (ATG) antibody and a lymphocyte immune globulin, anti-thymocyte globulin preparation (AT-GAM). Rituximab is known to kill or inhibit B cells.

Method for Removing Antibodies or Reducing the Effect of Antibodies in a Subject The invention also provides a method for removing antibodies or reducing the effects of antibodies in a subject. The antibodies to be affected by the method are typically pathogenic autoantibodies. The method comprises a first step, referred to as step (a) and an optional second step, referred to as step (b).

Step (a) comprises administering to the subject an agent which reduces Fc receptor binding of serum IgG molecules in the subject. The amount of the agent administered is preferably sufficient to eliminate Fc receptor binding by substantially all IgG molecules present in the serum of the subject.

If conducted, step (b) comprises, subsequent to step (a), subjecting the subject to a treatment which removes endogenous antibodies; wherein said treatment which removes endogenous antibodies is plasmapharesis or immunoadsoprtion, or is administration of an agent (such as an anti-FcRn antibody) which prevents recycling of antibodies in serum by the FcRn receptor, thereby reducing half-life, and wherein steps (a) and (b) are separated by a time interval of at least 2 weeks.

The method may further comprise repeating step (a). Step (a) is preferably only repeated if the patient has a low level of anti-agent antibody responses. The quantity of anti-agent IgG molecules in the serum of a patient may be determined by any suitable method, such as an agent specific CAP FEIA (ImmunoCAP) test. A repetition of step (a) would only be conducted if the result of the CAP FEIA is below a threshold to be determined by the clinician. Typically, to avoid the development of an excessive anti-agent response, step (a) should be repeated no more frequently than once every 6 months.

The affected by the method may typically pathogenic autoantibodies specific for an auto-antigen which is targeted in an autoimmune disease mediated wholly or in part by autoantibodies. Table 3 sets out a list of such diseases and the associated autoantigens.

TABLE 3

| DISEASE | AUTOANTIGENS |
|---|---|
| Addison's disease | Steroid 21-hydroxylase, 17 alpha-Hydroxylase (17OH) and side-chain-cleavage enzyme (P450scc), Thyroperoxidase, thyroglobulin and H+/K(+)- |
| Anti-GBM glomerulonephritis (related to Goodpasteur) | Anti-glomerular basement membrane (anti-GBM): noncollagenous (NC1) domains of the alpha3alpha4alpha5(IV) collagen |
| Anti-neutrophil cytoplasmic antibody-associated vasculitides (ANCA associated vasculitis)(Wegener granulomatosis, Churg-Strauss syndrome, microscopic polyangiitis) | Myeloperoxidase, proteinase 3 |
| Anti-phospholipid antibody syndrome (APS) | Negatively-charged phospholipids complexed with phospholipid binding plasma proteins (e.g. beta2GPI), cardiolipin, beta2-glycoprotein I, and (beta2GPI) |

TABLE 3-continued

| DISEASE | AUTOANTIGENS |
|---|---|
| Autoimmune bullous skin diseases (Pemphigus). Pemphigus foliaceus (PF), fogo selvagem (FS)(endemic form), pemphigus vulgaris (PV) | IgG against keratinocytes. Specific target is desmoglein (Dsg) 1 (desmosomal Cadherins) |
| Autoimmune hemolytic anemia (AIHA) | Self-antigens on red-blood-cells |
| Autoimmune hepatitis (AIH) | Actin, antinuclear antibody (ANA), smooth muscle antibody (SMA), liver/kidney microsomal antibody (LKM-1), anti soluble liver antigen (SLA/LP) and anti-mitochondrial antibody (AMA), CYP2D6, CYP2C9-tienilic acid, UGTIA, CYP1A2, CYP2A6, CYP3A, CYP2E1, CYP11A1, CYP17 and CYP21 |
| Autoimmune neutropenia (AIN) | FcgRIIIb |
| Bullous pemphigoid (BP) | Hemidesmosomal proteins BP230 and BP180 (type XVII collagen), laminin 5, the alpha6 subunit of the integrin alpha6beta4 and p200 |
| Celiac disease | transglutaminase 2 (TG2), transglutaminase 3, actin, ganglioside, collagen, calreticulin and zonulin, thyroid, endocrine pancreas, anti-gastric and liver, anti-nuclear constituents, anti-reticulin, actin, smooth muscle, calreticulin, desmin, collagens, bone, anti-brain, ganglioside, neuronal, blood vessel |
| Chronic utricaria | Alpha-subunit of the high-affinity IgE receptor, IgE |
| Complete congenital heart block (CCHB) | Ro (Sjögens syndrome antigen A (SSA)), La (Sjögens syndrome antigen B(SSB)) |
| Diabetes type 1A (TIDM) | Islet cell autoantibodies (ICA), antibodies to insulin (IAA), glutamic acid decarboxylase (GAA or GAD), protein tyrosine phosphatase (IA2 or ICA512), Insulinoma Associated Peptide-2. The number of antibodies, rather than the individual antibody. is thought to be most predictive of progression to overt diabetes. |
| Essential mixed cryoglobulinemia | Essential mixed cryoglobulinemia antigens |
| Goodpasture's syndrome (also known as Goodpasture's disease and anti-glomerular basement membrane disease | alpha3(IV) collagen (=Goodpasture antigen) |
| Graves' disease (Basedow's disease), includes Goitre and hyperthyroidism, infiltrative exopthalmos and infiltarative dermopathy. | Thyrotropin receptor (TSHR) Thyroid peroxidase (TPO) |
| Guillain-Barré syndrome (GBS). Acute inflammatory demyelinating polyneuropathy (AIDP), acute motor axonal neuropathy (AMAN) | Gangliosides GMI, GM1b, GDla, and GalNAc-GDla, glycosphingolipid, myelin proteins PMP22 and PO |
| Hemophilia-Acquired FVIII deficiency | Factor VIII |
| Idiopathic thrombocytopenia purpura (ITP) | Platelet glycoprotein (GP) IIb-IIIa and/or GPIb-IX |
| Lambert-Eaton myasthenic syndrome (LEMS) | voltage gated calcium channels |
| Mixed Connective Tissue Disease (MCTD) | IgG directed against the spliceosome, U1-snRNP |
| Multiple Myeloma | Multiple Myeloma antigens |
| Myasthenia gravis | Acetylcholine receptors (AchR), muscle-specific kinase (MuSK) |
| Myocarditis, dilated cardiomyopathy (DCM)(congestive cardiomyopathy) | heart-reactive autoantibodies against multiple antigens e.g. cardiac myosin |
| Primary biliary cirrhosis (PBC) | pyruvate dehydrogenase complex (PDC)-E2 and other members of the oxaloacid dehydrogenase family, Glycoprotein-210, p62, sp100 |
| Primary Progressive Multiple Sclerosis (PPMS) | Myelin oligodendrocyte glycoprotein (MOG),Myelin proteolipid protein (PLP), transketolase (TK), cyclic nucleotide phosphodiesterase type 1 (CNPase I), collapsin response mediator protein 2, tubulin beta4, neurofascin |
| Rheumatic heart disease (RHD),(Rheumatic fever) | Cardiac myosin |
| Rheumatoid Arthritis (RA) | Type II collagen, citrullin (-ated proteins (e.g. (fibrinogen, vimentin, filaggrin, type II collagen, enolase)), G6PI, RFs (anti-Fc/IgG), Vimentin, and cytokeratin |
| Sjögren Syndrome (SS) | Ro (Sjögens syndrome antigen A (SS-A)), La (Sjögens syndrome antigen B(SS-B)), p80 coilin, antinuclear antibodies, anti-thyroid, anti-centromere antibodies (Raynaud's phenomenon), anti-carbonic anhydrase II (distal renal tubular acidosis), anti-mitochondrial antibodies (liver pathology), cryoglobulins (evolution to non-Hodgkin's lymphoma). alpha-and beta-fodrin, islet cell autoantigen, poly(ADP)ribose polymerase (PARP), NuMA, Golgins, NOR-90, M3-muscarinic receptor |

TABLE 3-continued

| DISEASE | AUTOANTIGENS |
|---|---|
| SLE including Lupus nephritis | Autoantibodies to nuclear constituents (e.g. dsDNA and nucleosomes), dsDNA, PARP, Sm, PCDA, rRNA Ribosome P proteins, Clq |
| Stiff-person syndrome (SPS) | glutamic acid decarboxylase (GAD), amphiphysin. |
| Systemic sclerosis (scleroderma) | DNA-topoisomerase I (Scl-70), U3 snRNP, U2 snRNP, 7-2 RNP, NOR-90, centromere-associated proteins, and nucleolar antigens, Anti-Th/To, Anti-RNA polymerase I/III, Anti-PDGF receptor, Anti-fibrillin-1, M3-muscarinic receptor, |
| Transplant rejection | Transplant rejection antigens |

Substitute Specification-Clean Copy

In this embodiment, the method may be alternatively described as a method for the treatment of an autoimmune disease in a subject, the method comprising (a) administering to the subject an agent which reduces Fc receptor binding of serum IgG molecules in the subject; and optionally (b) subsequently administering to the subject a therapeutically effective amount of an antibody which is a treatment for said cancer or autoimmune disease; wherein the amount of said agent administered is sufficient to eliminate Fc receptor binding by substantially all IgG molecules present in the serum of the subject; and steps (a) and (b) are separated by a time interval of at least 2 hours and at most 21 days. The invention also provides the agent for use in such a method for the treatment of autoimmune disease. The invention also provides use of the agent in the manufacture of a medicament for the treatment of autoimmune disease by such a method.

The autoimmune disease is preferably a chronic autoimmune disease which is mediated wholly or in part by autoantibodies. The autoimmune disease may be one of the diseases listed in Table 3.

Optional Additional Method Step

In the methods of the invention, the agent administered in step (a) typically does not act only on serum IgG molecules. The inventors have also made the surprising discovery that the agent may also act upon membrane bound IgG molecules which are present as part of a B cell receptor complex (BCR).

The BCR contains one ligand binding and one signalling part. The ligand-binding part consists of an antibody with a transmembrane domain and the signalling part consists of a heterodimer called Ig-α/Ig-β (CD79a/CD79b). The CD79 proteins span the plasma membrane and have a cytoplasmic tail bearing an immunoreceptor tyrosine-based activation motif (ITAM). Upon receptor ligation ITAM is phosphorylated by the SRC family kinase LYN and recruits the spleen tyrosine kinase (SYK) to the receptor. Activation of SYK leads to formation of a plasma membrane-associated signalling complex, named signalosome, which assembles signalling molecules, such as phospholipase-Cγ2 (PLC γ2), (phosphoinositide 3-kinase (PI3K), Bruton's tyrosine kinase (BTK), VAV1 and adaptor molecules. Two fundamental and intensively studied intermediates in the BCR signalling cascades, PLC γ2 and PI3K, generate key second messengers, which in turn, activate IκB kinase (IKK) and extracellular-signal regulated kinases (ERK1/2; AKA MAPK3 and 1). B-cell fate decisions i.e. proliferation, survival, differentiation and cell death are closely regulated by the balance between these signalling events. During B-cell development, naïve mature B-cells leave the bone marrow, go through somatic hyper mutation in germinal centres and class switching before becoming high affinity long-lived plasma cells and memory B-cells ready to respond heavily when activated by antigenic stimulation. Memory B-cells respond to antigen through binding to the BCR and a substantial portion of memory B-cells in circulation have an IgG-type of BCR.

Thus, the agent administered in step (a) of a method of the invention may also act upon the IgG part of the BCR of memory B-cells and may inhibit the normal activation of these cells by ligand binding. As a result, there will be an interval in which activation of memory B cells in the individual is reduced. This interval typically ends at around 12 hours after completion of step (a), but may be longer. At the end of the interval, levels of intact membrane bound IgG (and thus normal BCR) have recovered, typically as a result of membrane turnover in the affected cell. Subsequently, there is then a further interval at the end of which newly-synthesised IgG starts to re-appear in serum. This interval typically ends around 3-4 days after completion of step (a).

The action on memory B cells of the agent administered in step (a) of the methods of the invention therefore provides the opportunity to include an optional additional step in any method of the invention. This step, referred to as step (a1), is conducted after step (a) and, if step (b) is present, before step (b) in a method of the invention. Step (b) will then typically be conducted as soon as is possible or practical after step (a1). Step (a1) may be conducted (i) in the interval after step (a) but before the recovery of levels of intact membrane bound IgG on cell surfaces in the subject, or (ii) in the interval after (i) but before newly-synthesised IgG starts to re-appear in serum of the subject. The recovery of the level of intact membrane-bound IgG or the re-appearance of serum IgG may be determined by any suitable method. Exemplary methods are described in the Examples.

The interval of (i) typically ends at around 12 hours, 16 hours or 24 hours after step (a). Therefore if step (a1) is conducted in interval (i), it may be conducted at up to 1 hour, 2 hours, 3 hours, 4 hours, 5 hours, 6 hours, 7 hours, 8 hours, 9 hours, 10 hours, 11 hours, 12 hours, 16 hours or 24 hours after step (a), preferably at up to 1 or 2 hours after step (a).

The interval of (ii) starts at the end of the interval of (i) and typically ends 3 or 4 days. after step (a). Thus, the interval of (ii) is thus typically at most from 12 hours to 4 days (96 hours) after step (a). Therefore if step (a1) is conducted in interval (ii) it is conducted between 12 hours and 96 hours after step (a1), and may be conducted between 12 hours and 24 hours, between 12 hours and 48 hours, or between 12 hours and 72 hours after step (a). For the convenience of the subject, it is generally preferable to conduct step (a1) as soon as possible within interval (ii). Thus, conducting step (a1) between 12 hours and 24 hours after step (a) is preferred.

If step (a1) is conducted in interval (i), it typically comprises administration of an agent which specifically targets an epitope present on the IgG or IgG fragment which results from the action on a B cell of the agent of step (a). For example, step (a1) may comprise administration of an agent which specifically binds to a membrane bound Fc fragment (such as that produced by the action of IdeS) or which specifically binds to a membrane bound IgG with altered glycosylation (such as that produced by the action of EndoS). The epitope may be newly created by the action of the agent of step (a), or may be an epitope which is already present in intact IgG, provided that it is retained by the IgG or IgG fragment which results from the action of the agent of step (a).

In other words, the invention may also provide a method in which an additional step (a1) is conducted after step (a) and, if step (b) is present, before step (b), wherein step (a1) comprises administering to the subject an agent which specifically binds to an epitope produced by the action of the agent administered in step (a) on membrane-bound IgG in the BCR complex, wherein said administering is conducted in an interval after step (a) but before the level of intact membrane-bound IgG in BCR complexes has recovered to the same level as was present before step (a). That is interval (i) as described above. The epitope may be, for example, a membrane-bound Fc fragment (such as that produced by the action of IdeS). The agent administered in step (a1) of said method may be any agent which specifically binds to the epitope, such as an antibody. Binding of the agent will typically result in reduced activation and/or death of a cell upon which the target is present. Said cell is typically a memory B cell. The agent may optionally be conjugated to a cytotoxin (suitable examples include those listed in Table 4), radioisotope or other moiety to promote said reduced activation or death of said cell. Thus, in this embodiment, administration of an agent in step (a1) typically results in death of memory B cells which display an IgG molecule which has been altered by the action of the agent of step (a). Thus the inclusion of step (a1) may increase the beneficial effects of a method of the invention, for example by prolonging or maintaining the absence of serum IgG molecules.

recovered an intact BCR. Alternatively the agent may be used to target the specific Fab region of the BCR of memory B cells which are specific for a particular antigen, that is the agent administered in step (a1) may be anti-idiotypic. For example, the agent administered in step (a1) may be used to target the Fab region of donor specific antibodies in a transplant recipient, or the Fab region of antibodies specific for autoimmune antigens in an autoimmune patient, such as a patient suffering from a disorder as listed in Table 3.

In other words, the invention may also provide a method in which an additional step (a1) is conducted after step (a) and before step (b) if step (b) is present, wherein step (a1) comprises administering to the subject an agent which specifically binds to an epitope of intact, membrane-bound IgG, wherein said administering is conducted in the interval after step (a) in which the level of intact membrane-bound IgG in BCR complexes has returned to a level similar to, substantially the same as, or the same as the level that as was present before step (a), but newly-synthesised IgG has not yet re-appeared in serum. That is interval (ii) as described above. The agent administered in step (a1) of said method may be any agent which specifically binds to the epitope, such as an antibody. Binding of the agent will typically result in reduced activation and/or death of a cell upon which the target is present. The agent may optionally be conjugated to a cytotoxin (suitable examples include those listed in Table 4), radioisotope or other moiety to promote said reduced activation or death of said cell. In this embodiment, administration of an agent in step (a1) may result in the death of all memory B cells which display an intact membrane bound IgG molecule. Alternatively it may result in the death only of memory B cells which display a particular specificity of membrane bound IgG molecule. In either case, the inclusion of step (a1) may increase the beneficial effects of a method of the invention, for example by prolonging or maintaining the absence of all serum IgG molecules, or prolonging or maintaining the absence of a specific sub-set of serum IgG molecules specific for a particular target. The latter may be particularly advantageous in that it will allow

TABLE 4

| Name | Target | Mode of action |
|---|---|---|
| Doxorubicinderivatives | Topoisomerase II DNA complexes | Inhibit DNA religation, leading to DNA double-strand breaks |
| Maytansinoids | α-Tubulin | Prevent tubulin polymerization |
| Auristatins | α-Tubulin | Prevent tubulin polymerization |
| Calicheamicins | Sequence-specific minor groove of DNA | Cause double-strand DNA breaks |
| CC-1065 | Sequence-specific minor groove of DNA | Induces adenine alkylation |
| Duocarmycins | Bind to specific minor groove of DNA | Break down adenine-specific molecules in the DNA structure |
| Anthracyclines | DNA, RNA complexes | Inhibit DNA and RNA synthesis by intercalating between base pairs, preventing replications |

If step (a1) is conducted in interval (ii), it typically comprises administration of an agent which specifically targets intact membrane bound IgG. Said agent will only affect memory B cells for which levels of membrane bound IgG in the BCR complex have recovered. Within this interval, all other forms of intact IgG (e.g. circulating IgG or IgG bound to effector cells by Fc receptors in the cell membrane) will have been removed by the action of the agent administered in step (a) and the resulting fragments will have been cleared. Thus, the agent administered in step (a1) may be used to target all memory B cells which have for the selective removal of unwanted subsets of IgG molecules from the newly-synthesised population of IgG in the serum of the subject to which the method of the invention is applied.

Kit

The invention also provides a kit suitable for use in a method of the invention, the kit containing an amount of an agent which reduces Fc receptor binding of serum IgG molecules in a subject, which amount is sufficient to eliminate Fc receptor binding by all or substantially all IgG molecules present in the serum of a subject.

The kits of the invention may additionally comprise one or more other reagents or instruments which enable any of the embodiments mentioned above to be carried out. Such reagents or instruments include one or more of the following: a therapeutically effective amount of a therapeutic agent, which is an antibody, suitable buffer(s) (aqueous solutions), means to administer the agent to a subject as an intravenous infusion (such as a vessel or an instrument comprising a needle). Reagents may be present in the kit in a dry state such that a fluid sample resuspends the reagents. The kit may also, optionally, comprise instructions to enable the kit to be used in the method of the invention or details regarding which patients the method may be used for.

The following Examples illustrate the invention.

EXAMPLE 1

Pre-Clinical Study

GLP-compliant pre-clinical investigations designed to investigate toxicology and pharmacology in New Zealand White rabbit of a GMP-produced IdeS demonstrated that IdeS cleaved the complete plasma pool of IgG within 5 minutes upon IdeS administration with <1% remaining IgG one day after treatment. The IgG level reached its lowest level 24-48 hours after IdeS-treatment and then gradually increased during the following days. Normal IgG levels were restored approximately 3 weeks after a single IdeS dose. The end-products, i.e. the $F(ab')_2$- and Fc-fragments, had significantly shorter half-lives compared to intact IgG and only low levels were detectable the day after a single dose of IdeS. IdeS had a rapid distribution, showed dose:proportional pharmacokinetics and a multi-phase elimination with a plasma half-life of approximately 1 hour in rabbits. Based on repeat dose toxicology studies the No Observed Adverse Effect Level (NOAEL) for IdeS was set to 2 mg/kg body weight (BW). Data not shown.

The effect of IdeS in the above in vitro and in vivo experiments was dramatic and provided the basis for the further investigation in healthy human volunteers.

Human Study

Materials and Methods

Study Design

This was a double-blind, randomized, single-center trial in healthy, male subjects (EudraCT number: 2012-000969-21) conducted in the Phase One unit at the University Hospital in Lund, Sweden. The protocol was approved by the local ethics committee prior to recruitment and all subjects provided signed informed consent before undergoing any study-specific procedures. The primary objective was to assess the safety and tolerability of IdeS following intravenous administration of single ascending doses. Secondary objectives were to evaluate IdeS efficacy (i.e. reduction in serum IgG), pharmacokinetics, and immunogenicity in healthy human subjects.

The diluted infusion solution of the GMP-produced IdeS (Hansa Medical AB, Sweden) was prepared in a phosphate buffered isotonic salt solution by the hospital pharmacy in an infusion syringe with an infusion set including a 0.2 µm filter (B. Braun, Germany). The selected starting dose of 0.010 mg/kg BW was 10-times below the pre-clinically determined Minimal Anticipated Biological Effect Level (MABEL) and 200-times below the No Observed Adverse Effect Level (NOAEL) determined during animal toxicology. The study design allowed gradual escalation of the dose with intensive safety monitoring.

To meet the inclusion criteria the subjects had to be healthy according to the screening medical examination, aged 18-45 years, have suitable veins for cannulation, a body mass index (BMI) between 19 and 30 kg/m² and weigh 50-100 kg. Subjects excluded from the study were those who had (or had a history of) any clinically significant immunodeficiency including but not limited to immunoglobulin A deficiency, had elevated levels of anti-IdeS IgG (>15 mg/L), tested positive for serum hepatitis B surface antigen, hepatitis C antibody, human immunodeficiency virus (HIV), ongoing tuberculosis, ongoing syphilis, active herpes simplex or herpes zoster infection during screening.

Each subject had a three days admission period at the Clinical Trials Unit and was randomized to IdeS or placebo (phosphate buffered saline) and dosed the morning after admission. Two subjects in each dose group were dosed on the first day (one IdeS and one placebo) and the next subjects in the group were dosed after one week. After each cohort the Data Monitoring Committee assessed the safety data and decided the next dose level. The time from the last dose at one dose level to the initiation of next dose level was at least 14 days. The infusions were given during 30 minutes for the first two subjects in each group and during 15 minutes for subsequent subjects in that group. During the admission period intensive safety monitoring and serial blood samplings for safety, pharmacokinetics, efficacy and anti-drug antibodies were performed. The subjects were discharged on day 4 and conducted at least eight intermediate follow-up visits with medical examination and blood sampling until the end of study at day 64.

All subjects participating in the study were treated with antibiotics (Spektramox if not hypersensitive to beta-lactams) as prophylaxis against bacterial infections. Prophylaxis treatment started on the dosing day and continued until plasma IgG levels were >4.5 g/L. No other concomitant medication or therapy was allowed except paracetamol during the first 28 days following dosing unless prescribed by the investigator and considered necessary for the subject's safety and well-being.

Safety Assessments

Adverse events (AE) were collected from the time of admission and throughout the study period including the follow-up period. All information about an AE was recorded including description, start/stop time, common Toxicity Criteria grade (according to CTCAE), severity, causality (unlikely, possible or probable), action taken, discontinuation and outcome. Vital signs, body temperature, heart rate and supine blood pressure were recorded regularly during the admission period and at all subsequent visits. In addition, the subjects were monitored with a 5-lead telemetric ECG during the infusion and the following 24 hours. Safety samples for clinical chemistry, hematology, coagulation, safety biomarkers (IL-6, IL-8 and TNFα) and plasma IgG were analyzed using routine methods at Labmedicin Skåne, Sweden. Urinalysis (U-glucose, U-hemoglobin and U-protein) was assessed using Multistix (Siemens, Germany).

Serum Samples for Efficacy, Pharmacokinetics and Anti-IdeS Antibody Evaluation

Blood samples intended for efficacy studies were collected in modified CAT serum BD vacutainers (BD Diagnostics, NJ, USA) containing 2 mM iodoacetic acid in order to prevent further proteolytic cleavage by IdeS. Blood sampling was performed at the following time-points: pre-dose, 1 minute before end of infusion (14 or 29 min), 5 minutes after end of infusion (20 or 35 min) and 45 minutes after end of infusion (1 h or 1 h and 15 min). In addition samples were collected 2, 6, 24, 48 and 72 hours after start of infusion as well as on day 7, 14, 21, 28 and 64 after infusion. Blood samples intended for pharmacokinetic studies were collected in regular . . . serum BD vacutainers at the following time-points: pre-dose, 1 minute before end of infusion, 5 minutes after end of infusion, 45 min after end of infusion and 2, 6, 24, 48, 72 and 144 hours after dosing. Blood samples intended for anti-IdeS antibody analysis were collected in regular serum BD vacutainers at day 1 (pre-dose), 2 (24 h), 3 (48 h), 4 (72 h), 7 (1 week), 14, (2 weeks), 21 (3 weeks), 28 (4 weeks) and 64 (2 months). Outside the study protocol the subjects were asked for optional serum samples on day 182 (6 months) and 365 (1 year). All samples were stored below −60° C. until analyzed.

Efficacy Assessment

IdeS cleavage and processing of IgG was investigated with different methods; Enzyme-linked immune-sorbent assays (ELISAs) were used to determine IgG and IgG fragments in serum and to investigate the dynamics of the Fab- and Fc-containing fragments. The quantitative assays could not completely differentiate between the IdeS cleavage products; i.e. $F(ab')_2$, Fc and single cleaved IgG (scIgG) (where one of the heavy chains is cleaved). The ELISA developed and performed by Covance Ltd, UK, measured intact IgG and scIgG. The Fab-ELISA measured all Fab-containing IgG fragments; i.e. intact IgG, scIgG and $F(ab')_2$ and the Fc-ELISA measured all Fc containing fragments; i.e. intact IgG, scIgG and free Fc.

The assay performed by Covance Ltd, UK, was formally validated. Briefly, serum samples were analyzed by an ELISA where IgG was allowed to bind to the catcher antibody, goat anti-human IgG $F(ab')_2$ (#109-006-097, Jackson ImmunoResearch Labs Inc., PA, USA). Quantified human serum protein calibrator (IgG) (X0908, Dako, Denmark) was used for preparation of standards and quality samples. Bound IgG was detected by the subsequent addition of peroxidase-conjugated $F(ab')_2$ fragment goat anti-human IgG, Fcγ fragment specific (#109-036-098, Jackson ImmunoResearch Labs) and a chromogenic substrate (TMB). The lower limit of quantification was 5 ng/mL (in 100% serum). The serum analyses were performed at Covance Laboratories Limited (Harrogate, UK).

The Fc-ELISA used a goat anti-human IgG (Fcγ fragment specific) $F(ab')_2$ fragment (#109-006-098 Jackson ImmunoResearch Labs Inc., PA, USA) as catcher antibody and a biotin conjugated goat anti-human IgG (Fcγ fragment specific) $F(ab')_2$ fragment (#109 066 098 Jackson ImmunoResearch) as detector. In the Fab-ELISA an affinity purified mouse anti-human IgG, $F(ab')_2$ fragment specific antibody (#209-005-097 Jackson ImmunoResearch Labs Inc., PA, USA) was used as catcher antibody and biotinylated CaptureSelect IgG-CH1 (#710.3120.100 BAC B.V., Naarden, Netherlands) as detector. A streptavidin-horseradish peroxidase conjugate (SA-HRP) (#21126 Pierce, Thermo Fisher Scientific, Rockford, IL) was used for secondary detection. Calibrator and QC-samples (ULOQ, LLOQ, H-OC, M-QC and L-QC) were prepared from human intravenous gamma globulin IVIg (Octagam®). All dilutions were performed in PBS +0.1% BSA and the Nunc MaxiSorp® flat-bottom 96-well microtiter plates (Nunc A/S, Roskilde, Denmark) were washed with PBS containing 0.05% Tween 20. The serum samples and QC-samples were analyzed in triplicates. TMB One component HRP Microwell substrate (TMBW-1000-01, BioFx Laboratories Inc., MD, USA) was used as a chromogenic substrate and the enzyme reaction was stopped by the addition of 0.5 M $H_2SO_4$. The absorbance was measured in an ELISA plate reader (Multiscan EX, Thermo Electron Corp.) (Software: Ascent Software v. 2.6) at $\lambda$=450 nm.

Figure 19:
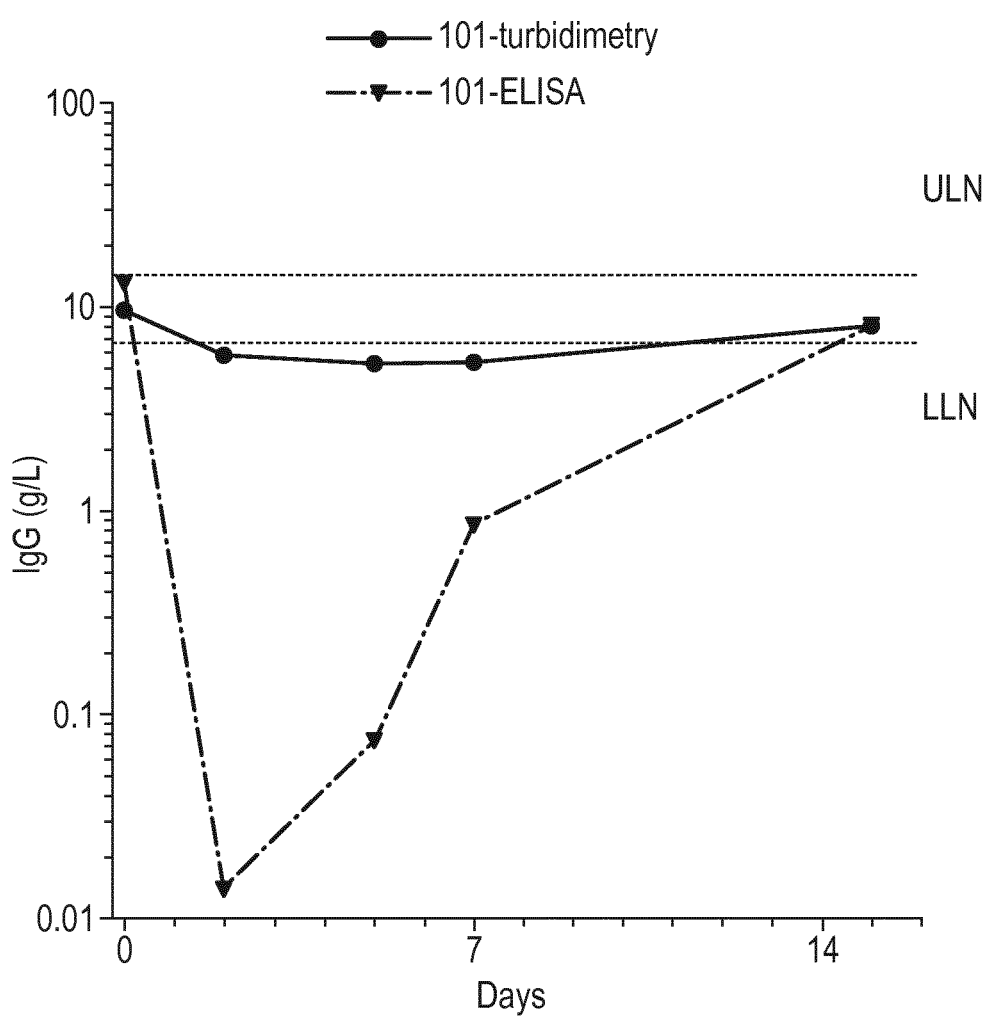
FIG. 19 shows a comparison of two methods for measuring IgG levels (turbidimetry and PD-ELISA) in serum from a subject (#101) treated with IdeS. Serum was collected at different time point post dosing with IdeS and measured using the standard p-IgG turbidimetry test at the hospital and using the PD-ELISA assay developed by the inventors to discriminate between intact IgG and F(ab')$_2$-fragments generated upon IdeS cleaving IgG. ULN=upper limit of normality and LLN=lower limit of normality for IgG in human healthy subjects.

A comparison of the Fab-ELISA and a conventional turbidimetric analysis of serum IgG is shown in FIG. 19. As is shown, the turdidimetric assay detects only a small change in the level of intact IgG over time following IdeS treatment, because it cannot discriminate between $F(ab')_2$ and intact IgG. By contrast, the Fab-ELISA shows almost complete removal and recovery of IgG levels in the same time period.

In order to further evaluate the quantitative data from the ELISA, the serum samples were also analyzed using qualitative SDS-PAGE analyses. The SDS-PAGE analyses were performed according to the manufacturer's instructions (Bio-Rad Laboratories, CA, USA). Briefly, 0.25 µl of serum was separated on 4-20% Mini-PROTEAN®TGX™ precast gels (BioRad) at 200 V for 40 minutes under non-reduced conditions. SeeBlue MW standard (Life Technologies) and an in house prepared mix of human IgG, scIgG, $F(ab')_2$ and Fc were used as markers. The gels were stained with GelCode Blue stain reagent (Pierce, Thermo Fisher Scientific, MA, USA) according to the manufacturer's instructions and the gels were scanned.

Pharmacokinetics Assessment

Four IdeS derived peptides, i.e. AFPYLSTK, AIYVTDSDSNASIGMK, GGIFDAVFTR and LFEYFK, were assayed in serum samples by a qualified LC-MS/MS assay (Karlsson et al. 2012). Samples were prepared for MS analysis as previously described (Karlsson et al. 2012). The selected reaction monitoring (SRM) measurements were performed on a TSQ Vantage triple quadrupole mass spectrometer (Thermo Fisher Scientific, MA, USA) equipped with a PicoChip column packed with Reprosil-PUR C18 (New Objective, MA, USA) and a Easy-nLC II system (Thermo Fisher Scientific). The raw data was processed and analyzed with SRM analysis software Skyline (MacLean et al. 2010) with manual validation and inspection of the results. The injection volume was 1 µl corresponding to 12.5 nl serum (i.e. 1 µg total protein). Un-normalized peptide Total Peak Areas from IdeS-spiked serum was used for fitting a linear regression curve (label-free protein quantification). The concentrations of the individual peptides in the unknown human samples were interpolated from the linear regression. A commercial equimolar mixture of tryptic peptides from 6 bovine proteins (6 Bovine Tryptic Digest Equal Molar Mix, Michrom Bioresources) was used as QC-sample and run every 4-6 analytical sample (Teleman et al. 2012).

Serum concentration versus time data was analysed by non-compartmental analysis (NCA) in Phoenix™ WinNonlin® version 6.3, build 6.2.0.495 (Pharsight®, St. Louis, Missouri, USA). As no major deviations (>20%) between nominal and actual sampling times and doses were observed, nominal sampling times and doses were used for the NCA calculations. The LC-MS/MS assay has not been validated and no formal lowest limit of detection (LLOQ) has been defined. A cut off for the PK calculations was set to 24 hours post dose for all four peptides and individuals.

Anti-IdeS IgG Assessment

A CAP-FEIA (ImmunoCAP) test for quantification of anti-IdeS specific IgG was developed by Thermo Fisher Scientific (Phadia®) in Uppsala, Sweden. Initial testing indicated that a 3-logaritmic measuring range was possible using the test and the limit of detection (LOD) for the IgG IdeS-specific CAP-FEIA assay was shown to be seven times below the suggested low assay cut-off (i.e. 2.0 mg/L). Analyses of the clinical samples were performed on a Phadia® 250 instrument using the test with one replicate according to the Phadia® 250 user manual. The test was intended for research use only.

Antigen-Specific Efficacy

A research grade ELISA assay was developed at Hansa Medical AB in order to address antigen-specific efficacy at the end of the study. The subjects IgG-response against a vaccine included in the Swedish childhood vaccination schedule was utilized as a surrogate for lack of auto-antigens in the healthy subjects included in the phase 1 study. Briefly, DTaP-IPV//PRP~T vaccine (Pentavac®/Pentaxim®)-Sanofi Pasteur) was diluted 100-times in PBS prior to coating MaxiSorp plates (Nunc) at 4° C. Normal human IgG (IVIg, Octagam®) was utilized as calibrator and a goat anti-human Fc-specific biotin-SP-conjugated $F(ab')_2$ (Jackson #109-066-098) as detector. Furthermore, SA-HRP (Pierce #21126) was used and the signals were developed with TMB One component HRP Microwell Substrate (BioFX Laboratories #TMBW-1000-01), stopped with 0.5M $H_2SO_4$ and read at 450 nm.

Functional In Vitro Assay

A phagocytosis assay was developed with modifications from (Ackerman et al., 2011). Fluorescent neutravidin beads (#F8776, Molecular Probes) were coated over night with biotinylated anti-IgG CH1 (CaptureSelect, #710.3120.100 BAC B.V., Naarden, Netherlands) at 0.1 mg/ml. The CaptureSelect reagent is specific for human heavy chain IgG on the CH1 domain i.e. intact IgG, scIgG and $F(ab')_2$ fragments but not IgM will be captured by this protein. Coated beads were washed and mixed with 1:100 diluted serum from study subjects and incubated at 37° C. for 2 hours to allow IgG in serum to bind to the coated beads. A control was prepared by mixing coated beads with dilution buffer (PBS with 0.1% BSA). All samples were prepared in duplicate. After incubation, IgG-loaded beads were washed and mixed with 75 000 THP-1 cells/sample and incubated in a $CO_2$-incubator at 37° C. for 1.5-3 hours. After incubation samples were fixed in ice-cold 2% phosphate buffered formalin and the fluorescent uptake in THP-1 cells was monitored using an Accuri C6 flow cytometer.

Statistical Analysis

Means, medians, standard deviations, and basic statistical analysis were performed using the GraphPad Prism 6 software (GraphPad Software, CA, USA).

Results

Study Description

A phase I, first in man, randomized double-blind study with single ascending doses of IdeS was conducted after approval from Swedish regulatory and ethical authorities. The objectives were to assess the safety, efficacy, pharmacokinetics, and immunogenicity of IdeS in healthy human subjects following intravenous administration.

A total of 29 healthy subjects were included and divided into four dose groups. The subjects in each dose group were randomized and received either IdeS or placebo. Infusions were given intravenously over 30 minutes for the first two subjects in each group and over 15 minutes for the subsequent subjects. The starting dose was 0.01 mg/kg BW ($N_{IdeS}$: 8 and $N_{Placebo}$: 4) and after evaluation by the Data Monitoring Committee the dose was stepwise increased to 0.04 mg/kg BW ($N_{IdeS}$: 4 and $N_{Placebo}$: 2), 0.12 mg/kg BW ($N_{IdeS}$: 4 and $N_{Placebo}$: 1) and finally 0.24 mg/kg BW ($N_{IdeS}$: 4 and $N_{Placebo}$: 2). The subjects were monitored until day 64 after dosing with more intensive monitoring during the first week. All subjects were male Caucasians with a median age of 23 (range: 20-41) years, weight 76 (range: 59-100) kg with a BMI of 23 (range: 20-30) kg/m$^2$ and there were no statistical significant differences in demographics between the groups.

Assessment of Safety

A total of 77 adverse events (AE) were observed in 24 of the 29 subjects with 39 AEs (in 14 subjects) classified as related (i.e. possible or probable) (Table 1.1). Among these 39 AEs, 35 had a common Toxicity Criteria grade of 1. Four AEs were grade 2 and these were all from one subject (506) who experienced a probable infusion reaction. The symptoms resolved within 15 minutes after treatment with antihistamine (2 mg Tavegyl i.v.) and corticosteroids (8 mg Betapred i.v.) and the IdeS infusion was not interrupted. None of the AEs were reported as serious, met any dose limiting toxicity criteria, or lead to withdrawal of study drug.

Among the 77 AEs the most commonly reported were nasopharyngitis, headache and fatigue. Nasopharyngitis was reported for ten out of twenty subjects on IdeS and for six out of nine subjects on placebo. Seven subjects reported headache at nine occasions (all on IdeS) whereas six subjects (five on IdeS and one on placebo) reported seven incidences of fatigue.

Figure 2A:
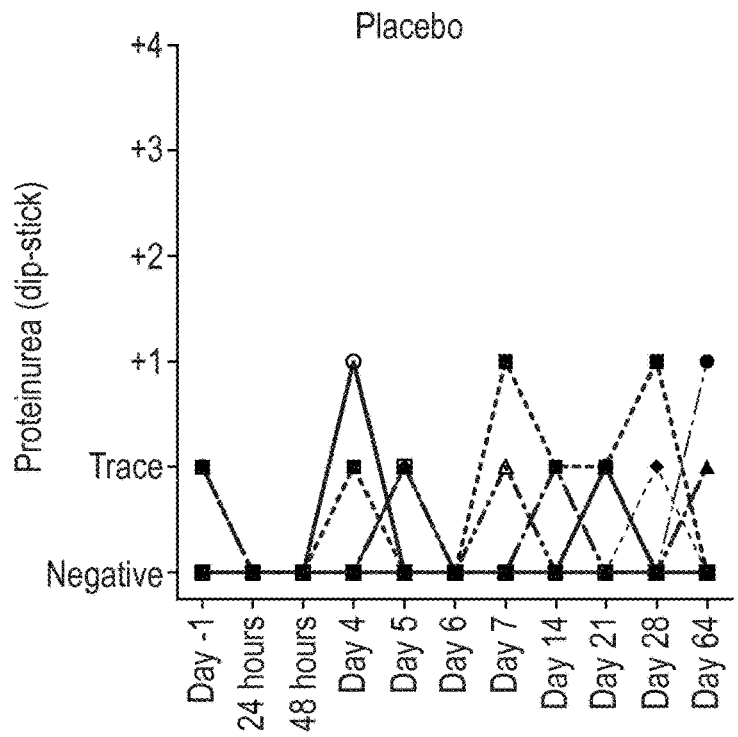
FIGS. 2A and 2B. Proteinuria was monitored as a safety assessment throughout the human study of Example 1. Multistix (Siemens) were routinely used at the hospital and transient proteinuria was detected in several subjects which correlated to IgG cleavage.
Figure 2B:
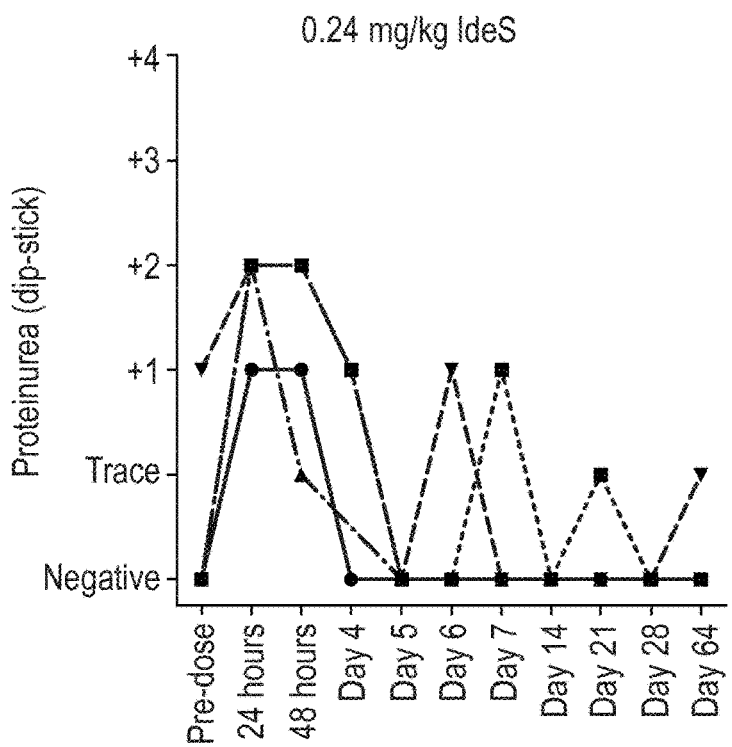

No clinically significant changes in hematology, clinical chemistry or coagulation were identified. However, a transient proteinuria was observed after 24-48 hours in subjects administered an IdeS dose that resulted in significant cleavage of IgG (FIG. 2). This peak probably reflected the clearance of IgG cleavage products from the circulation. Since IdeS degrades IgG antibodies there was an initial concern that study subjects would have an increased risk of infection and the subjects were screened for inherited immunoglobulin disorders, e.g. IgA deficit, before inclusion in the study. Furthermore, concerns were raised that study subjects could be subclinical carriers of bacterial agents (for example pneumococci) with an increased risk of infection due to reduction of plasma IgG. Thus, subjects received antibiotic prophylaxis until serum IgG levels had returned to >4.5 g/L. All study subjects compiled to the antibiotic treatment and there were no signs of an increasing rate of infections.

TABLE 1.1

Summary of adverse events reported for each subject.

| | | Onset of AE | | | 22-64 | | | |
| Dose | Subject | 0-24 hours | 2-7 days | 8-21 days | days | Related | Action | Outcome |
| --- | --- | --- | --- | --- | --- | --- | --- | --- |
| 0.01 | 103 | Nasopharyngitis (1) | | Fatigue (1) Daydreaming (1) Tinnitus (1) | | Possible | None | Resolved |
| | 106 | Nasopharyngitis (1) | Epistaxis (1) Chest discomfort (1) Nightmare (1) | | | Possible | None | Resolved |

TABLE 1.1-continued

Summary of adverse events reported for each subject.

| Dose | Subject | 0-24 hours | Onset of AE 2-7 days | 8-21 days | 22-64 days | Related | Action | Outcome |
|---|---|---|---|---|---|---|---|---|
| | 206 | | | Headache (1) Fatigue (1) Nausea (1) Dizziness (1) | | Possible | None | Resolved |
| 0.04 | 303 | Nausea (1) Flushing (1) | | | | Possible | None | Resolved |
| | 304 | | Oropharyngeal pain (1) Nasopharyngitis (1) | | | Possible | None | Resolved |
| | 305 | | Blister (1) Headache (1) | | | Possible | None | Resolved |
| 0.12 | 404 | | Diarrhoea (1) Abdominal distension (1) | | | Possible | None | Resolved |
| 0.24 | 501 | Headache (1) Abdominal discomfort (1) | Nasopharyngitis (1) | | | Possible | None | Resolved |
| | 504 | | | Asthenia (1) | | Possible | None | Resolved |
| | 506 | Flushing (2) Sinus tachycardia (1) Chest discomfort (2) Pharyngeal oedema (2) Nasal congestion (1) | Throat irritation (1) | Oropharyngeal pain (1) Myalgia (2) | | Probable Possible | Tavegyl Betapred None | Resolved |
| Placebo | 101 | Peripheral coldness (1) Infusion related reaction (1) | Fatigue (1) | | | Possible | None | Resolved |
| | 104 | Dysgeusia (1) | Nasal congestion (1) | | | Possible | None | Resolved |
| | 201 | | Herpes simplex (1) | | | Possible | None | Resolved |
| | 302 | | Chills (1) | | | Possible | None | Resolved |

Pharmacokinetics of IdeS

IdeS concentrations in serum were measured by a LC-MS/MS method based on four peptides derived from IdeS, and serum concentration versus time data were analysed by non-compartmental analysis. The pharmacokinetic parameters were calculated up to 24 hours post dosing, as the remaining concentrations were around or below the estimated quantitative range of the method.

Figure 3A:
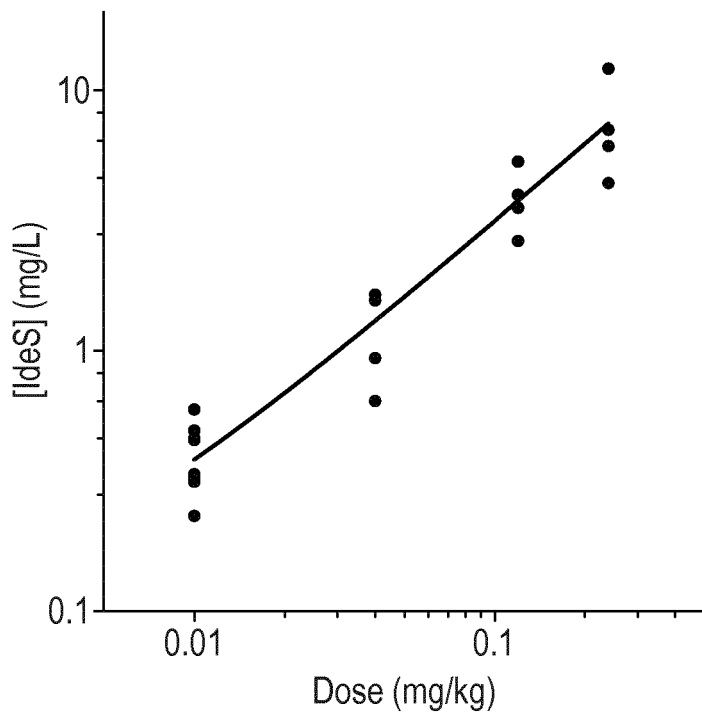
FIGS. 3A and 3B. Pharmacokinetics of IdeS in serum. IdeS concentrations in serum were detected by a LC-MS/MS method based on four peptides derived from IdeS.

Out of 29 subjects, nine received placebo and 20 received IdeS in the dose groups 0.01, 0.04, 0.12 and 0.24 mg/kg BW. None of the analyzed peptides could be detected in the pre-dose samples or in samples from the nine placebo subjects. However, IdeS could be detected in samples from the 20 subjects given IdeS, thereby confirming dosing. The concentration of IdeS increased with dose and the increase in the serum concentration one minute before end of infusion, was dose proportional (FIG. 3A).

Figure 3B:
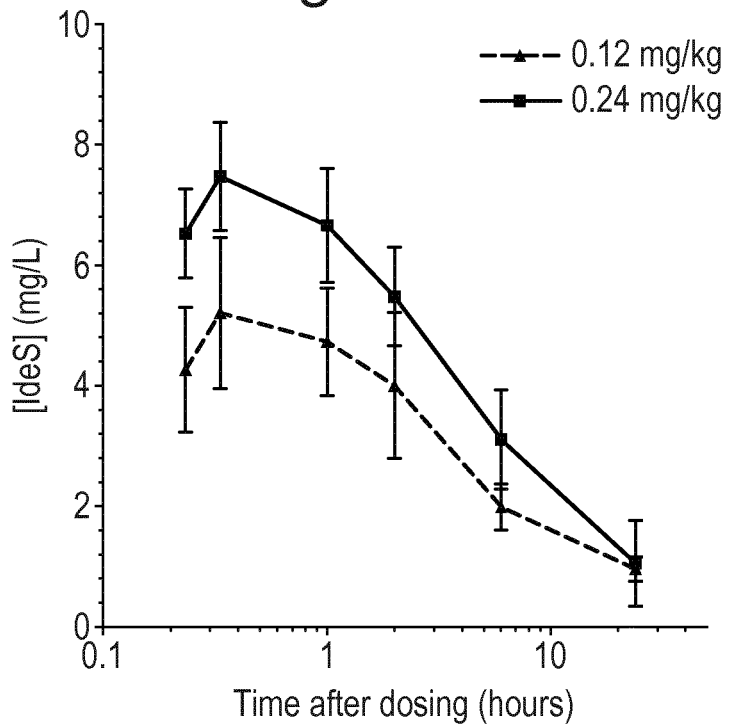

In subjects dosed with 0.12 and 0.24 mg/kg BW, a total of 10 blood samples/subject were collected up to 1 week post dose. The serum concentration of IdeS could be described as a multi-phase elimination curve where the main fraction of the exposure was eliminated during the first 24 hours after dosing. During the first 6 hours after dosing, the mean t½ was 4.1 (±2.6) hours at 0.12 mg/kg BW and 4.9 (±2.8) hours at 0.24 mg/kg BW. The $C_{max}$ was 5.0 (±2.5) mg/L at 0.12 mg/kg BW and 8.3 (±3.7) mg/L at 0.24 mg/kg BW (FIG. 3B).

Efficacy and Pharmacodynamics of IdeS

The efficacy and pharmacodynamics of IgG cleavage by IdeS was evaluated by SDS-PAGE analysis and ELISAs of serum samples from the subjects. IdeS cleaves IgG in two steps (Ryan et al., 2008; Vindebro et al., 2013). The first reaction is a very rapid and efficient cleavage of one of the two heavy chains generating a single cleaved IgG (scIgG), still having one of the two heavy chains intact. The scIgG is a less sensitive but still a functional substrate for IdeS, and this second cleavage generates F(ab')$_2$ and Fc fragments.

Figure 4A:
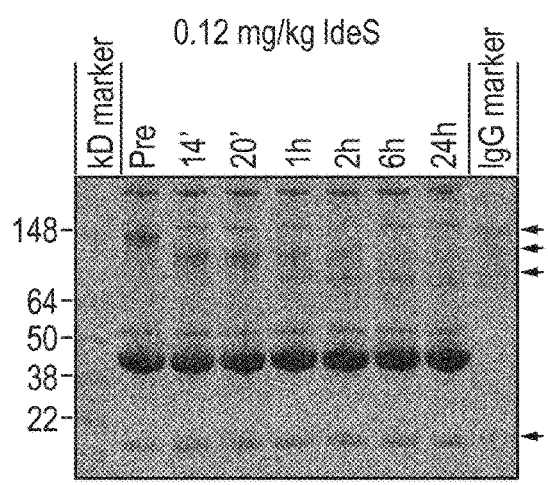
FIGS. 4A-4C. Qualitative pharmacodynamics analysis by SDS-PAGE showed rapid degradation of IgG.
Figure 4B:
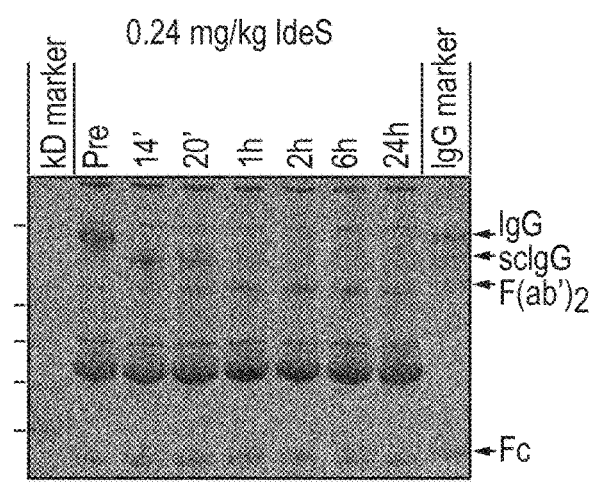
Figure 4C:
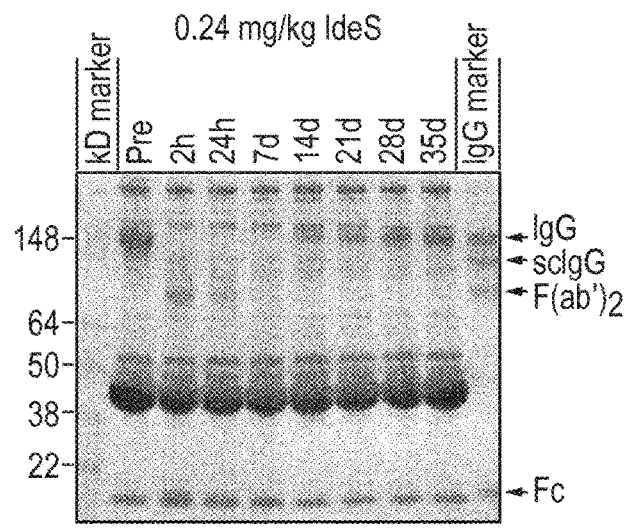

SDS-PAGE analysis revealed that IdeS had full or close to full effect within 6 hours in all 8 subjects dosed with 0.12 or 0.24 mg/kg BW, i.e. the IgG pool was converted into F(ab')$_2$ and Fc fragments (FIGS. 4A and B). The effect was remarkably rapid and the IgG pool was converted into scIgG already during dosing (14 min after starting administration, i.e. 1 min prior to full dose) and maximal effect was accomplished 2-6 hours after dosing in all subjects. Newly synthesized intact IgG was detectable in serum two weeks after dosing and after three weeks the level of intact IgG had further increased and constituted the main IgG fraction in serum. (FIG. 4C).

The dynamics of the Fab- and Fc-containing fragments in serum was analyzed using one Fab- and one Fc-specific ELISA method. The ELISAs did not completely distinguish between the different IgG specimens; i.e. F(ab')$_2$, Fc, scIgG and intact IgG. The Fab-ELISA measured all Fab-containing IgG fragments; i.e. intact IgG, scIgG, and F(ab')$_2$, and the Fc-ELISA measured all Fc containing fragments; i.e. intact IgG, scIgG and free Fc.

Figure 5:
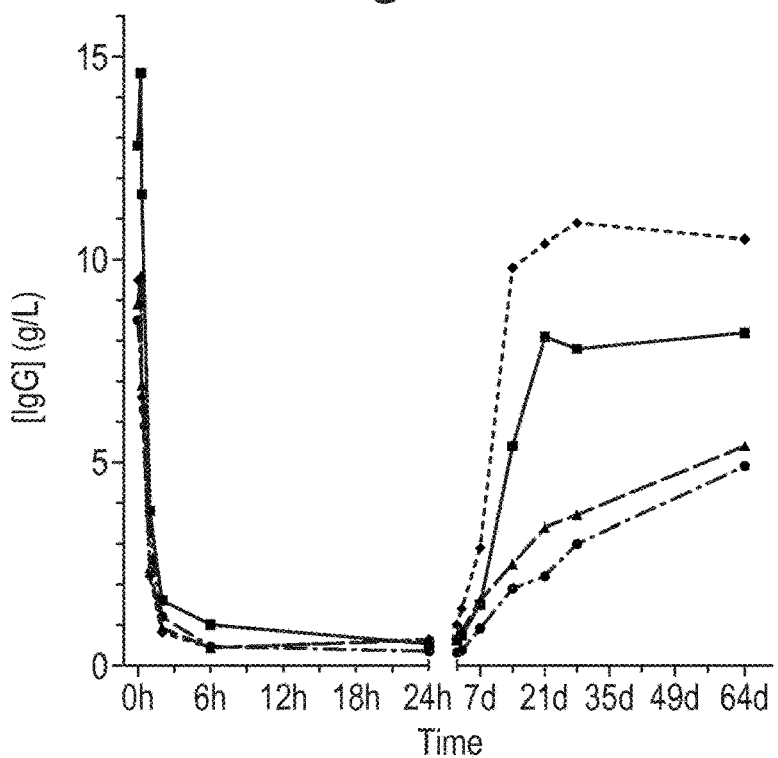
FIG. 5. Quantitative pharmacodynamics analysis by ELISA showed rapid degradation of IgG. Serum IgG levels from individual subjects dosed with 0.24 mg/kg BW IdeS determined using a validated ELISA method (detecting both intact IgG and scIgG). To be able to follow both early, rapid degradation as well as recovery of IgG, the x-axis has been split in two. The first part shows time in hours (0-24 hours) and the second shows time in days (7-64 days).
Figure 6:
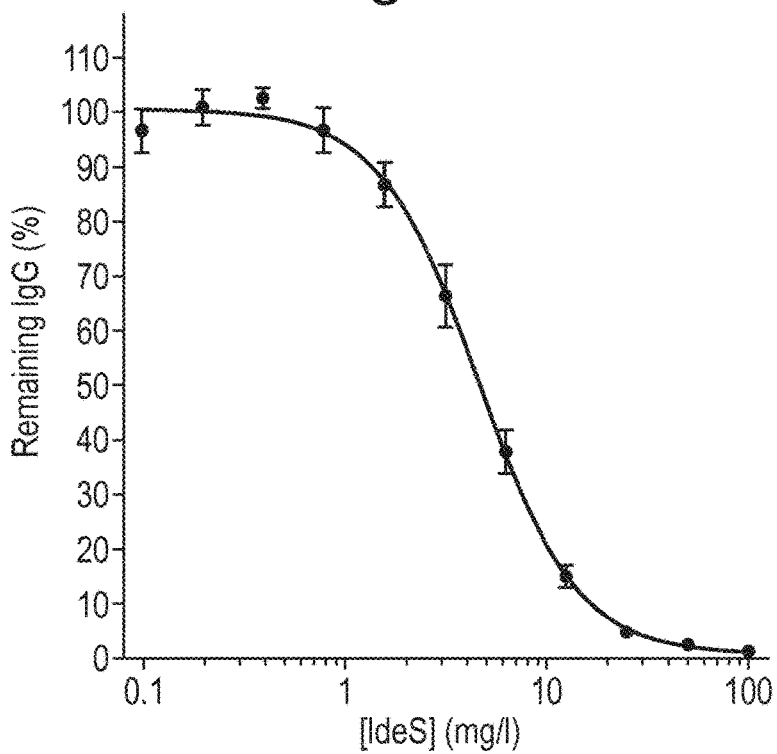
FIG. 6. In vitro titration of IdeS on human serum. Human serum samples from healthy subjects were used as substrates for IdeS and titrated by ELISA (n=20; error bars, mean±SEM). The highest dose group, 0.24 mg/kg BW IdeS, corresponds to approximately 6 mg/L Ides in vitro, 0.12 mg/kg BW to 3 mg/L, 0.04 mg/kg BW to 1 mg/L and 0.01 mg/kg BW to 0.2 mg/L IdeS in vitro. The results are given as percent remaining IgG on the y-axis compared to the start value for each subject. IdeS dose in mg/L is on the x-axis.

The F(ab')$_2$- as well as the Fc-fragments reached bottom levels between one and seven days after dosing after which the levels increased in all subjects due to synthesis of intact IgG (data not shown). The elimination of Fc-fragments was somewhat faster than elimination of F(ab')$_2$-fragments and plateau levels were reached already one day after dosing. The rapid cleavage of human IgG into F(ab')$_2$ and Fc detected by SDS-PAGE analysis was confirmed by ELISA (FIG. 5), showing that 2-6 hours after dosing low plateau levels were reached at less than 5% remaining signal. It was concluded that this signal mainly originated from scIgG. Degradation of IgG in the human subjects correlated well to the previously titrated IdeS concentrations needed to cleave IgG in serum samples from 20 human healthy subjects (FIG. 6).

IdeS and Antigen-Specific IgG Antibodies

Figure 7:
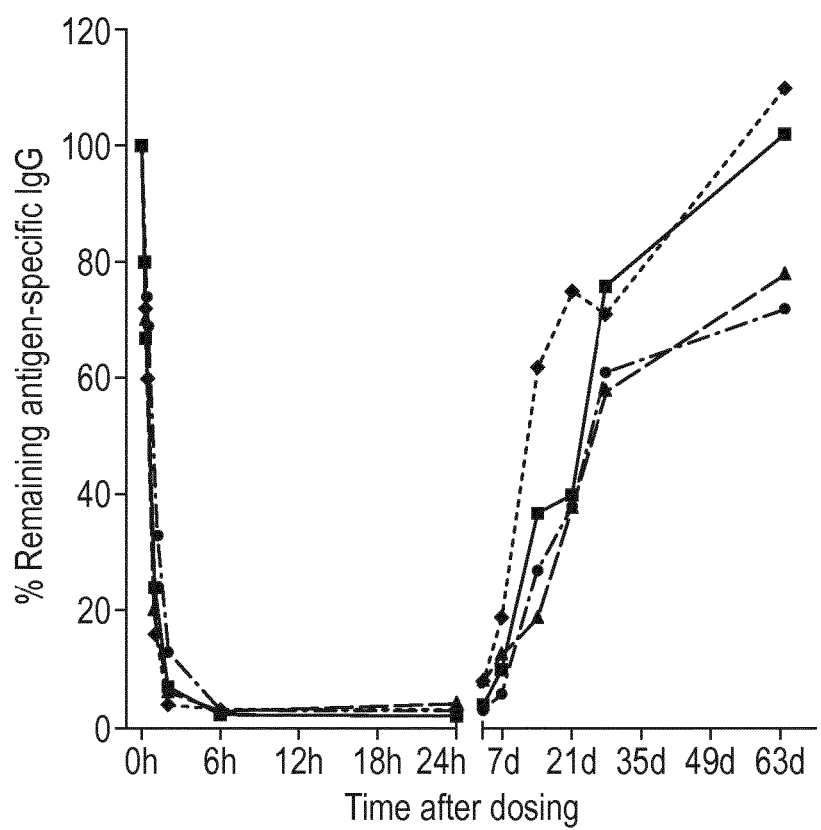
FIG. 7. Antigen-specific pharmacodynamics. Human serum samples from the 0.24 mg/kg BW group (n=4) were addressed for presence of IgG against a mixture of antigens (diphteria, pertussis, tetanus, polio and *Haemophilus influenza* type b). The results are given as percent remaining IgG on the y-axis compared to the start value for each subject. To be able to follow both early, rapid degradation as well as recovery of IgG, the x-axis has been split in two. The first part shows time in hours (0-24 hours) and the second shows time in days (7-64 days).

A majority of the Swedish population has IgG antibodies against the antigen components of the DTaP-IPV//PRP~T (Pentavac®) vaccine (diphtheria, tetanus, pertussis, polio and *Haemophilus* type b). The vaccine is part of the Swedish childhood vaccination schedule and most individuals have received repeated injections of this or of a similar vaccine. This was utilized in an exploratory study where pre-existing IgG against these antigens were measured. The results showed that the effect of IdeS on antigen-specific IgG showed the same pattern as on the total IgG in each individual. In addition, the reappearance of these antigen-specific IgG antibodies was similar to that of total IgG (FIG. 7).

IdeS Treatment and Phagocytic Activity

Figure 8A:
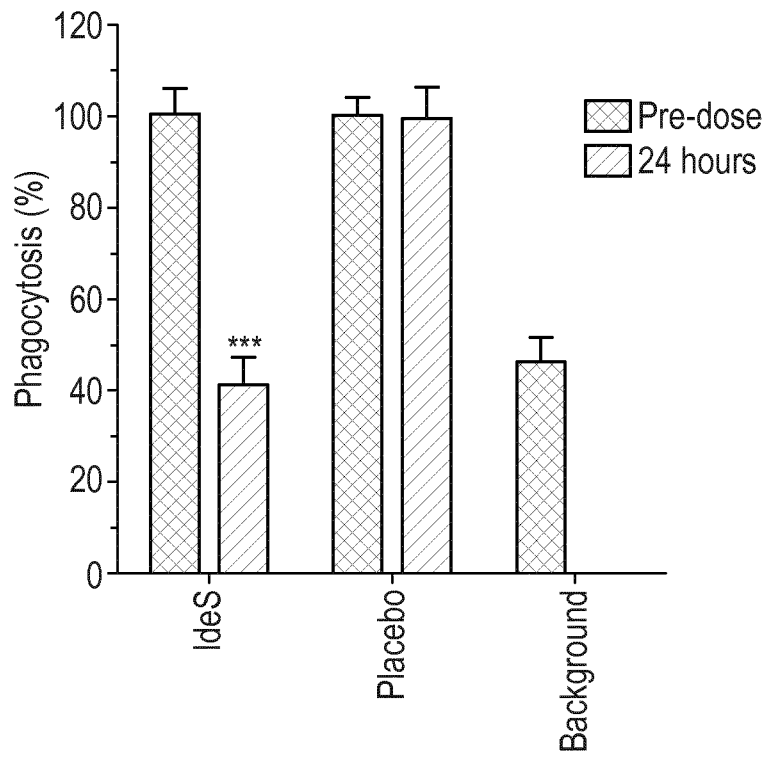
FIGS. 8A and 8B. Serum from subjects dosed with IdeS showed impaired phagocytosis capacity. The opsonizing capacity of IgG in human serum was measured as percent of effector cells with at least one engulfed fluorescent bead.
Figure 8B:
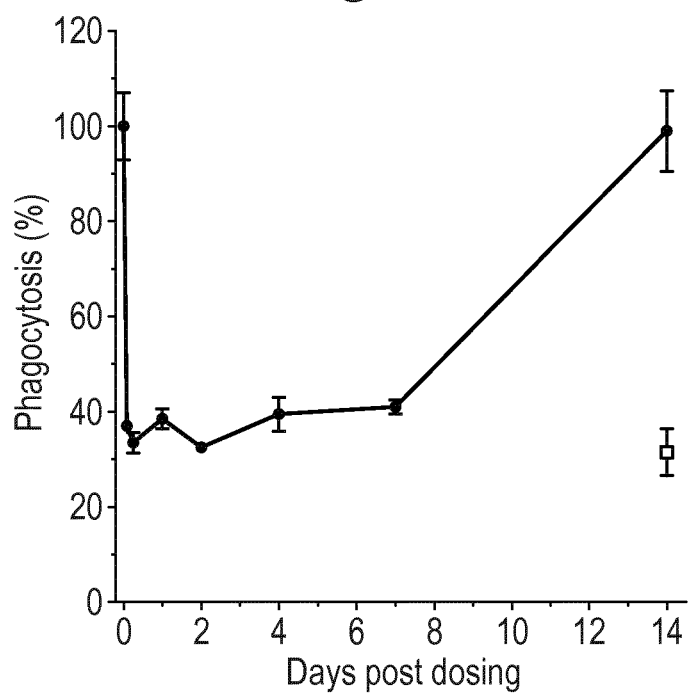

To evaluate the functional activity of the remaining IgG after dosing with IdeS, serum from the subjects were tested in a phagocytosis assay. IgG from serum samples collected pre-dose and at different time-points after IdeS dosing were captured on fluorescent beads, washed and mixed with effector cells and phagocytosis was measured as percent of the effector cells with at least one phagocytized bead. As background in the assay, beads without serum were used to monitor the spontaneous uptake of empty beads by effector cells. The phagocytosis assay showed that all subjects dosed with 0.24 mg/kg BW IdeS reached background phagocytic levels 24 hours after dosing (FIG. 8A). It further showed that remaining IgG or IgG-fragments in serum from subjects treated with 0.24 mg/kg BW IdeS had a significantly decreased phagocytic capacity already at the two hour sampling point and that the phagocytic capacity remained reduced for seven days (FIG. 8B).

IdeS and Immunogenicity

Previous work has shown that a significant proportion of the population has pre-formed IgG antibodies against IdeS (Åkesson et al., 2004). It could be presumed that individuals with preformed IdeS antibodies have an increased risk of hypersensitivity/infusion-like reactions against IdeS. Therefore, a specific in vitro test for the quantitative measurement of IdeS-specific antibodies was developed. The test is a CAP Fluoro enzyme immunoassay (CAP-FEIA/ImmunoCap) assay and it was used to screen study subjects before inclusion. Subjects with elevated IgG antibody titers (>15 mg/L) were excluded from this study. A reference group of 130 human subjects were screened with the test prior to study start. Results shown in FIG. 9A (first column). Ten out of 130 had IdeS specific IgG below the cut-off (<2 mg/L). The median level of anti-IdeS IgG was 6.1 mg/L (range <2-78 mg/L; n=130) with the 80% percentile at 15 mg/L. The 78 healthy human male subjects screened in this study all had detectable IgG against IdeS before treatment. Results shown in FIG. 9A second column. Median level of anti-IdeS IgG was 10.6 mg/L (range 2.1-90.8 mg/L). 28% of the tested individuals had anti-IdeS IgG titers over 15 mg/L and were excluded from the study.

The majority of the study subjects responded with an increase of anti-IdeS IgG. The response was non-detectable one week after dosing but had reached close to peak levels two weeks after dosing and then slowly decreased (FIG. 9B). The median pre-dose level (all subjects) of anti-IdeS IgG was 5.3 mg/L (range: 2.0-10.6 mg/L), and on day 14 the median level of all subjects dosed with IdeS was 104 mg/L (range: 3.1-1744 mg/L). Two months after dosing the levels of anti-IdeS IgG had started to decrease in the majority of individuals and the median anti-IdeS IgG level of all subjects dosed with IdeS was 87.8 mg/L (range: 10.5-764 mg/L). Although the individual variation in the magnitude of the anti-IdeS IgG response was large, there was clearly a stronger response among the subjects receiving 0.12 or 0.24 mg/kg BW IdeS compared to subjects receiving 0.01 or 0.04 mg/kg (FIG. 9C). At day 182, the anti-IdeS IgG levels for 19 out of 20 individuals dosed with IdeS were within the normal range of the previously analysed subjects (range <2-90.8 mg/L; N=208) (FIG. 9D). Only one subject still had anti-IdeS IgG levels slightly above the normal range on day 182 (101 mg/L). This subject was in the 0.01 mg/kg dose group and at day 365, the anti-IdeS IgG levels were within the normal range for this subject (40.5 mg/L). It can be concluded that the anti-IdeS IgG response is very similar in kinetics and magnitude to the response reported for other protein drugs of bacterial origin, such as streptokinase and staphylokinase.

DISCUSSION

This first in class clinical study shows that IdeS converts plasma IgG into single cleaved IgG (scIgG) only minutes after administration. ScIgG has been demonstrated to have compromised effector functions with reduced binding to Fcγ-receptors and reduced Fc-mediated cytotoxicity (Brezski et al., 2009). Despite the lack of pathogenic autoantibodies in the healthy subjects included in the study, normal IgG could be monitored as a biomarker and IdeS showed impressive efficacy in IgG cleaving within the tested dose-range. Full or close to full effect on total IgG, i.e. conversion into $F(ab')_2$ and Fc fragments, was seen in all subjects dosed with 0.12 and 0.24 mg/kg BW IdeS and the study drug showed a favorable safety profile. Only six hours after administration only low concentrations of IgG (<5%) could be detected in blood and the IgG persistently remained low for more than a week until newly synthesized IgG had repopulated the plasma. These results could be compared to the results generally obtained using e.g. plasma exchange where a single plasma volume exchange results in a reduction in IgG to approximately 35% of the original level and 24 h after the plasma exchange the IgG levels have raised to 60% mainly due to lymphatic drainage into the vascular space (Ismail et al., 2001).

As a consequence of IdeS being a bacterial protein and most humans have had previous contact with *S. pyogenes*, all subjects had pre-formed anti-IdeS IgG antibodies and reacted as expected with an IgG response which peaked 2-3 weeks after the IdeS infusion. The amplitude of the anti-drug response varied substantially between individuals, although a dose-response pattern was noted. Six-twelve months after dosing all subjects were back to anti-IdeS antibody levels within the normal range (i.e. <2-91 mg/L) and considering potentially neutralizing antibodies and the safety aspect it is anticipated that IdeS treatment could be repeated after 6-12 months. The IdeS specific CAP FEIA test developed in parallel with this clinical trial could be a valuable tool to guide clinicians when considering repeated dosing.

In addition to total plasma IgG the study investigated IdeS effect on a specific biomarker utilized as a vaccine against diphtheria, tetanus, pertussis, polio and *haemophilus* type b within the Swedish childhood vaccination schedule. The results showed that there was no major difference in antigen-specificity with regard to the IdeS efficacy on total IgG, and all subjects had fully recovered their antigen-specific IgG at the time when the entire IgG pool was back.

The study also evaluated functional relevance of cleaving IgG with IdeS in a phagocytosis assay, where interaction with the Fcγ-receptor is expected to play a major role. This assay showed that already a few hours post administration of IdeS, the phagocytic effect of remaining IgG/IgG-fragments was significantly reduced in all tested subjects, an effect that remained seven days later. The results show that IdeS has the capacity to inactivate Fc-mediated effector function in vivo in humans.

Taken together the data presented here demonstrate that a single dose of IdeS safely, rapidly and efficiently inactivates IgG in humans and that the effect remains for several weeks. IdeS alone and/or in combination with other B-cell attenuating drugs (e.g. Rituximab or Bortezumib) is a very attractive therapeutic approach for many conditions where IgG autoantibodies contribute to the pathology. The immunogenic nature of IdeS most likely prevents chronic treatment although repeated treatment once or twice per year most likely will be possible. However, by applying a judicious therapeutic approach utilizing the high efficacy of IdeS in combination with other drugs or technologies such as immune adsorption or plasma exchange, it should be possible to maintain low plasma levels of pathogenic antibodies for an extended timeframe.

The removal of IgG by IdeS was temporary, suggesting that its best use may be for conditions with a monophasic course, such as antibody mediated graft rejection. This is currently being investigated in a phase II study with IdeS.

REFERENCES

Ackerman, M. E., B. Moldt, R. T. Wyatt, A. S. Dugast, E. McAndrew, S. Tsoukas, S. Jost, C. T. Berger, G. Sciaranghella, Q. Liu, D. J. Irvine, D. R. Burton, and G. Alter. 2011. A robust, high-throughput assay to determine the phagocytic activity of clinical antibody samples. *J Immunol Methods* 366:8-19.

Agniswamy, J., B. Lei, J. M. Musser, and P. D. Sun. 2004. Insight of host immune evasion mediated by two variants of group a *Streptococcus* Mac protein. *J Biol Chem* 279:52789-52796.

Brezski, R. J., O. Vafa, D. Petrone, S. H. Tam, G. Powers, M. H. Ryan, J. L. Luongo, A. Oberholtzer, D. M. Knight, and R. E. Jordan. 2009. Tumor-associated and microbial proteases compromise host IgG effector functions by a single cleavage proximal to the hinge. *Proc Natl Acad Sci USA* 106: 17864-17869.

Carapetis, J. R., A. C. Steer, E. K. Mulholland, and M. Weber. 2005. The global burden of group A streptococcal diseases. *Lancet Infect Dis* 5:685-694.

Collen, D., F. De Cock, E. Demarsin, S. Jenne, I. Lasters, Y. Laroche, P. Warmerdam, and L. Jespers. 1997. Recombinant staphylokinase variants with altered immunoreactivity. III: Species variability of antibody binding patterns. *Circulation* 95:455-462.

Declerck, P. J., S. Vanderschueren, J. Billiet, H. Moreau, and D. Collen. 1994. Prevalence and induction of circulating antibodies against recombinant staphylokinase. *Thromb Haemost* 71:129-133.

Ismail, N., R. Neyra, and R. Hakim. 2001. Plasmapheresis. In Handbook of dialysis, 3rd edn. J. T. Daugirdas, P. G. Blake, and T. S. Ing, editors. Lippincott Williams Wilkins, Philadelphia. 231-262.

Iyer, S. P., L. E. Nikkel, K. K. Nishiyama, E. Dworakowski, S. Cremers, C. Zhang, D. J. McMahon, S. Boutroy, X. S. Liu, L. E. Ratner, D. J. Cohen, X. E. Guo, E. Shane, and T. L. Nickolas. 2014. Kidney Transplantation with Early Corticosteroid Withdrawal: Paradoxical Effects at the Central and Peripheral Skeleton. *J Am Soc Nephrol*

Johansson, B. P., O. Shannon, and L. Björck. 2008. IdeS: a bacterial proteolytic enzyme with therapeutic potential. *PLOS One* 3: e1692.

Jordan, S. C., D. Tyan, D. Stablein, M. McIntosh, S. Rose, A. Vo, M. Toyoda, C. Davis, R. Shapiro, D. Adey, D. Milliner, R. Graff, R. Steiner, G. Ciancio, S. Sahney, and J. Light. 2004. Evaluation of intravenous immunoglobulin as an agent to lower allosensitization and improve transplantation in highly sensitized adult patients with end-stage renal disease: report of the NIH IG02 trial. *J Am Soc Nephrol* 15:3256-3262.

Karlsson, C., L. Malmstrom, R. Aebersold, and J. Malmstrom. 2012. Proteome-wide selected reaction monitoring assays for the human pathogen *Streptococcus pyogenes*. *Nat Commun* 3:1301.

MacLean, B., D. M. Tomazela, N. Shulman, M. Chambers, G. L. Finney, B. Frewen, R. Kern, D. L. Tabb, D. C. Liebler, and M. J. MacCoss. 2010. Skyline: an open source document editor for creating and analyzing targeted proteomics experiments. *Bioinformatics* 26:966-968.

Mainet, D., M. del Rosario, A. Toruncha, P. Prats, C. Valenzuela, and P. Lopez Saura. 1998. Similar, more than 6-months persisted, antibody and neutralizing activity responses in patients with acute myocardial infarction treated with recombinant or natural streptokinase. *Fibrinolysis Proteol* 12:301-309.

Montgomery, R. A., A. A. Zachary, L. C. Racusen, M. S. Leffell, K. E. King, J. Burdick, W. R. Maley, and L. E. Ratner. 2000. Plasmapheresis and intravenous immune globulin provides effective rescue therapy for refractory humoral rejection and allows kidneys to be successfully transplanted into cross-match-positive recipients. *Transplantation* 70:887-895.

Nandakumar, K. S., B. P. Johansson, L. Björck, and R. Holmdahl. 2007. Blocking of experimental arthritis by cleavage of IgG antibodies in vivo. *Arthritis Rheum* 56:3253-3260.

Ojo, A. O., R. A. Wolfe, P. J. Held, F. K. Port, and R. L. Schmouder. 1997. Delayed graft function: risk factors and implications for renal allograft survival. *Transplantation* 63:968-974.

Ryan, M. H., D. Petrone, J. F. Nemeth, E. Barnathan, L. Björck, and R. E. Jordan. 2008. Proteolysis of purified IgGs by human and bacterial enzymes in vitro and the detection of specific proteolytic fragments of endogenous IgG in rheumatoid synovial fluid. *Mol Immunol* 45:1837-1846.

Teleman, J., S. Waldemarson, J. Malmstrom, and F. Levander. 2013. Automated quality control system for LC-SRM setups. *J Proteomics* 95:77-83.

Tradtrantip, L., N. Asavapanumas, and A. S. Verkman. 2013. Therapeutic cleavage of anti-aquaporin-4 autoantibody in neuromyelitis optica by an IgG-selective proteinase. *Mol Pharmacol* 83:1268-1275.

Wenig, K., L. Chatwell, U. von Pawel-Rammingen, L. Björck, R. Huber, and P. Sondermann. 2004. Structure of the streptococcal endopeptidase IdeS, a cysteine proteinase with strict specificity for IgG. *Proc Natl Acad Sci USA* 101: 17371-17376.

Vincents, B., U. von Pawel-Rammingen, L. Björck, and M. Abrahamson. 2004. Enzymatic characterization of the streptococcal endopeptidase, IdeS, reveals that it is a cysteine protease with strict specificity for IgG cleavage due to exosite binding. *Biochemistry* 43:15540-15549.

Vindebro, R., C. Spoerry, and U. von Pawel-Rammingen. 2013. Rapid IgG heavy chain cleavage by the streptococcal IgG endopeptidase IdeS is mediated by IdeS monomers and is not due to enzyme dimerization. *FEBS Lett* 587:1818-1822.

Vo, A. A., M. Lukovsky, M. Toyoda, J. Wang, N. L. Reinsmoen, C. H. Lai, A. Peng, R. Villicana, and S. C. Jordan. 2008a. Rituximab and intravenous immune globulin for desensitization during renal transplantation. *N Engl J Med* 359:242-251.

Vo, A. A., E. A. Wechsler, J. Wang, A. Peng, M. Toyoda, M. Lukovsky, N. Reinsmoen, and S. C. Jordan. 2008b. Analysis of subcutaneous (SQ) alemtuzumab induction therapy in highly sensitized patients desensitized with IVIG and rituximab. *Am J Transplant* 8:144-149.

von Pawel-Rammingen, U., B. P. Johansson, and L. Björck. 2002a. IdeS, a novel streptococcal cysteine proteinase with unique specificity for immunoglobulin G. *EMBO J* 21:1607-1615.

von Pawel-Rammingen, U., B. P. Johansson, H. Tapper, and L. Björck. 2002b. *Streptococcus pyogenes* and phagocytic killing. *Nat Med* 8:1044-1045; author reply 1045-1046.

Yang, R., M. A. Otten, T. Hellmark, M. Collin, L. Björck, M. H. Zhao, M. R. Daha, and M. Segelmark. 2010. Successful treatment of experimental glomerulonephritis with IdeS and EndoS, IgG-degrading streptococcal enzymes. *Nephrol Dial Transplant* 25:2479-2486.

Åkesson, P., M. Rasmussen, E. Mascini, U. von Pawel-Rammingen, R. Janulczyk, M. Collin, A. Olsen, E. Mattsson, M. L. Olsson, L. Björck, and B. Christensson. 2004. Low antibody levels against cell wall-attached proteins of *Streptococcus pyogenes* predispose for severe invasive disease. *J Infect Dis* 189:797-804.

EXAMPLE 2

Introduction

Transplantation in the presence of donor specific antibodies (DSA) risks resulting in a hyper-acute antibody-mediated rejection with acute allograft loss. The study in Example 1 demonstrates that IdeS is safe and well tolerated up to 0.24 mg/kg BW. At this dose IdeS completely cleaved the pool of plasma-IgG within 14 minutes after initiation of infusion. The level of intact IgG was reduced to less than 5% of its original level. The data clearly indicated that a single dose of IdeS is superior to both plasmapheresis and immunoadsorption with respect to efficiency and rate of plasma IgG reduction.

Therefore IdeS treatment of sensitized kidney patients just prior to transplantation should rapidly and efficiently cleave IgG into F(ab')$_2$- and Fc-fragments thereby reducing the serum levels of cytotoxic DSA to a level where living and deceased donor (LD and DD) transplantation is possible. The donor specific F(ab')$_2$-fragments still in circulation at the time-point of transplantation may also prevent binding of e.g. low affinity IgM or residual IgG to the transplant thereby further protecting the organ from rejection. The objective of this study was to investigate if treatment with a clinically relevant dose of IdeS can turn a positive cross-match test into a negative using serum from sensitized patients and to investigate the correlation between the reduction in levels of total IgG and IgG specific to HLA class I and II.

Material and Methods

Serum Samples

The investigated patients were diagnosed with stage 5 CKD and were on the waiting list for kidney transplantation. The patients were all sensitized and positive for anti-HLA. The patients were recruited by Prof. H. Ekberg at the Transplant Unit, Dept. of Nephrology and Transplantation, Skåne University Hospital in Malmö, Sweden and Prof. G. Tufveson at the Dept. of Transplant Surgery, Uppsala University Hospital, Uppsala, Sweden. The patients received written patient information and signed the informed consent before any study related procedures were started. Serum was isolated from 10 ml venous blood according to the hospitals procedure. To ensure confidentiality the principal investigator made the identity of the patients unavailable to the investigating scientists by assigning an identification number (PXX) to the serum samples. The samples were sent to the Clinical Immunology Division at the University Hospital in Uppsala for banking and a fraction of each serum was then sent to Hansa Medical AB in Lund for IdeS related analyses.

IdeS Cleavage in Serum from Patients

Sera (100 µl) from five patients (P02, P04, P07, P08 and P09) were treated with IdeS (batch BX1001865; 9.9 g/l). An IdeS stock at 6 g/l was prepared in PBS/0.1% BSA. 100 µL sera were added to 12 µl 0.1 M HCl in order to adjust serum pH to a physiological level (pH 7.4) and then 2.4 µl of the IdeS stock (6 g/l) were added to reach a final concentration of 125 µg/ml IdeS in 115 µl. All preparations were made on ice. Cleavage was performed at 37° C. (Thermomixer; Eppendorf) for 2 hours and stopped by putting the samples in the freezer (−20° C.) until further analyses. Control samples from each patient were identically mock treated with dilution buffer (PBS/0.1% BSA) replacing IdeS.

Quantification of Human IgG

The serum samples were sent to the Dept. of Clinical Chemistry at Skåne University Hospital in Lund, Sweden for determination of total IgG concentrations. Human serum samples treated with IdeS were analyzed for intact IgG using an ELISA assay developed by Hansa Medical AB. MaxiSorp 96-well ELISA plates were coated in carbonate buffer (pH 9.6) o/n at +4-8° C. with 100 ng/well of AffiniPure F(ab')$_2$ fragment goat anti-human, F(ab')$_2$ fragment specific (Jackson #109-006-097). The plates were washed with PBS+Tween20 (0.05%) and blocked with PBS+2% BSA for one hour at RT. Calibrators and samples were diluted in PBS+0.1% BSA (dilution buffer). After washing the diluted calibrators (M−1, serum from healthy volunteer; conc. 11.2 g/l) and serum samples were added on the plate and left to incubate for one hour at RT. Plates were washed again and 50 µl biotin-SP-AffiniPure F(ab')$_2$ fragment goat anti-human IgG, Fcγ fragment specific (Jackson #109-066-098) diluted 1:20 000, in dilution buffer, was added and incubated for 30 minutes. After another washing, 50 µl of SA-HRP (Pierce #21126) diluted 1:40 000 in dilution buffer was added and after 30 minutes incubation the plate was washed and the reaction was developed with TMB (BioFX Laboratories #TMBW-1000-01), stopped with 0.5M H$_2$SO$_4$ and read at λ=450 nm. The calibrators formed a curve with a four parameter logistic fit (y=b+ (a-b)/(1+xc)^d) within the analyzed range and sample dilutions producing OD-values as close as possible to the IC50 value of the standard curve were preferably used for quantifications.

IdeS Efficacy and Immunogenicity Assessment

The ELISA assay for IdeS efficacy was conducted as in in Example 1, as was the CAP FEIA (ImmunoCap) assay for IdeS specific antibody responses. The results were used only for comparative purposes against the results reported in Example 1 and are not shown.

Complement-Dependent Cytotoxicity (CDC) and Single Antigen Bead (SAB) Analyses (Luminex)

The IdeS and placebo treated sera were analysed for anti-HLA IgG antibodies using SAB analyses against a panel of MHC class-I and -II antigens (LABScreen Single Antigen, One Lambda). The sera were also tested and scored for reactivity in a complement-dependent cytotoxicity (CDC) screen test on T and B cells from 23 donors. T-cells and B-cells were enriched using CD8 and MHC class-II magnetic beads (Dynal), respectively. The SAB and CDC analyses were conducted using validated methods in a clinical setting by Dr. Mats Bengtsson at the Clinical Immunology Division, Department of Oncology, Radiology and Clinical Immunology, Rudbeck Laboratory, University Hospital, Uppsala, Sweden. The CDC reactions were scored according to the International Workshop procedure (Fuller et al., 1982).

Complement-Dependent Lymphocytotoxic Crossmatch (CDC-CXM) Tests

Splenocytes were prepared from Balb/c mice by Ficoll separation. Cells were washed in PBS (×2) and re-suspended to $2\times10^6$ cells/ml in DMEM: F12 (Difco) with 0.1% heat inactivated BSA. The serum samples were treated with DTT to inactivate IgM by mixing 45 µl serum with 5 µl 50 mM DTT and incubate for 30-45 minutes at 37° C. The CXM test was performed by adding 1 µl cell suspension (i.e. 2000 cells) and 1 µl of sample (i.e. serum or controls) to a 60-well Terasaki-plate (Nunc). After 30 minutes of incubation at room temperature, Baby Rabbit Complement (5 µl) (Cedarlane) was added and the mix was further incubated for 60 minutes at RT. FluoroQuench AO/EB Stain Quench (5 µl) (One Lambda inc.) was added to each well and the mix was incubated for 15 minutes at RT. The cytotoxicity was scored (score 1-8) and documented with fluorescence microscopy.

Data Processing

The graphs were constructed using GraphPad Prism version 5.0d for Mac OS X, GraphPad Software, San Diego California USA, www.graphpad.com.

Results and Discussion

IdeS-Treatment of Patient Sera

Figure 10:
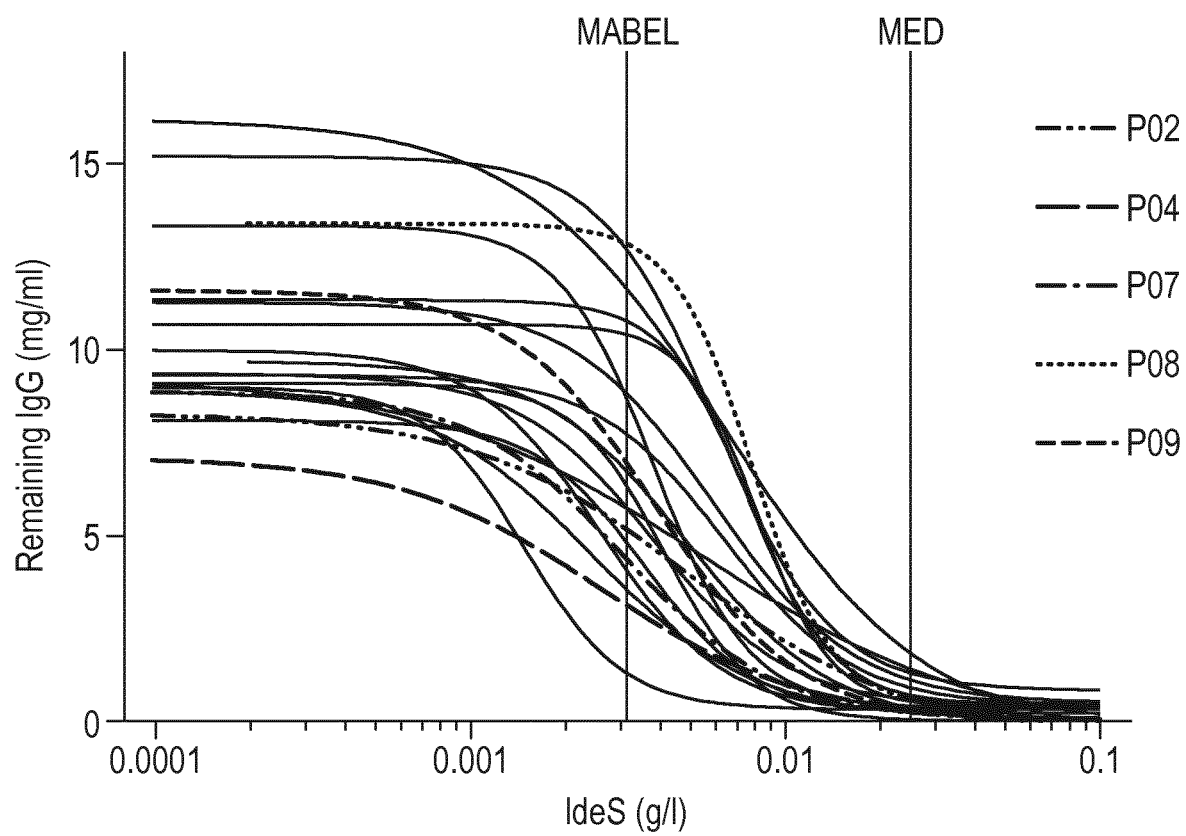
FIG. 10. Efficacy of IdeS in serum from twenty tested donors (healthy volunteers and stage 5 CKD patients). Remaining IgG after treatment of human sera with different concentrations of IdeS was determined using ELISA. Figure shows the sigmoid dose-response curves of the individual human sera where remaining IgG in mg/ml is plotted against IdeS dose (g/L). Calculated MABEL (0.0031 g/L) and MED (0.025 g/L) are indicated in the graphs (dark blue line). The selected patient sera P02, P04, P07, P08 and P09 are highlighted in different colours.

Serum was collected from twelve sensitized patents with stage 5 CKD awaiting kidney transplantation. IdeS was dose titrated in each serum to determine the efficacy of IdeS treatment and it could be concluded that IdeS effectively cleaved IgG in all patient sera within the tested concentration-range although there were individual differences in the minimal concentration of IdeS required to reach maximum effect (FIG. 10). Total IgG levels in the patient sera were analyzed and found to be within the normal range (median: 9.3 g/L; range 6.5-16.2 g/L). Furthermore, the anti-IdeS levels were determined using IdeS-ImmunoCAP analysis and all 12 serum contained low levels (median: 4.5 mg/L; range <2-14.8 mg/L) of anti-IdeS IgG (HMed Doc. No: 2012-041). There was no clear correlation between individual anti-IdeS levels or the levels of total IgG and IdeS efficacy. Five representative sera; i.e. P02, P04, P07, P08 and P09, were selected for further analyses of anti-HLA antibodies.

The sera were treated with IdeS or placebo (PBS) for two hours at 37° C. and analyzed for remaining IgG using the described ELISA. As a comparison we performed exhaustive immune-adsorption with Protein-A sepharose and analyzed remaining IgG in parallel to the IdeS treated samples. The results demonstrated that IdeS treatment reduced the level of IgG from 7.5-15.9 g/L to 0.17-0.4 g/L (table 2.1). The immunoadsorption was generally less effective with 0.18-1.5 g/L remaining IgG.

TABLE 2.1

Sera from five patients (P02, P04, P07, P08 and P09) treated with IdeS, PBS or subjected to immunoadsorption (IA). IgG in g/L.

|  | P02 | P04 | P07 | P08 | P09 |
| --- | --- | --- | --- | --- | --- |
| PBS | 11.0 | 7.5 | 11.6 | 15.9 | 12.0 |
| IdeS | 0.22 | 0.21 | 0.17 | 0.40 | 0.34 |
| IA | 0.50 | 0.31 | 0.18 | 1.5 | 0.80 |

These results should be compared to the results generally obtained using e.g. plasmapheresis where a single plasma volume exchange results in a reduction in IgG to approximately 35% of the original level and 24 h after the plasma exchange the IgG levels have raised to 60% mainly due to lymphatic drainage into the vascular space (Ismail et al., 2001). Even repeated, up to five, cycles of plasmapheresis results in oscillating IgG levels between 10% at the end of the procedure to 20-25% before the next procedure. The pre-clinical studies described in Example 1 demonstrated that a single intravenous injection of IdeS in rabbits results in a rapid (within 1 h) reduction of intact IgG down to 2-3% of the original level and that the IgG level remains low for several days after treatment. Similar results were obtained in the clinical phase I trial described in Example 1 after administering IdeS to healthy human subjects. The pool of plasma IgG was completely converted to scIgG already during administration of 0.24 mg/kg BW of IdeS (14 minutes after initiation of infusion) and two hours after dosing to pool IgG had been further converted to F(ab')$_2$ and Fc. The data showed that levels corresponding to <5% of the original levels, most of which consisted of scIgG, could be reached already between 2-6 hours after dosing and that it took several days before the level started to gradually increase.

CDC-Analyses

IdeS and placebo treated serum from patients P02, P04, P07, P08 and P09 were subjected to a sera-sceen CDC test against a panel of T-cells (i.e. cells enriched for CD8+) and B cells (i.e. cells enriched for MHC class-II+) from selected and well-characterized donors. The results, presented in table 2.2 and 2.3 (also see Summary of individual patient results, below), clearly demonstrated that IdeS treatment had the capacity to completely abrogate complement-dependent cytotoxicity mediated by serum containing donor-specific IgG. In the T-cell test, that mainly addressed anti-MHC class I antibodies, IdeS treatment could completely desensitize patients P02, P04, P07 and P09 and significantly improve the grade of sensitization for patient P08 (table 2.2). In the B cell test, that addressed anti-MHC class I and class II antibodies, IdeS 20) treatment improved the grade of sensitization for all patients (table 2.3). It could be concluded that IdeS-treatment clearly reduced the CDC reactivity against potential donors thereby increasing the chance of finding a suitable donor for all tested patients. It was also clear from the data presented here that IdeS-treatment had the capacity to turn a positive pre-transplantation crossmatch into a negative thereby making a sensitized patient transplantable.

Anti-HLA Analyses

To verify that the reduction in total IgG after IdeS treatment was reflected in a reduction in the levels of anti-HLA antibodies in the sera from sensitized patients the samples treated with IdeS or placebo were subjected to SAB analyses. The array included 188 allelic variants of MHC including 97 MHC class I (HLA-A, -B and -C) and 91 MHC class II (HLA-DP, -DQ and -DR) antigens. The results confirmed that IdeS treatment could reduce the levels of anti-HLA IgG in serum from sensitized patients and it could be concluded that the reactivity of serum from all tested patients to individual MHC molecules of class I and class II was significantly reduced after IdeS treatment (FIGS. 11-15 and Appendix I and II). A threshold at an MFI (raw)>1000 (sometimes >2000) is quite often used as a cut-off for a significant reactivity against a specific HLA antigen when considering transplantation of a sensitized patient. IdeS treatment could clearly reduce the number of HLA-antigens above these thresholds in all tested patients both at MHC class I and class II (table 2.4 and 2.5; Appendix I-II).

IdeS Treatment has the Capacity to Turn a Positive CXM Negative

Naturally occurring antibodies against [Gal α-1,3-Gal] structures (anti-Gal antibodies) are the primary effectors of human hyperacute rejection (HAR) of nonhuman tissue. Unlike most mammals, humans lack a functional α-1,3-galactosyltransferase (GalT) gene and produce abundant anti-Gal antibodies, putatively in response to GalT+ enteric bacteria (Ding et al., 2008 and Pierson 2009). The objective was to investigate if the primate v.s. non-primate anti-Gal reactivity can be exploited as a pseudo marker to analyse the effect of IdeS using clinical serum samples from the phase I study of Example 1.

The level of IgG was measured in consecutive serum samples collected before and after dosing of 0.24 mg/kg IdeS to human healthy subjects using a validated PD-ELISA (table 2.6). The data demonstrated that there was approximately a 10-fold decrease in IgG two hours after dosing and a 20-fold decrease 24 hours after dosing of IdeS. The PD-ELISA does not discriminate between intact fully functional IgG and scIgG with an attenuated Fc-effector function. SDS-PAGE analyses indicated that scIgG constituted the dominating fraction of the remaining IgG in these sera suggesting that the level of fully functional IgG is low already minutes after IdeS treatment (see Example 1).

TABLE 2.2

Sera-screen test of sera from sensitized patients (P02, P04, P07, P08 and P09) treated with IdeS or placebo (PBS) against T cells from a panel of donors (N = 23). Reactivity was scored by assigning a number 1-8 where 1 corresponds to 0% cytotoxicity and 8 corresponds to >80% cytotoxicity.

| | P02 | | P04 | | P07 | | P08 | | P09 | |
|---|---|---|---|---|---|---|---|---|---|---|
| | +PBS | +IdeS | +PBS | +IdeS | +PBS | +IdeS | +PBS | +IdeS | +PBS | +IdeS |
| PC:8 | 1 | 1 | 1 | 1 | 8 | 1 | 8 | 1 | 4 | 1 |
| PC:10 | 1 | 1 | 1 | 1 | 8 | 1 | 8 | 1 | 1 | 1 |
| PC:19 | 6 | 1 | 8 | 1 | 1 | 1 | 8 | 8 | 8 | 1 |
| PC:20 | 1 | 1 | 1 | 1 | 8 | 1 | 8 | 1 | 1 | 1 |
| PC:9B | 8 | 1 | 1 | 1 | 8 | 1 | 8 | 8 | 1 | 1 |
| PC:11 | 1 | 1 | 1 | 1 | 8 | 1 | 8 | 8 | 1 | 1 |
| PC:24B | 6 | 1 | 1 | 1 | 8 | 1 | 8 | 1 | 8 | 1 |
| PC:25 | 1 | 1 | 1 | 1 | 4 | 6 | 8 | 1 | 8 | 1 |
| PC:27 | 1 | 1 | 1 | 1 | 1 | 1 | 8 | 8 | 1 | 1 |
| PC:29 | 1 | 1 | 1 | 1 | 1 | 1 | 8 | 2 | 1 | 1 |
| PC:15 | 1 | 1 | 6 | 1 | 8 | 1 | 8 | 1 | 8 | 1 |
| PC:4 | 1 | 1 | 1 | 1 | 8 | 1 | 8 | 1 | 8 | 1 |
| PC:14 | 2 | 1 | 6 | 1 | 8 | 1 | 8 | 1 | 1 | 1 |
| PC:30 | 1 | 1 | 8 | 1 | 8 | 1 | 8 | 6 | 1 | 1 |
| PC:28 | 1 | 1 | 1 | 1 | 1 | 1 | 8 | 1 | 8 | 1 |
| PC:26 | 1 | 1 | 1 | 1 | 8 | 1 | 8 | 8 | 1 | 1 |
| PC:21 | 1 | 1 | 1 | 1 | 8 | 1 | 8 | 1 | 1 | 1 |
| PC:22 | 1 | 1 | 1 | 1 | 8 | 1 | 8 | 1 | 1 | 1 |
| PC:12 | 1 | 1 | 1 | 1 | 1 | 1 | 8 | 1 | 1 | 1 |
| PC:17 | 1 | 1 | 8 | 1 | 8 | 1 | 8 | 8 | 1 | 1 |
| PC:18 | 1 | 1 | 1 | 1 | 8 | 1 | 8 | 6 | 8 | 1 |
| PC:13 | 1 | 1 | 1 | 1 | 1 | 1 | 8 | 1 | 1 | 1 |
| PC:16 | 1 | 1 | 1 | 1 | 1 | 1 | 8 | 1 | 1 | 1 |
| Median | 1 | 1 | 1 | 1 | 8 | 1 | 8 | 1 | 1 | 1 |
| T-PRA (%) | 17 | 0 | 22 | 0 | 70 | 4 | 100 | 39 | 35 | 0 |

TABLE 2.3

Sera-screen test of sera from sensitized patients (P02, P04, P07, P08 and P09) treated with IdeS or placebo (PBS) against B cells from a panel of donors (N = 23). Reactivity was scored by assigning a number 1-8 where 1 corresponds to 0% cytotoxicity and 8 corresponds to >80% cytotoxicity.

| | P02 | | P04 | | P07 | | P08 | | P09 | |
|---|---|---|---|---|---|---|---|---|---|---|
| | +PBS | +IdeS | +PBS | +IdeS | +PBS | +IdeS | +PBS | +IdeS | +PBS | +IdeS |
| PC:8 | 8 | 1 | 1 | 1 | 8 | 1 | 8 | 1 | 8 | 1 |
| PC:10 | 8 | 1 | 1 | 1 | 8 | 1 | 8 | 6 | 8 | 4 |
| PC:19 | 1 | 1 | 8 | 1 | 8 | 1 | 8 | 8 | 8 | 1 |
| PC:20 | 1 | 1 | 1 | 1 | 8 | 8 | 8 | 8 | 8 | 1 |
| PC:9B | 8 | 6 | 2 | 4 | 8 | 6 | 8 | 8 | 8 | 4 |
| PC:11 | 8 | 1 | 8 | 4 | 8 | 6 | 8 | 8 | 8 | 1 |
| PC:24B | 8 | 1 | 1 | 1 | 8 | 1 | 8 | 8 | 8 | 1 |

TABLE 2.3-continued

Sera-screen test of sera from sensitized patients (P02, P04, P07, P08 and P09) treated with IdeS or placebo (PBS) against B cells from a panel of donors (N = 23). Reactivity was scored by assigning a number 1-8 where 1 corresponds to 0% cytotoxicity and 8 corresponds to >80% cytotoxicity.

| | P02 | | P04 | | P07 | | P08 | | P09 | |
| --- | --- | --- | --- | --- | --- | --- | --- | --- | --- | --- |
| | +PBS | +IdeS | +PBS | +IdeS | +PBS | +IdeS | +PBS | +IdeS | +PBS | +IdeS |
| PC:25 | 1 | 1 | 1 | 1 | 6 | 4 | 8 | 1 | 8 | 1 |
| PC:27 | 6 | 1 | 1 | 1 | 1 | 1 | 8 | 8 | 8 | 1 |
| PC:29 | 1 | 1 | 2 | 2 | 1 | 1 | 8 | 6 | 8 | 1 |
| PC:15 | 6 | 1 | 4 | 1 | 8 | 2 | 8 | 6 | 8 | 4 |
| PC:4 | 2 | 1 | 1 | 1 | 8 | 6 | 8 | 6 | 8 | 1 |
| PC:14 | 8 | 1 | 8 | 4 | 8 | 6 | 8 | 8 | 8 | 2 |
| PC:30 | 8 | 1 | 4 | 2 | 8 | 2 | 8 | 8 | 8 | 1 |
| PC:28 | 8 | 1 | 4 | 2 | 4 | 6 | 8 | 1 | 8 | 1 |
| PC:26 | 6 | 4 | 8 | 1 | 8 | 6 | 8 | 8 | 8 | 4 |
| PC:21 | 1 | 1 | 1 | 1 | 8 | 8 | 8 | 4 | 1 | 1 |
| PC:22 | 8 | 1 | 8 | 4 | 8 | 4 | 8 | 4 | 8 | 4 |
| PC:12 | 1 | 2 | 1 | 1 | 4 | 1 | 8 | 1 | 8 | 1 |
| PC:17 | 8 | 1 | 8 | 1 | 8 | 1 | 8 | 8 | 8 | 1 |
| PC:18 | 8 | 1 | 8 | 1 | 8 | 2 | 8 | 8 | 8 | 1 |
| PC:13 | 8 | 1 | 8 | 1 | 1 | 2 | 8 | 1 | 6 | 1 |
| PC:16 | 1 | 1 | 1 | 1 | 1 | 1 | 8 | 8 | 8 | 1 |
| Median | 8 | 1 | 2 | 1 | 8 | 2 | 8 | 8 | 8 | 1 |
| B-PRA (%) | 70 | 13 | 57 | 30 | 83 | 61 | 100 | 78 | 96 | 26 |

TABLE 2.4

SAB analyses against 31 HLA-A, 50 HLA-B and 16 HLA-C antigens. The table gives the number of antigens having an MFI (Raw) above 1000 or above 2000 in each patient before and after IdeS treatment. Patients P02, P04, P07, P08 and P09.

| | | HLA-A | | HLA-B | | HLA-C | |
| --- | --- | --- | --- | --- | --- | --- | --- |
| | | +PBS | +IdeS | +PBS | +IdeS | +PBS | +IdeS |
| P02 | >1000 | 12 | 0 | 38 | 9 | 4 | 0 |
| | >2000 | 12 | 0 | 33 | 0 | 4 | 0 |
| P04 | >1000 | 9 | 0 | 44 | 18 | 12 | 2 |
| | >2000 | 5 | 0 | 42 | 3 | 8 | 0 |
| P07 | >1000 | 0 | 0 | 34 | 0 | 0 | 0 |
| | >2000 | 0 | 0 | 34 | 0 | 0 | 0 |
| P08 | >1000 | 29 | 3 | 48 | 0 | 16 | 4 |
| | >2000 | 24 | 1 | 44 | 0 | 16 | 0 |
| P09 | >1000 | 20 | 0 | 7 | 0 | 1 | 0 |
| | >2000 | 17 | 0 | 0 | 0 | 1 | 0 |

TABLE 2.5

SAB analyses against 26 HLA-DP, 29 HLA-DQ and 36 HLA-DR antigens. The table gives the number of antigens having an MFI (Raw) above 1000 or above 2000 in each patient before and after IdeS treatment. Patients P02, P04, P07, P08 and P09.

| | | HLA-DP | | HLA-DQ | | HLA-DR | |
| --- | --- | --- | --- | --- | --- | --- | --- |
| | | +PBS | +IdeS | +PBS | +IdeS | +PBS | +IdeS |
| P02 | >1000 | 8 | 0 | 19 | 0 | 23 | 2 |
| | >2000 | 7 | 0 | 14 | 0 | 23 | 0 |
| P04 | >1000 | 0 | 0 | 7 | 0 | 16 | 2 |
| | >2000 | 0 | 0 | 7 | 0 | 11 | 0 |
| P07 | >1000 | 0 | 0 | 0 | 0 | 13 | 0 |
| | >2000 | 0 | 0 | 0 | 0 | 12 | 0 |
| P08 | >1000 | 7 | 0 | 27 | 23 | 33 | 23 |
| | >2000 | 1 | 0 | 27 | 16 | 33 | 2 |
| P09 | >1000 | 0 | 0 | 22 | 7 | 23 | 0 |
| | >2000 | 0 | 0 | 16 | 3 | 20 | 0 |

TABLE 2.6

Level of IgG measured in serum samples from healthy subjects dose with placebo (503) or IdeS (504-506) using a validated PD-ELISA that measures intact IgG (plus scIgG).

| | [IgG] (g/l) | | |
| --- | --- | --- | --- |
| | Pre-dose | 2 h | 24 h |
| 503 | 10.6 | 14.1 | 12.6 |
| 504 | 12.8 | 1.6 | 0.53 |
| 505 | 8.9 | 0.91 | 0.62 |
| 506 | 9.5 | 0.81 | 0.65 |

Figure 16:
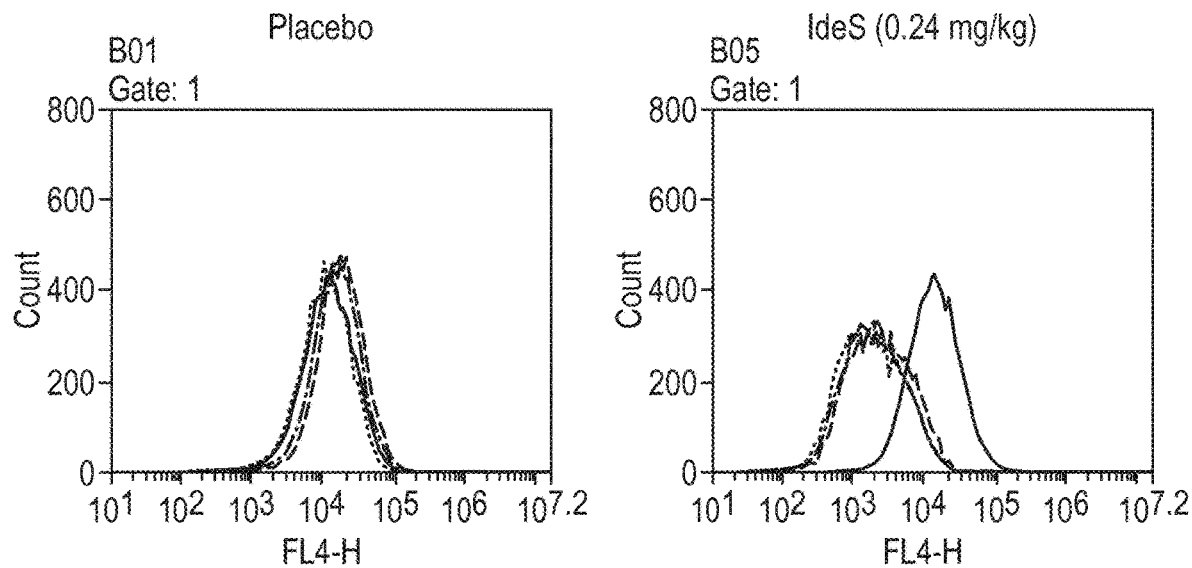
FIG. 16. Balb/c spleenocytes (gate P1) stained with serum (10 µl non-DTT treated) from subjects 503 and 504 collected pre-dosing (black), 24 h after dosing (red), 48 h after dosing (green) and 96 h (blue) after dosing with IdeS or placebo. Binding was detected using a secondary reagent against human Fcγ. For the IdeS graph, the pre-dosing plot is to the right of all three after dosing plots. Thus, there is a reduction in the ability of serum to bind to mouse splenocytes at 24 hrs that is maintained at 96 hrs.

In order to investigate if the human serum samples contained IgG that bind to murine antigens (e.g. anti-gal), mouse spleen cells were stained for FACS analyses with undiluted consecutive serum samples collected before and at different time-point after dosing of 0.24 mg/kg IdeS in human healthy subjects. The binding of IgG to the cells was detected using a hFcγ-specific reagent. The data demonstrated a clear shift 24 hours after IdeS treatment that was sustained up to 96 hours after treatment (representative graph in FIG. 16) consistent with the demonstrated reduction in total IgG. The cleavage products, i.e. F(ab')$_2$- and Fcγ-fragments, have a rapid elimination from circulation and reaches low plateau levels 1-2 days after IdeS treatment (see Example 1). Consequently, competition between potentially remaining intact IgG and F(ab')$_2$-fragments for binding to target antigens was expected to be insignificant in this assay. It was concluded that the pre-dose samples collected in the phase I trial contain IgG that bind mouse cells and that IdeS treatment reduced this reactivity.

Figure 17:
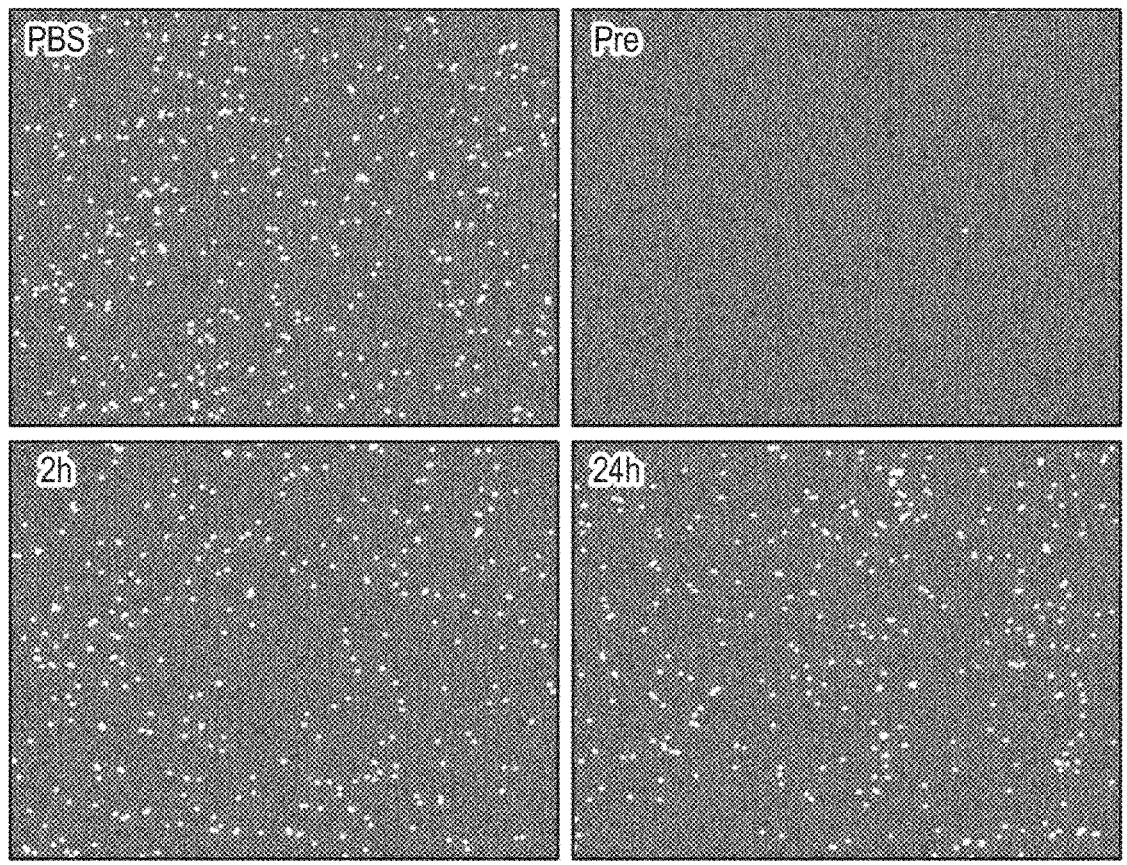
FIG. 17. Xenogenic cross-match between serum from healthy subject (504) dosed with 0.24 mg/kg BW of IdeS and spleen cells from Balb/c mouse. The serum samples were collected pre-dose and at the indicated time-points post-dose. Sera were treated with DTT to inactivate IgM. Overlay photographs of Terasaki-wells showing living cells (green/bright) and dead cells (red/dull). Spleen cells treated with PBS only (no serum) were used as control for spontantaneous cell death.

It has been demonstrated that human serum contains reactivity against Gal-antigens that results from complement fixating IgG and IgM (Pierson, 2009). This was confirmed by demonstrating that human serum reacted strongly in a complement dependent cross-match test (CDC-CXM) (Terasaki test) against spleen cells from mouse (Balb/c) (data not shown). Since IdeS is very specific for IgG all samples were DTT-treated in order to inactivate IgM present in the tested sera. Consecutive serum samples collected before dosing, two hours after dosing and 24 hours after dosing from three healthy subjects (504, 505 and 506) dosed with 0.24 mg/kg BW were tested in a CDC-CXM against spleen cells from Balb/c mouse. All pre-dose samples reacted strongly (score 8) whereas the samples collected at 2 and 24 hours after IdeS treatment were completely negative (score 1) (table 2.7 and FIG. 17).

TABLE 2.7

Xenogenic cross-match test with sera from healthy subjects (504-506) dosed with 0.24 mg/kg IdeS and spleen cells from Balb/c mouse. Reactivity was scored by assigning a number 1-8, where 1 corresponds to no cytotoxicity and 8 corresponds maximum cytotoxicity.

|     | Pre-dose | 2 h | 24 h |
| --- | --- | --- | --- |
| 504 | 8 | 1 | 1 |
| 505 | 8 | 1 | 1 |
| 506 | 8 | 1 | 1 |

Taken together it was concluded that IdeS-treatment can reduce the serum level of specific IgG with the ability to bind murine cell-surface targets and that this effect is sustained for several days after IdeS-treatment. The fact that the IgG did not recover already within the first day(s) following IdeS treatment clearly indicated that IdeS not only cleaved plasma IgG but also IgG located outside the vascular system, i.e. in the interstitial fluid. Furthermore, serum collected two and 24 hours after IdeS-treatment from subjects treated with 0.24 mg/kg IdeS could not mediate complement-dependent cytotoxicity (CDC) against mouse target cells, clearly demonstrating that IdeS can turn a positive CMX result into a negative result.

Summary of Individual Patient Results
Patient P02

Figure 11:
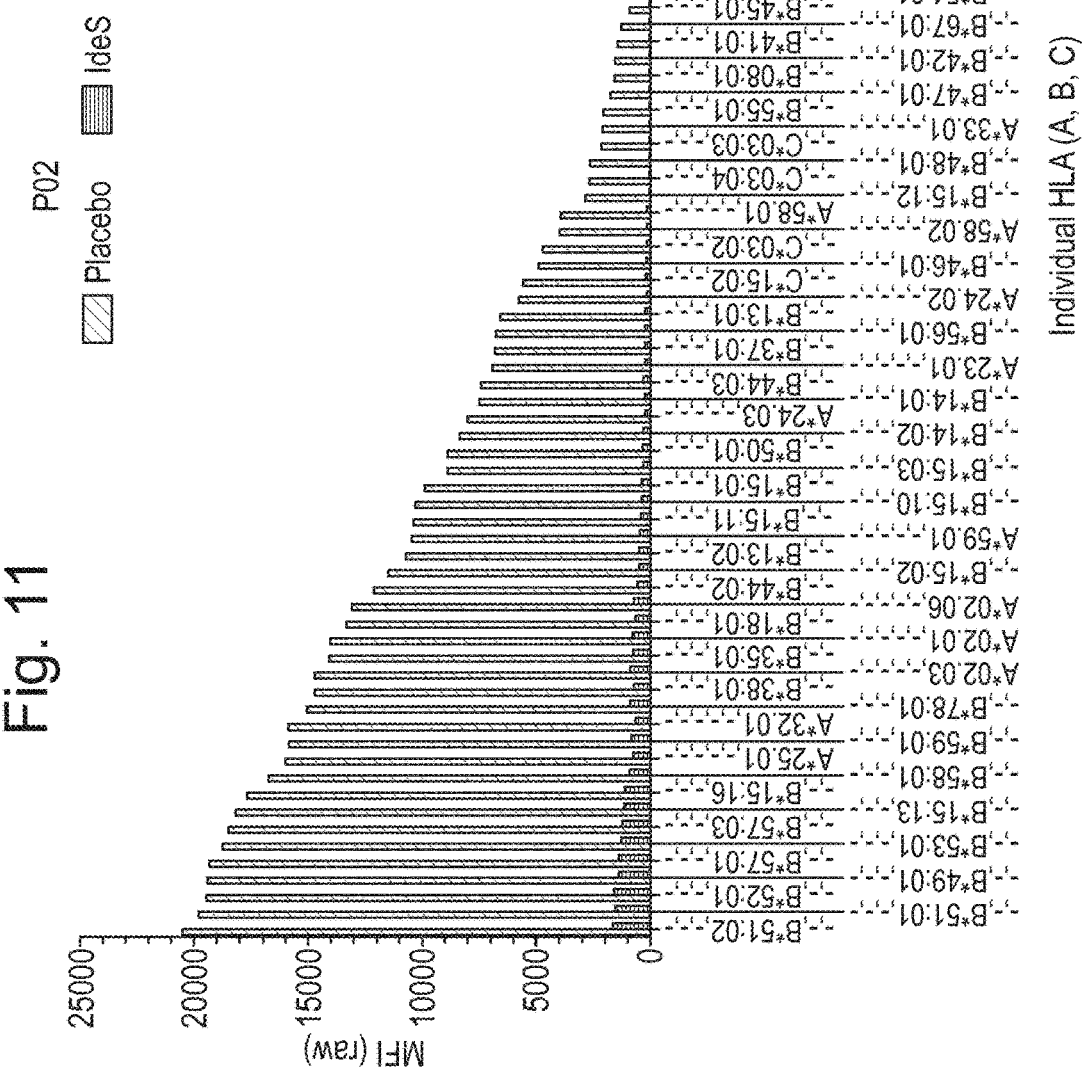
FIG. 11. Efficacy of IdeS on anti-HLA IgG in serum from sensitized patient No. P02. Graph shows the MFI (Raw) against individual antigens for (upper graph) MHC class-I (A, B and C) and (lower graph) MHC class-II (DP, DQ and DR) after mock (blue) and IdeS (red) treatment. MFI: Mean fluorescent intensity.
Figure 11:
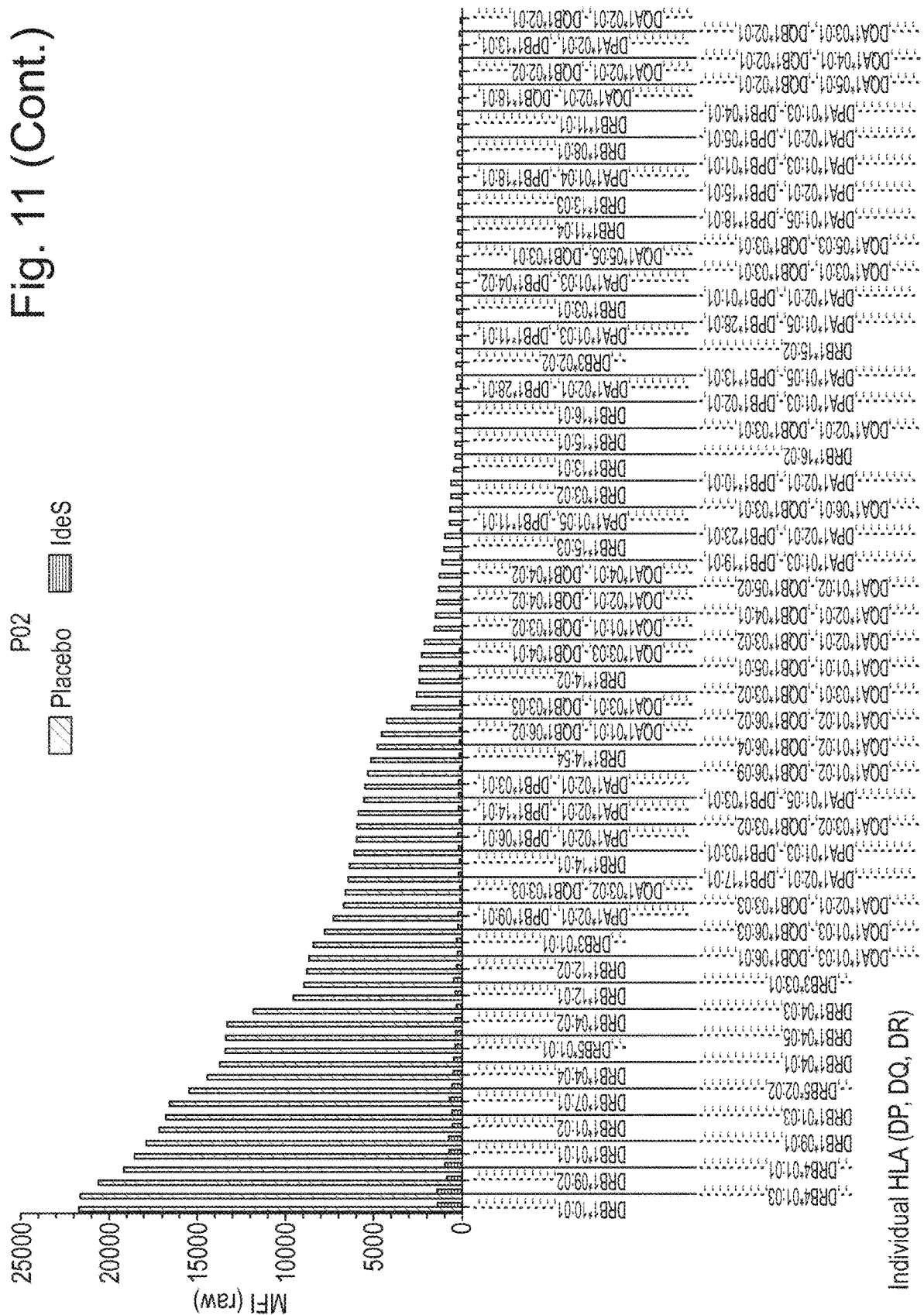

Serum from patient P02 demonstrated CDC-reactivity against T-cells from 4 donors and IdeS treatment could completely neutralize this reactivity (score: 1) (table 2.2). In addition, the pre-treatment serum reacted against 16 out of the 23 B-cell donors and after treatment (reduced) reactivity remained against only two donors (table 2.3) whereas the remaining were negative (score: 1). The SAB analyses demonstrated that before IdeS treatment the patient serum had reactivity (i.e. MFI>1000) against HLA-A, -B and -C antigens as well as HLA-DP, -DQ and -DR antigens (tables 2.4 and 2.5; FIG. 11). IdeS treatment reduced the reactivity against all antigens and very few (i.e. two HLA-DR antigens) had reactivity above MFI: 1000 (non were above MFI: 2000) (table 2.4 and 2.5; FIG. 11). The overall conclusion is that IdeS can close to completely desensitize serum from patient P02.

Patient P04

Figure 12:
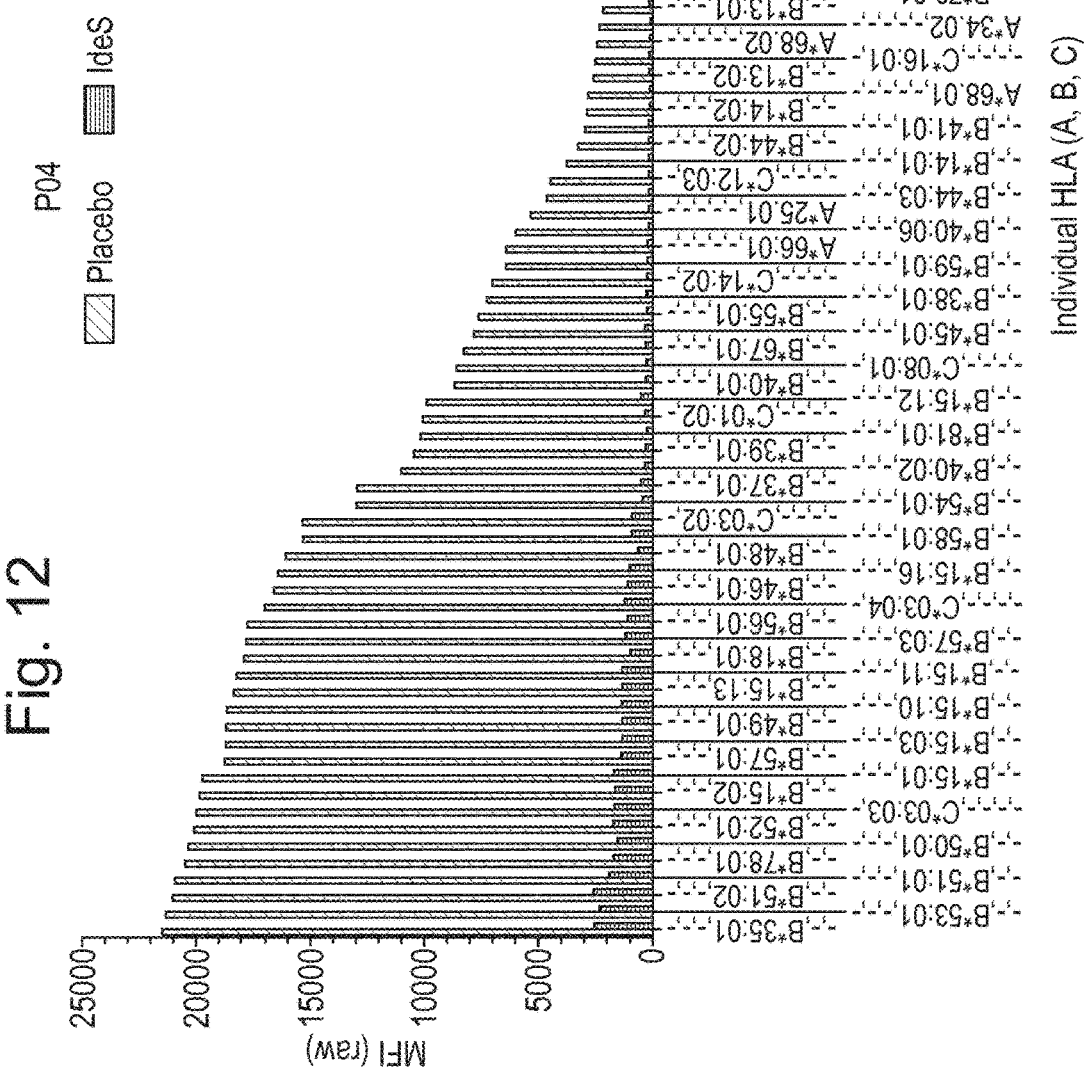
FIGS. 12, 13, 14, 15. Equivalent to FIG. 11 for sensitised patients P04, P07, P08 and P09, respectively.

Serum from patient P04 reacted against five donors in the T cell CDC-test and IdeS treatment could completely neutralize this reactivity (i.e. score: 1) (table 2.2). The MHC class I SAB analyses demonstrated strong reactivity mainly against HLA-B antigens but also against some HLA-A and HLA-C antigens (table 2.4; FIG. 12). After IdeS treatment a reduced but significant reactivity remained against some HLA-B antigens. Noteworthy, donor PC: 17 has the genotype HLA-B*35:01 and the P04 serum reacted strongly in the CDC assay against this donor (table 2.3). Also, in the SAB assay the serum reacted strongly against the HLA-B*35:01 antigen (MFI: 21463) (Appendix-I). However, IdeS treatment completely neutralized the reactivity against the PC: 17 donor (from score 8 to 1) even though the reactivity against the HLA-B*35:01 antigen in the SAB assay was still one of the highest (MFI: 2517).

In the B cell CDC test the serum reacted strongly (i.e. score: 8) against 8 out of the tested 23 donors and IdeS treatment reduced the reactivity against all of these donors (table 3). The serum from patient P04 was positive in the SAB assay against both HLA-DQ and HLA-DR antigens (table 2.5; FIG. 12). However, the IdeS treatment was very effective and after treatment only two of the tested HLA-DR antigens had a significant reactivity. The overall conclusion is that IdeS treatment is highly effective in reducing anti-HLA reactivity in serum from patient P04.

Patient P07

Figure 13:
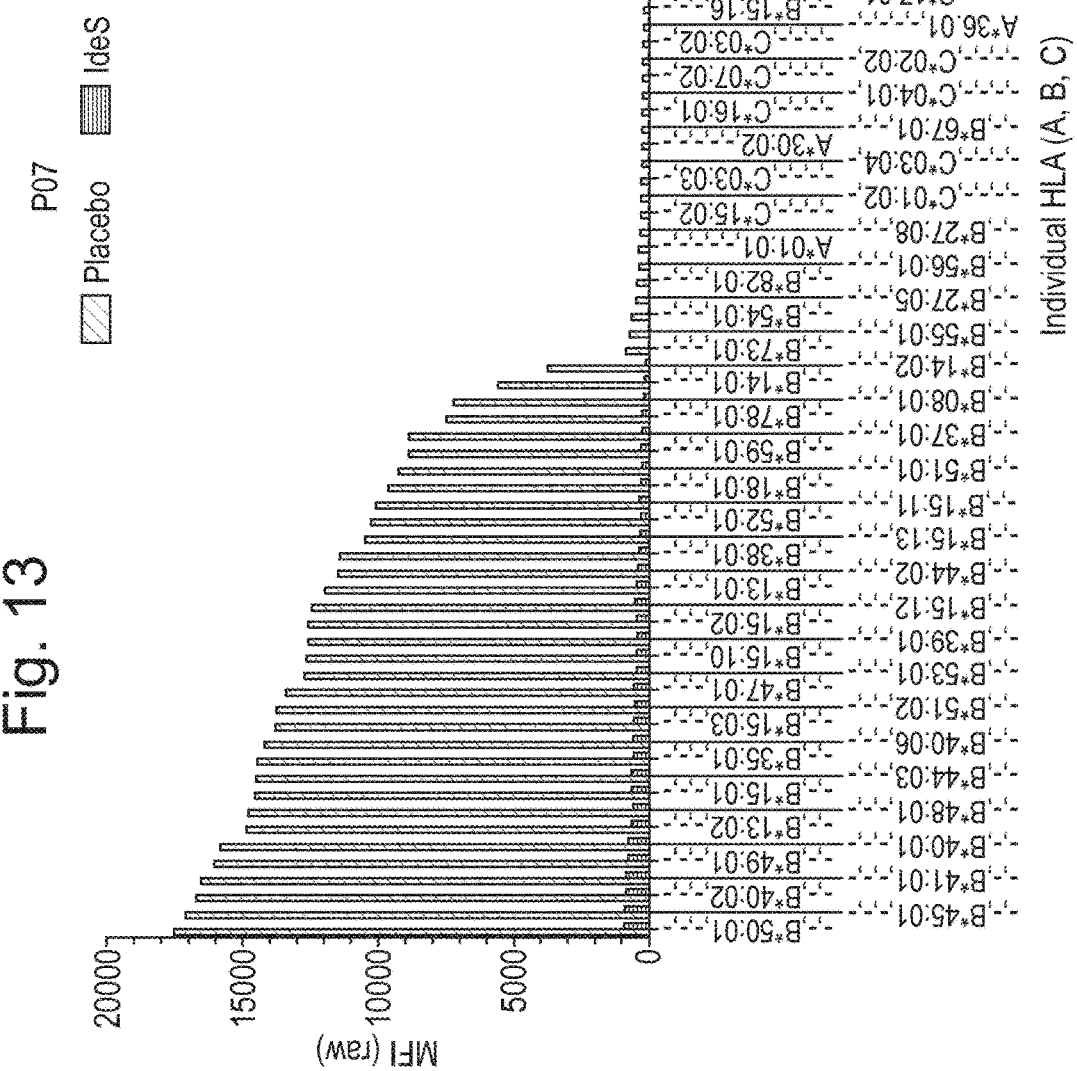
Figure 13:
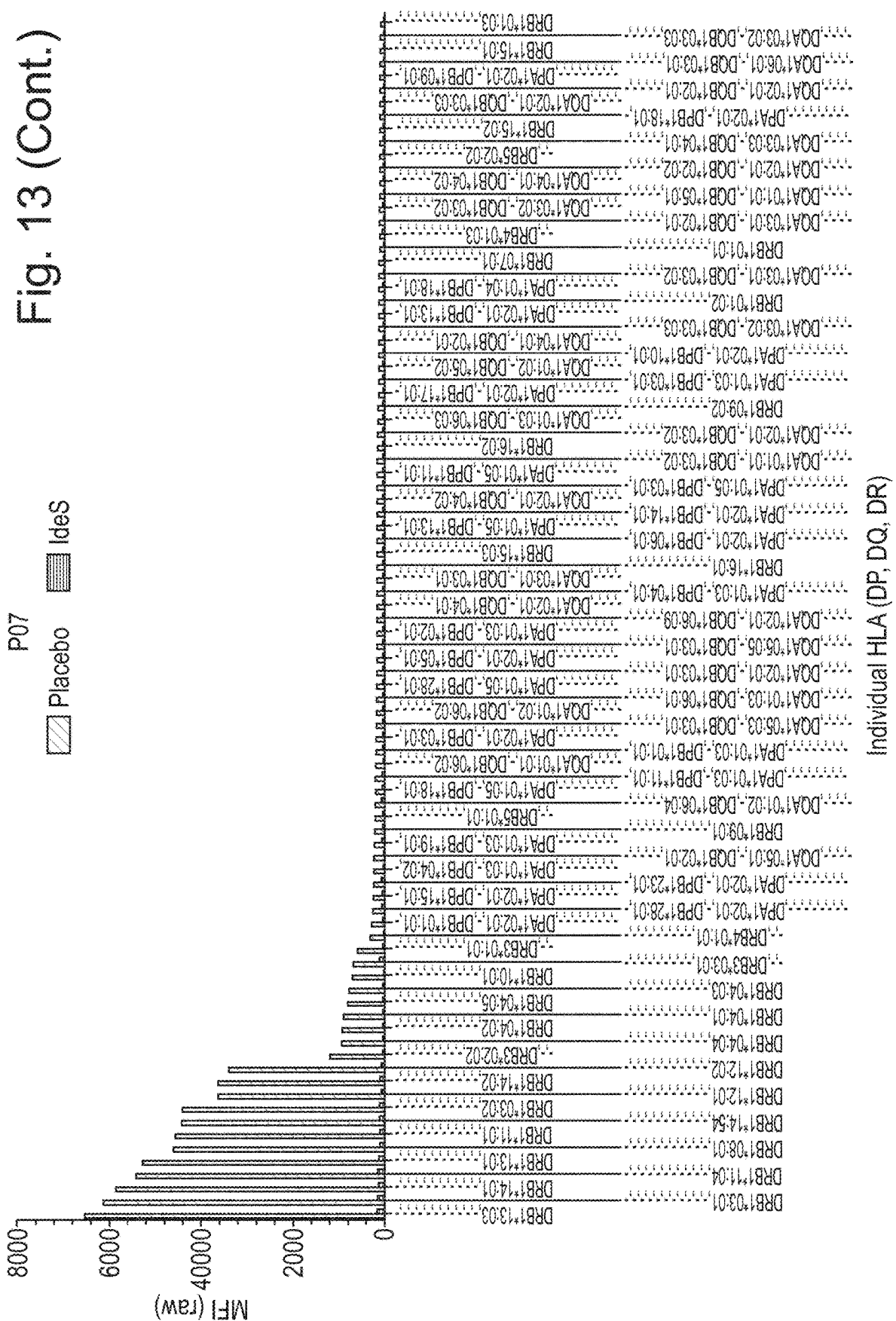

Serum from patient P07 had a broad reactivity in the CDC-test and demonstrated strong reactivity (i.e. CDC-score: 8) against 15 of the 23 tested donors in the T-cell CDC-test. IdeS treatment completely neutralized (i.e. score: 1) the reactivity against all of these 15 donors (table 2.2). The MHC class-I SAB analyses demonstrated strong reactivity against 34 of the tested HLA-B antigens with no reactivity against HLA-A or -C antigens (table 2.5; FIG. 13 and appendix-I). After IdeS treatment no MHC class-I antigens had a significant signal, i.e. the measured MFIs were all below 1000.

In the B cell CDC test the serum reacted strongly (i.e. CDC-score: 8) against 16 out of the tested 23 donors and, with one exception (donor PC: 19), they were the same donors that were strongly positive in the T cell CDC (table 2.2 and 2.3). This indicates that the majority of the reactivity could be attributed to MHC class I reactivity since the B cells are both class-I and -II positive. Interestingly, although IdeS reduced the score against the majority of the tested donors IdeS was not as effective as in the corresponding T cell CDC. There were two donors (PC: 20 and PC: 21) where IdeS completely neutralized the score in the T cell CDC but had no effect in the B cell CDC. Potential explanation for this could be e.g. very high titres against class II antigens or that this patient has significant titres of IgM antibodies to class II antigens. However, the SAB analysis clearly demonstrates that the patient does not have antibodies to HLA-DP or -DQ (table 2.5; FIG. 13 and appendix-II). The patient has low to intermediate (i.e. MFI 1200-6500) reactivity against 13 of the tested HLA-DR antigens and this reactivity is completely neutralized by IdeS treatment (MFI<160). Consequently, it is difficult to explain the remaining reactivity in the B cell test by high titres to class-II antigens. The two donors (PC: 20 and PC: 21) where IdeS treatment had full effect in the T cell CDC but no effect in the B-cell CDC carries the following HLA-DR alleles; PC: 20-DRB1*11:01, DBR3*02:02 and PC: 21-DRB1*01:01, DBR1*16:01:01, DRB5*0202. All of these antigens are present on the SAB array. The serum from patient P07 reacts with intermediate reactivity against DRB1*11:01 (MFI: 4552) and weakly against DBR3*02:02 (MFI: 1203) but after IdeS treatment the signal is below 100 for both antigens. The serum has no reactivity against DRB1*01:01 DRB1*16:01:01 or DRB5*0202 neither before nor after IdeS treatment. The conclusion is that IgG against the MHC class II antigens cannot explain the lack of effect in the B-cell CDC using these donors and it is tempting to speculate that IgM could be involved. The overall conclusion is that IdeS is highly effective in reducing the levels of anti-HLA antibodies in serum from patient P07.

Patient P08

The serum from patient P08 is highly reactive against all tested donors in the T and B cell CDC tests (table 2.2 and 2.3). In the T-cell test there are 14 donors where IdeS can completely neutralize the reactivity and 6 donors where IdeS has no measurable effect. In the B cell test there are 5 donors where IdeS can completely neutralize the reactivity and since IdeS also have full activity in the T-cell test using the same donors it is tempting to attribute this reactivity to being merely MHC class I reactivity. There are a number of donors where IdeS has no effect neither in the T nor the B cell tests or where IdeS has only partial effect in these tests. However, there are also 3 donors (PC: 14, PC: 16 and PC: 20) where IdeS has full effect in the T cell test and no measurable effect in the B cell test.

Figure 14:
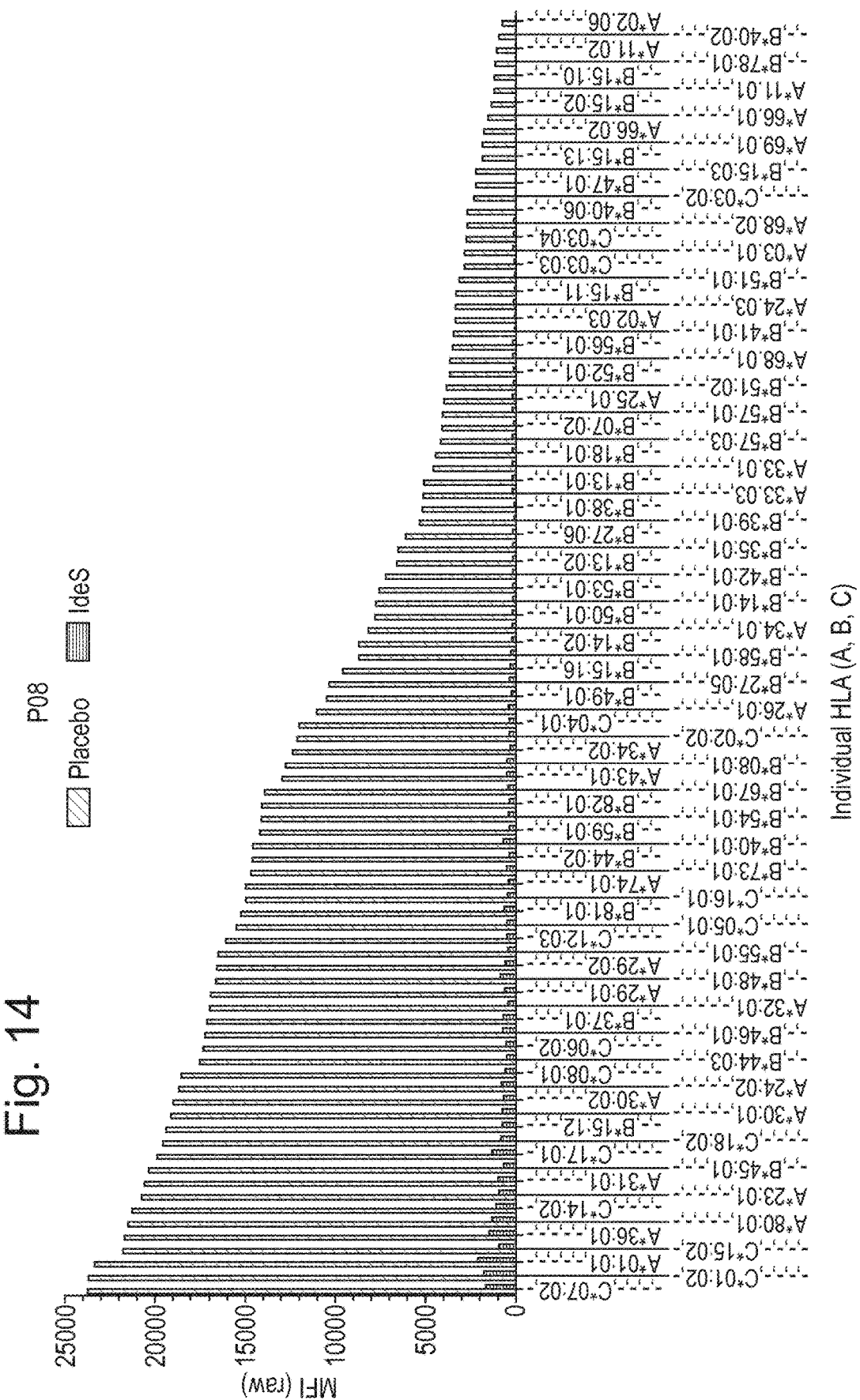
Figure 14:
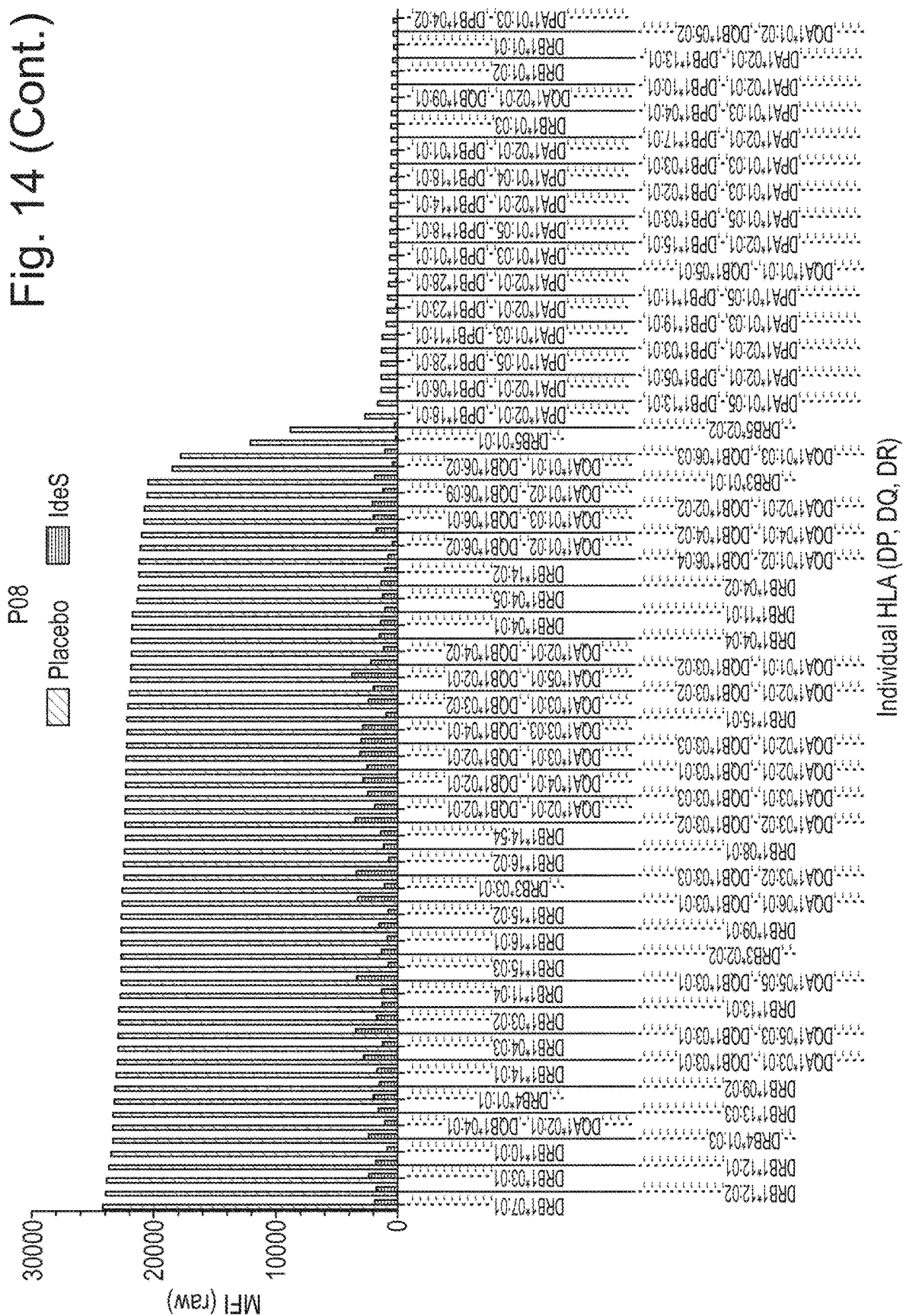

The SAB analyses clearly demonstrate that patient P08 has antibodies to HLA-A, -B and -C as well as HLA-DP, -DQ and -DR. Before IdeS treatment the serum has the broadest reactivity among the tested sera (tables 2.4 and 2.5; FIG. 14). In addition, the SAB analyses indicate that the patient has the highest titres of anti-HLA antibodies (FIG. 15 and Appendixes I and II) among the tested patients. IdeS can clearly reduce the levels of MHC class I and class II antibodies although the reactivity is still significant (i.e. MFI>1000) to a rather high proportion of HLA-DQ and -DR antigens after treatment. It is noteworthy that IdeS was least effective in the P08 serum when measuring remaining total IgG (0.4 g/L) and this is naturally reflected in the level of remaining anti-HLA antibodies.

Patient P09

Figure 15:
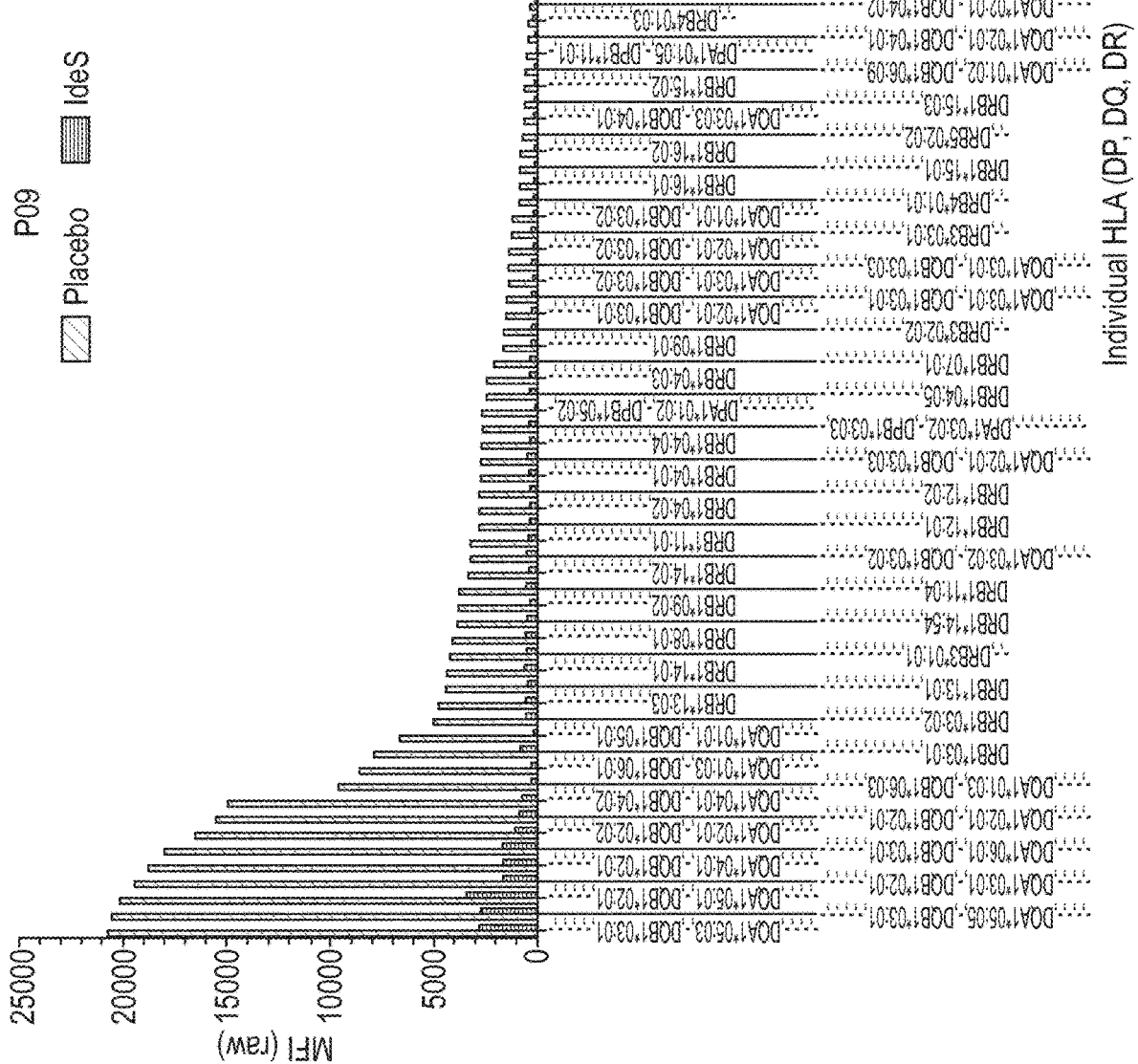

The serum from patient P09 had strong CDC-reactivity (i.e. CDC-score: 8) against T cells from 7 donors and IdeS treatment could completely neutralize this reactivity (table 2.2). In addition, the serum reacted against 22 out of the 23 B-cell donors and after treatment (reduced) reactivity remained against 6 donors (table 2.3). The SAB analyses demonstrated that before IdeS treatment the patient serum had reactivity (i.e. MFI>1000) mainly against HLA-A-antigens as well as HLA-DQ and -DR antigens (tables 2.4 and 2.5; FIG. 15). IdeS reduced the reactivity against all antigens and only a few HLA-DQ antigens had reactivity above MFI: 1000 after treatment. The overall conclusion is that IdeS can close to completely desensitize serum from patient P09.

Conclusions

Treatment of sera from sensitized patients suffering from stage 5 CKD using a clinically relevant dose of IdeS could rapidly and substantially reduce the level of total-IgG. Furthermore, this activity was directly reflected in a reduction in the levels of specific and/or broad-reactive anti-HLA IgG in serum from these patients. SAB analyses clearly demonstrated that IdeS treatment reduced the level of IgG-antibodies to all MHC-antigens tested positive in serum from all analyzed patients. In the majority of cases the reactivity to individual MHC-antigens after IdeS treatment was below the critical MFI, i.e. below 1000. In CDC-CXM against T and B cells from hypothetical donors IdeS could reduce the reactivity in all tested patient serum samples and had the capacity to turn a positive cross-match into a negative. Furthermore, serum collected from healthy subjects before treatment with 0.24 mg/kg IdeS reacted strongly in CDC-CXM against mouse target cells, whereas serum collected two and 24 hours after IdeS-treatment were negative, which further proves that IdeS-treatment has the capacity turn a positive CXM negative. Taken together the data presented here clearly show that IdeS treatment just prior to transplantation has the potential to desensitize a highly sensitized patient, thereby allowing transplantation and avoiding an acute antibody mediated rejection.

EXAMPLE 2—APPENDIX I-MFI RAW DATA—MHC CLASS-I ANTIGENS

TABLE A

MFI (raw) against individual HLA-A antigens measured using SAB assay.

| Allele specificity | P02 +PBS | P02 +IdeS | P04 +PBS | P04 +IdeS | P07 +PBS | P07 +IdeS | P08 +PBS | P08 +IdeS | P09 +PBS | P09 +IdeS |
|---|---|---|---|---|---|---|---|---|---|---|
| A*01:01, -, -, -, -, - | 64 | 12 | 258 | 19 | 368 | 16 | 23322 | 2047 | 3670 | 131 |
| A*11:02, -, -, -, -, - | 76 | 12 | 1170 | 38 | 155 | 28 | 1012 | 46 | 647 | 30 |
| A*11:01, -, -, -, -, - | 95 | 14 | 772 | 34 | 117 | 17 | 1127 | 40 | 332 | 30 |
| A*02:01, -, -, -, -, - | 14010 | 754 | 471 | 28 | 123 | 16 | 377 | 25 | 4416 | 176 |
| A*02:06, -, -, -, -, - | 13081 | 724 | 419 | 27 | 119 | 16 | 682 | 29 | 4549 | 184 |
| A*02:03, -, -, -, -, - | 14679 | 848 | 336 | 22 | 93 | 12 | 3313 | 54 | 6714 | 266 |
| A*23:01, -, -, -, -, - | 6931 | 184 | 140 | 21 | 170 | 18 | 20719 | 892 | 3438 | 118 |
| A*24:02, -, -, -, -, - | 5720 | 163 | 146 | 22 | 167 | 19 | 18660 | 747 | 6522 | 261 |
| A*24:03, -, -, -, -, - | 7963 | 218 | 147 | 23 | 134 | 17 | 3296 | 118 | 4950 | 171 |
| A*25:01, -, -, -, -, - | 16017 | 708 | 5330 | 154 | 116 | 15 | 3941 | 110 | 214 | 29 |
| A*26:01, -, -, -, -, - | 70 | 15 | 1792 | 50 | 156 | 19 | 11061 | 359 | 230 | 33 |
| A*29:01, -, -, -, -, - | 237 | 19 | 498 | 46 | 179 | 20 | 16918 | 574 | 1055 | 67 |
| A*29:02, -, -, -, -, - | 347 | 23 | 405 | 39 | 174 | 22 | 16535 | 551 | 763 | 53 |
| A*03:01, -, -, -, -, - | 481 | 19 | 180 | 22 | 104 | 15 | 2809 | 114 | 98 | 24 |
| A*30:01, -, -, -, -, - | 99 | 14 | 155 | 21 | 131 | 16 | 19053 | 697 | 181 | 26 |
| A*30:02, -, -, -, -, - | 96 | 11 | 167 | 17 | 219 | 13 | 18951 | 642 | 156 | 25 |
| A*31:01, -, -, -, -, - | 108 | 13 | 191 | 21 | 126 | 15 | 20556 | 975 | 1473 | 48 |
| A*32:01, -, -, -, -, - | 15853 | 659 | 490 | 36 | 154 | 22 | 16963 | 377 | 378 | 41 |
| A*33:03, -, -, -, -, - | 130 | 17 | 1432 | 47 | 114 | 22 | 5081 | 140 | 7330 | 243 |
| A*33:01, -, -, -, -, - | 2084 | 40 | 297 | 25 | 117 | 18 | 4557 | 125 | 3851 | 101 |
| A*34:02, -, -, -, -, - | 115 | 13 | 2330 | 63 | 147 | 15 | 12354 | 241 | 4128 | 130 |
| A*34:01, -, -, -, -, - | 122 | 17 | 989 | 49 | 152 | 20 | 8166 | 164 | 3602 | 99 |
| A*36:01, -, -, -, -, - | 97 | 13 | 258 | 26 | 190 | 19 | 21627 | 1463 | 1139 | 54 |
| A*43:01, -, -, -, -, - | 169 | 19 | 1343 | 55 | 158 | 22 | 12911 | 445 | 304 | 33 |
| A*66:02, -, -, -, -, - | 130 | 15 | 256 | 29 | 155 | 22 | 1733 | 51 | 4878 | 163 |
| A*66:01, -, -, -, -, - | 107 | 16 | 6368 | 171 | 130 | 17 | 1510 | 47 | 2815 | 87 |
| A*68:02, -, -, -, -, - | 3975 | 131 | 2415 | 80 | 166 | 18 | 2659 | 93 | 12805 | 656 |

TABLE A-continued

MFI (raw) against individual HLA-A antigens measured using SAB assay.

| | P02 | | P04 | | P07 | | P08 | | P09 | |
|---|---|---|---|---|---|---|---|---|---|---|
| Allele specificity | +PBS | +IdeS | +PBS | +IdeS | +PBS | +IdeS | +PBS | +IdeS | +PBS | +IdeS |
| A*68:01, -, -, -, -, - | 3940 | 124 | 2818 | 75 | 167 | 18 | 3653 | 110 | 13413 | 665 |
| A*69:01, -, -, -, -, - | 10448 | 484 | 280 | 26 | 132 | 20 | 1798 | 55 | 12645 | 611 |
| A*74:01, -, -, -, -, - | 107 | 13 | 271 | 26 | 115 | 16 | 14934 | 338 | 722 | 38 |
| A*80:01, -, -, -, -, - | 82 | 14 | 279 | 27 | 182 | 19 | 21455 | 1273 | 3102 | 76 |
| | | | | | | | | | | |
| Sum | 117431 | 5325 | 32402 | 1349 | 4728 | 564 | 311736 | 12941 | 110522 | 4671 |
| Reactivity (%) | 100% | 5% | 100% | 4% | 100% | 12% | 100% | 4% | 100% | 4% |

TABLE B

MFI (raw) against individual HLA-B antigens measured using SAB assay.

| | P02 | | P04 | | P07 | | P08 | | P09 | |
|---|---|---|---|---|---|---|---|---|---|---|
| Allele specificity | +PBS | +IdeS | +PBS | +IdeS | +PBS | +IdeS | +PBS | +IdeS | +PBS | +IdeS |
| -, -, B*13:01, -, -, - | 6568 | 239 | 2156 | 96 | 11940 | 415 | 5049 | 134 | 612 | 52 |
| -, -, B*13:02, -, -, - | 10690 | 467 | 2597 | 102 | 14834 | 625 | 6532 | 140 | 602 | 43 |
| -, -, B*18:01, -, -, - | 13289 | 640 | 17859 | 955 | 9574 | 282 | 4412 | 116 | 1011 | 64 |
| -, -, B*27:05, -, -, - | 82 | 12 | 156 | 23 | 471 | 17 | 10312 | 295 | 609 | 36 |
| -, -, B*27:08, -, -, - | 74 | 13 | 152 | 21 | 283 | 18 | 6053 | 120 | 288 | 29 |
| -, -, B*35:01, -, -, - | 14040 | 735 | 21463 | 2517 | 14472 | 566 | 6441 | 146 | 175 | 62 |
| -, -, B*37:01, -, -, - | 6773 | 187 | 12918 | 476 | 8835 | 228 | 17098 | 655 | 206 | 60 |
| -, -, B*38:01, -, -, - | 14695 | 712 | 7209 | 189 | 11384 | 337 | 5136 | 90 | 307 | 55 |
| -, -, B*39:01, -, -, - | 625 | 21 | 10465 | 304 | 12569 | 424 | 5273 | 77 | 177 | 33 |
| -, -, B*41:01, -, -, - | 1423 | 40 | 2978 | 89 | 16496 | 839 | 3424 | 78 | 128 | 33 |
| -, -, B*42:01, -, -, - | 1565 | 51 | 422 | 29 | 123 | 16 | 7160 | 174 | 128 | 33 |
| -, -, B*44:03, -, -, - | 7408 | 286 | 4611 | 151 | 14513 | 614 | 17506 | 446 | 1576 | 62 |
| -, -, B*44:02, -, -, - | 12112 | 541 | 3225 | 108 | 11467 | 396 | 14585 | 306 | 318 | 52 |
| -, -, B*45:01, -, -, - | 905 | 25 | 7774 | 291 | 17110 | 907 | 20330 | 605 | 462 | 48 |
| -, -, B*46:01, -, -, - | 4880 | 123 | 16562 | 1035 | 169 | 30 | 17200 | 673 | 222 | 79 |
| -, -, B*47:01, -, -, - | 1700 | 41 | 1045 | 56 | 13404 | 535 | 2187 | 62 | 1193 | 58 |
| -, -, B*48:01, -, -, - | 2621 | 53 | 16060 | 597 | 14815 | 569 | 16613 | 811 | 1493 | 78 |
| -, -, B*49:01, -, -, - | 19412 | 1338 | 18626 | 1265 | 16059 | 743 | 10511 | 178 | 169 | 53 |
| -, -, B*50:01, -, -, - | 8854 | 343 | 20304 | 1509 | 17500 | 932 | 7763 | 155 | 121 | 48 |
| -, -, B*51:01, -, -, - | 19766 | 1510 | 20906 | 1895 | 9227 | 240 | 3099 | 72 | 159 | 73 |
| -, -, B*51:02, -, -, - | 20506 | 1611 | 20995 | 2547 | 13718 | 515 | 3801 | 86 | 183 | 87 |
| -, -, B*52:01, -, -, - | 19436 | 1585 | 20028 | 1726 | 10231 | 275 | 3682 | 71 | 160 | 61 |
| -, -, B*53:01, -, -, - | 18707 | 1261 | 21303 | 2272 | 12708 | 410 | 7582 | 160 | 267 | 86 |
| -, -, B*54:01, -, -, - | 770 | 28 | 12971 | 405 | 632 | 28 | 14088 | 316 | 835 | 71 |
| -, -, B*55:01, -, -, - | 2044 | 64 | 7628 | 186 | 691 | 22 | 16497 | 397 | 162 | 39 |
| -, -, B*56:01, -, -, - | 6751 | 224 | 17712 | 1039 | 385 | 22 | 3469 | 110 | 247 | 43 |
| -, -, B*57:03, -, -, - | 18455 | 1192 | 17761 | 1170 | 150 | 24 | 4147 | 107 | 274 | 59 |
| -, -, B*57:01, -, -, - | 19337 | 1338 | 18733 | 1350 | 136 | 21 | 4007 | 110 | 342 | 58 |
| -, -, B*58:01, -, -, - | 16725 | 911 | 15316 | 856 | 170 | 23 | 8670 | 196 | 294 | 55 |
| -, -, B*59:01, -, -, - | 15856 | 819 | 6399 | 177 | 8852 | 274 | 14144 | 330 | 653 | 80 |
| -, -, B*40:01, -, -, - | 372 | 19 | 8620 | 267 | 15827 | 738 | 14576 | 630 | 735 | 42 |
| -, -, B*40:02, -, -, - | 318 | 17 | 10941 | 289 | 16694 | 856 | 890 | 34 | 1354 | 55 |
| -, -, B*40:06, -, -, - | 304 | 26 | 5967 | 119 | 14189 | 594 | 2623 | 69 | 1283 | 60 |
| -, -, B*15:01, -, -, - | 9919 | 349 | 19678 | 1672 | 14553 | 640 | 529 | 33 | 337 | 63 |
| -, -, B*15:16, -, -, - | 17630 | 1094 | 16364 | 993 | 190 | 27 | 9578 | 210 | 199 | 63 |
| -, -, B*14:01, -, -, - | 7479 | 218 | 3726 | 105 | 5556 | 136 | 7704 | 162 | 292 | 62 |
| -, -, B*14:02, -, -, - | 8348 | 280 | 2889 | 81 | 3724 | 102 | 8668 | 175 | 256 | 68 |
| -, -, B*67:01, -, -, - | 1276 | 50 | 8260 | 329 | 219 | 30 | 13904 | 365 | 393 | 65 |
| -, -, B*07:02, -, -, - | 79 | 12 | 221 | 23 | 129 | 14 | 4083 | 89 | 93 | 29 |
| -, -, B*15:10, -, -, - | 10301 | 389 | 18614 | 1329 | 12626 | 454 | 1122 | 46 | 262 | 77 |
| -, -, B*15:03, -, -, - | 8867 | 311 | 18677 | 1297 | 13782 | 579 | 2173 | 38 | 126 | 48 |
| -, -, B*73:01, -, -, - | 95 | 16 | 1842 | 65 | 825 | 32 | 14648 | 466 | 789 | 51 |
| -, -, B*15:11, -, -, - | 10379 | 411 | 18185 | 1319 | 10037 | 356 | 3259 | 78 | 286 | 79 |
| -, -, B*15:02, -, -, - | 11482 | 478 | 19823 | 1615 | 12558 | 423 | 1327 | 39 | 287 | 59 |
| -, -, B*15:12, -, -, - | 2830 | 54 | 9906 | 508 | 12454 | 501 | 19323 | 713 | 843 | 52 |
| -, -, B*15:13, -, -, - | 18141 | 1108 | 18294 | 1317 | 10436 | 287 | 1812 | 55 | 241 | 69 |
| -, -, B*78:01, -, -, - | 15049 | 865 | 20478 | 1730 | 7461 | 217 | 1111 | 38 | 116 | 61 |
| -, -, B*08:01, -, -, - | 1581 | 36 | 168 | 23 | 7192 | 163 | 12749 | 426 | 181 | 35 |
| -, -, B*81:01, -, -, - | 81 | 13 | 10132 | 236 | 134 | 17 | 15231 | 590 | 1194 | 54 |
| -, -, B*82:01, -, -, - | 166 | 21 | 407 | 28 | 439 | 24 | 14058 | 267 | 227 | 47 |
| | | | | | | | | | | |
| Sum | 410769 | 22178 | 559523 | 36782 | 421945 | 16539 | 416138 | 11738 | 22865 | 2830 |
| Reactivity (%) | 100% | 5% | 100% | 7% | 100% | 4% | 100% | 3% | 100% | 12% |

TABLE C

MFI (raw) against individual HLA-C antigens measured using SAB assay.

| Allele specificity | P02 +PBS | P02 +IdeS | P04 +PBS | P04 +IdeS | P07 +PBS | P07 +Ides | P08 +PBS | P08 +IdeS | P09 +PBS | P09 +IdeS |
|---|---|---|---|---|---|---|---|---|---|---|
| -, -, -, -, C*01:02, - | 144 | 27 | 10024 | 280 | 275 | 27 | 23683 | 1730 | 2036 | 89 |
| -, -, -, -, C*03:02, - | 4722 | 140 | 15280 | 894 | 193 | 32 | 2261 | 65 | 131 | 41 |
| -, -, -, -, C*03:04, - | 2668 | 75 | 16963 | 1176 | 222 | 31 | 2719 | 85 | 153 | 46 |
| -, -, -, -, C*12:03, - | 148 | 25 | 4439 | 133 | 166 | 24 | 16059 | 463 | 479 | 42 |
| -, -, -, -, C*14:02, - | 122 | 32 | 6994 | 177 | 166 | 29 | 21253 | 1035 | 780 | 51 |
| -, -, -, -, C*15:02, - | 5524 | 181 | 1606 | 70 | 277 | 34 | 21755 | 859 | 953 | 56 |
| -, -, -, -, C*16:01, - | 141 | 29 | 2493 | 97 | 217 | 37 | 14945 | 414 | 347 | 64 |
| -, -, -, -, C*17:01, - | 181 | 36 | 228 | 34 | 189 | 37 | 19817 | 1256 | 231 | 45 |
| -, -, -, -, C*18:02, - | 159 | 31 | 1037 | 50 | 188 | 32 | 19501 | 786 | 651 | 61 |
| -, -, -, -, C*02:02, - | 186 | 28 | 239 | 32 | 198 | 31 | 12090 | 269 | 558 | 50 |
| -, -, -, -, C*04:01, - | 186 | 38 | 337 | 37 | 209 | 37 | 11939 | 315 | 293 | 49 |
| -, -, -, -, C*05:01, - | 164 | 26 | 1046 | 42 | 177 | 28 | 15526 | 424 | 435 | 46 |
| -, -, -, -, C*06:02, - | 170 | 32 | 1701 | 62 | 169 | 31 | 17296 | 491 | 598 | 50 |
| -, -, -, -, C*07:02, - | 173 | 33 | 396 | 37 | 204 | 31 | 23743 | 1643 | 599 | 54 |
| -, -, -, -, C*08:01, - | 145 | 21 | 8555 | 244 | 155 | 25 | 18497 | 558 | 650 | 49 |
| -, -, -, -, C*03:03, - | 2107 | 59 | 19947 | 1599 | 270 | 35 | 2816 | 84 | 148 | 64 |
| Sum | 16941 | 812 | 91284 | 4964 | 3274 | 500 | 243901 | 10477 | 9039 | 856 |
| Reactivity (%) | 100% | 5% | 100% | 5% | 100% | 15% | 100% | 4% | 100% | 9% |

EXAMPLE 2—APPENDIX II—MFI RAW DATA-MHC CLASS-II ANTIGENS

TABLE D

MFI (raw) against individual HLA-DP antigens measured using SAB assay.

| Allele specificity | P02 +PBS | P02 +Ides | P04 +PBS | P04 +IdeS | P07 +PBS | P07 +Ides | P08 +PBS | P08 +IdeS | P09 +PBS | P09 +Ides |
|---|---|---|---|---|---|---|---|---|---|---|
| -, -, -, -, -, -, -, -, DPA1*02:01, -, DPB1*01:01, - | 256 | 28 | 426 | 45 | 273 | 32 | 499 | 31 | 177 | 42 |
| -, -, -, -, -, -, -, -, DPA1*01:03, -, DPB1*01:01, - | 184 | 35 | 215 | 39 | 175 | 36 | 649 | 35 | 156 | 43 |
| -, -, -, -, -, -, -, -, DPA1*02:01, -, DPB1*10:01, - | 591 | 26 | 253 | 32 | 122 | 23 | 439 | 27 | 97 | 34 |
| -, -, -, -, -, -, -, -, DPA1*01:05, -, DPB1*11:01, - | 707 | 39 | 367 | 41 | 144 | 33 | 773 | 47 | 509 | 49 |
| -, -, -, -, -, -, -, -, DPA1*01:03, -, DPB1*11:01, - | 283 | 42 | 434 | 56 | 184 | 41 | 1252 | 59 | 234 | 66 |
| -, -, -, -, -, -, -, -, DPA1*01:05, -, DPB1*13:01, - | 303 | 39 | 323 | 46 | 148 | 43 | 1576 | 57 | 252 | 52 |
| -, -, -, -, -, -, -, -, DPA1*02:01, -, DPB1*13:01, - | 123 | 22 | 152 | 26 | 115 | 24 | 380 | 26 | 99 | 29 |
| -, -, -, -, -, -, -, -, DPA1*02:01, -, DPB1*14:01, - | 5844 | 156 | 305 | 40 | 148 | 30 | 558 | 31 | 115 | 33 |
| -, -, -, -, -, -, -, -, DPA1*02:01, -, DPB1*15:01, - | 198 | 37 | 571 | 103 | 236 | 53 | 583 | 66 | 172 | 87 |
| -, -, -, -, -, -, -, -, DPA1*02:01, -, DPB1*17:01, - | 6441 | 177 | 291 | 34 | 128 | 25 | 498 | 29 | 295 | 40 |
| -, -, -, -, -, -, -, -, DPA1*02:01, -, DPB1*18:01, - | 155 | 21 | 188 | 33 | 94 | 24 | 2631 | 21 | 94 | 29 |
| -, -, -, -, -, -, -, -, DPA1*01:04, -, DPB1*18:01, - | 189 | 26 | 260 | 42 | 114 | 28 | 506 | 55 | 219 | 39 |
| -, -, -, -, -, -, -, -, DPA1*01:05, -, DPB1*18:01, - | 213 | 28 | 529 | 69 | 184 | 34 | 575 | 40 | 151 | 48 |
| -, -, -, -, -, -, -, -, DPA1*01:03, -, DPB1*19:01, - | 1084 | 64 | 921 | 147 | 216 | 51 | 920 | 55 | 183 | 64 |
| -, -, -, -, -, -, -, -, DPA1*01:03, -, DPB1*02:01, - | 308 | 32 | 324 | 118 | 158 | 35 | 531 | 37 | 156 | 43 |
| -, -, -, -, -, -, -, -, DPA1*02:01, -, DPB1*23:01, - | 914 | 80 | 457 | 72 | 235 | 73 | 791 | 70 | 210 | 89 |
| -, -, -, -, -, -, -, -, DPA1*02:01, -, DPB1*28:01, - | 306 | 58 | 414 | 83 | 240 | 57 | 669 | 67 | 182 | 71 |
| -, -, -, -, -, -, -, -, DPA1*01:05, -, DPB1*28:01, - | 283 | 38 | 373 | 60 | 166 | 40 | 1303 | 38 | 137 | 49 |
| -, -, -, -, -, -, -, -, DPA1*01:05, -, DPB1*03:01, - | 5508 | 155 | 315 | 44 | 145 | 34 | 563 | 38 | 204 | 47 |

TABLE D-continued

MFI (raw) against individual HLA-DP antigens measured using SAB assay.

| Allele specificity | P02 +PBS | P02 +Ides | P04 +PBS | P04 +IdeS | P07 +PBS | P07 +Ides | P08 +PBS | P08 +Ides | P09 +PBS | P09 +Ides |
|---|---|---|---|---|---|---|---|---|---|---|
| -, -, -, -, -, -, -, -, DPA1*01:03, -, DPB1*03:01, - | 6101 | 168 | 284 | 39 | 124 | 28 | 502 | 29 | 209 | 38 |
| -, -, -, -, -, -, -, -, DPA1*02:01, -, DPB1*03:01, - | 5481 | 148 | 352 | 46 | 173 | 34 | 1259 | 43 | 128 | 42 |
| -, -, -, -, -, -, -, -, DPA1*01:03, -, DPB1*04:02, - | 250 | 27 | 613 | 72 | 232 | 24 | 317 | 41 | 127 | 54 |
| -, -, -, -, -, -, -, -, DPA1*01:03, -, DPB1*04:01, - | 156 | 18 | 359 | 43 | 152 | 37 | 474 | 28 | 90 | 36 |
| -, -, -, -, -, -, -, -, DPA1*02:01, -, DPB1*05:01, - | 170 | 28 | 265 | 37 | 162 | 31 | 1319 | 41 | 173 | 39 |
| -, -, -, -, -, -, -, -, DPA1*02:01, -, DPB1*06:01, - | 5980 | 162 | 373 | 42 | 149 | 35 | 1342 | 42 | 359 | 55 |
| -, -, -, -, -, -, -, -, DPA1*02:01, -, DPB1*09:01, - | 7300 | 220 | 186 | 24 | 89 | 19 | 452 | 19 | 77 | 23 |
| Sum | 49327 | 1874 | 9549 | 1435 | 4306 | 924 | 21360 | 1073 | 4806 | 1242 |
| Reactivity (%) | 100% | 4% | 100% | 15% | 100% | 21% | 100% | 5% | 100% | 26% |

TABLE E

MFI (raw) against individual HLA-DQ antigens measured using SAB assay.

| Allele specificity | P02 +PBS | P02 +IdeS | P04 +PBS | P04 +IdeS | P07 +PBS | P07 +IdeS | P08 +PBS | P08 +IdeS | P09 +PBS | P09 +IdeS |
|---|---|---|---|---|---|---|---|---|---|---|
| -, -, -, -, DQA1*05:01, -, DQB1*02:01, -, -, -, -, - | 133 | 15 | 147 | 20 | 221 | 20 | 21824 | 3652 | 20118 | 3389 |
| -, -, -, -, DQA1*02:01, -, DQB1*02:02, -, -, -, -, - | 127 | 18 | 5588 | 206 | 99 | 23 | 20701 | 2023 | 16486 | 1044 |
| -, -, -, -, DQA1*02:01, -, DQB1*02:01, -, -, -, -, - | 112 | 14 | 4347 | 161 | 92 | 17 | 22333 | 1826 | 15483 | 844 |
| -, -, -, -, DQA1*04:01, -, DQB1*02:01, -, -, -, -, - | 124 | 23 | 162 | 26 | 120 | 26 | 22318 | 2785 | 18755 | 1598 |
| -, -, -, -, DQA1*03:01, -, DQB1*02:01, -, -, -, -, - | 114 | 18 | 112 | 18 | 103 | 20 | 22232 | 3023 | 19425 | 1575 |
| -, -, -, -, DQA1*02:01, -, DQB1*04:02, -, -, -, -, - | 1331 | 49 | 5717 | 212 | 145 | 28 | 21762 | 1109 | 374 | 60 |
| -, -, -, -, DQA1*02:01, -, DQB1*04:01, -, -, -, -, - | 1473 | 49 | 5509 | 175 | 157 | 31 | 23347 | 1009 | 453 | 59 |
| -, -, -, -, DQA1*04:01, -, DQB1*04:02, -, -, -, -, - | 1235 | 43 | 220 | 26 | 102 | 20 | 20977 | 1724 | 14869 | 702 |
| -, -, -, -, DQA1*03:03, -, DQB1*04:01, -, -, -, -, - | 2215 | 69 | 243 | 30 | 97 | 24 | 22189 | 2769 | 636 | 139 |
| -, -, -, -, DQA1*01:02, -, DQB1*05:02, -, -, -, -, - | 1250 | 52 | 191 | 25 | 122 | 27 | 331 | 29 | 2641 | 69 |
| -, -, -, -, DQA1*01:01, -, DQB1*05:01, -, -, -, -, - | 2344 | 78 | 266 | 24 | 102 | 21 | 660 | 19 | 6670 | 146 |
| -, -, -, -, DQA1*01:01, -, DQB1*06:02, -, -, -, -, - | 4501 | 77 | 281 | 34 | 182 | 25 | 18442 | 380 | 234 | 47 |
| -, -, -, -, DQA1*01:03, -, DQB1*06:03, -, -, -, -, - | 7767 | 181 | 286 | 32 | 136 | 38 | 17789 | 983 | 9668 | 281 |
| -, -, -, -, DQA1*01:02, -, DQB1*06:04, -, -, -, -, - | 4760 | 127 | 280 | 59 | 192 | 55 | 21132 | 724 | 357 | 115 |
| -, -, -, -, DQA1*01:02, -, DQB1*06:09, -, -, -, -, - | 5321 | 100 | 164 | 25 | 158 | 24 | 20512 | 1107 | 543 | 103 |
| -, -, -, -, DQA1*01:02, -, DQB1*06:02, -, -, -, -, - | 4236 | 68 | 234 | 37 | 169 | 31 | 21040 | 358 | 189 | 46 |
| -, -, -, -, DQA1*01:03, -, DQB1*06:01, -, -, -, -, - | 8661 | 192 | 304 | 25 | 167 | 35 | 20774 | 1892 | 8624 | 290 |
| -, -, -, -, DQA1*02:01, -, DQB1*03:01, -, -, -, -, - | 328 | 27 | 7971 | 330 | 164 | 31 | 22290 | 2390 | 1494 | 234 |
| -, -, -, -, DQA1*06:01, -, DQB1*03:01, -, -, -, -, - | 642 | 21 | 203 | 18 | 89 | 17 | 22598 | 3231 | 17969 | 1575 |
| -, -, -, -, DQA1*03:01, -, DQB1*03:01, -, -, -, -, - | 225 | 37 | 325 | 145 | 151 | 30 | 22928 | 2696 | 1477 | 274 |
| -, -, -, -, DQA1*05:03, -, DQB1*03:01, -, -, -, -, - | 216 | 22 | 594 | 37 | 169 | 27 | 22888 | 3371 | 20671 | 2742 |
| -, -, -, -, DQA1*05:05, -, DQB1*03:01, -, -, -, -, - | 222 | 26 | 529 | 35 | 161 | 27 | 22683 | 3319 | 20511 | 2678 |
| -, -, -, -, DQA1*02:01, -, DQB1*03:02, -, -, -, -, - | 2123 | 46 | 5785 | 212 | 141 | 30 | 21968 | 1912 | 1342 | 197 |
| -, -, -, -, DQA1*01:01, -, DQB1*03:02, -, -, -, -, - | 1509 | 41 | 195 | 32 | 143 | 30 | 21810 | 2125 | 1192 | 204 |
| -, -, -, -, DQA1*03:01, -, DQB1*03:02, -, -, -, -, - | 2522 | 39 | 158 | 23 | 109 | 22 | 22088 | 2364 | 1367 | 222 |
| -, -, -, -, DQA1*03:02, -, DQB1*03:02, -, -, -, -, - | 5925 | 85 | 145 | 24 | 102 | 28 | 22349 | 3391 | 3207 | 486 |
| -, -, -, -, DQA1*03:02, -, DQB1*03:03, -, -, -, -, - | 6583 | 91 | 424 | 21 | 84 | 17 | 22488 | 3351 | 2651 | 441 |
| -, -, -, -, DQA1*02:01, -, DQB1*03:03, -, -, -, -, - | 6720 | 109 | 10667 | 469 | 94 | 23 | 22211 | 2934 | 2710 | 464 |
| -, -, -, -, DQA1*03:01, -, DQB1*03:03, -, -, -, -, - | 2768 | 82 | 197 | 26 | 117 | 23 | 22331 | 2422 | 1364 | 243 |
| Sum | 75489 | 1800 | 51244 | 2505 | 3891 | 767 | 586994 | 58920 | 211481 | 20264 |
| Reactivity (%) | 100% | 2% | 100% | 5% | 100% | 20% | 100% | 10% | 100% | 10% |

TABLE F

MFI (raw) against individual HLA-DR antigens measured using SAB assay.

| | P02 | | P04 | | P07 | | P08 | | P09 | |
|---|---|---|---|---|---|---|---|---|---|---|
| Allele specificity | +PBS | +IdeS | +PBS | +Ides | +PBS | +IdeS | +PBS | +IdeS | +PBS | +Ides |
| DRB1*01:02, -, -, -, -, -, -, -, -, -, -, - | 17110 | 487 | 675 | 42 | 115 | 20 | 431 | 25 | 255 | 32 |
| DRB1*01:01, -, -, -, -, -, -, -, -, -, -, - | 18574 | 696 | 402 | 31 | 106 | 17 | 340 | 23 | 107 | 24 |
| DRB1*10:01, -, -, -, -, -, -, -, -, -, -, - | 21681 | 1351 | 327 | 28 | 691 | 26 | 23510 | 849 | 188 | 54 |
| DRB1*01:03, -, -, -, -, -, -, -, -, -, -, - | 16759 | 508 | 2850 | 51 | 82 | 18 | 487 | 21 | 116 | 22 |
| DRB1*11:04, -, -, -, -, -, -, -, -, -, -, - | 216 | 37 | 1575 | 66 | 5395 | 140 | 22704 | 1252 | 3740 | 513 |
| DRB1*11:01, -, -, -, -, -, -, -, -, -, -, - | 159 | 20 | 705 | 33 | 4552 | 95 | 21697 | 956 | 3207 | 380 |
| DRB1*12:02, -, -, -, -, -, -, -, -, -, -, - | 8815 | 293 | 7903 | 139 | 3381 | 63 | 23939 | 1668 | 2763 | 366 |
| DRB1*12:01, -, -, -, -, -, -, -, -, -, -, - | 9541 | 322 | 13327 | 341 | 3622 | 67 | 23623 | 1761 | 2803 | 344 |
| DRB1*13:03, -, -, -, -, -, -, -, -, -, -, - | 207 | 16 | 4923 | 104 | 6523 | 156 | 23331 | 1541 | 4764 | 550 |
| DRB1*13:01, -, -, -, -, -, -, -, -, -, -, - | 409 | 22 | 269 | 22 | 5257 | 119 | 22827 | 1247 | 4399 | 430 |
| DRB1*14:54, -, -, -, -, -, -, -, -, -, -, - | 5152 | 115 | 319 | 55 | 4412 | 114 | 22371 | 1320 | 3796 | 471 |
| DRB1*14:01, -, -, -, -, -, -, -, -, -, -, - | 6374 | 115 | 203 | 23 | 5847 | 135 | 23061 | 1611 | 4316 | 577 |
| DRB1*14:02, -, -, -, -, -, -, -, -, -, -, - | 2374 | 70 | 253 | 45 | 3609 | 96 | 21144 | 978 | 3310 | 336 |
| DRB1*15:02, -, -, -, -, -, -, -, -, -, -, - | 289 | 16 | 2435 | 68 | 94 | 16 | 22630 | 715 | 600 | 79 |
| DRB1*15:01, -, -, -, -, -, -, -, -, -, -, - | 363 | 18 | 3604 | 87 | 87 | 15 | 22151 | 929 | 845 | 102 |
| DRB1*15:03, -, -, -, -, -, -, -, -, -, -, - | 988 | 37 | 1943 | 72 | 150 | 35 | 22653 | 766 | 620 | 90 |
| DRB1*16:01, -, -, -, -, -, -, -, -, -, -, - | 322 | 29 | 1946 | 70 | 151 | 30 | 22645 | 782 | 868 | 130 |
| DRB1*16:02, -, -, -, -, -, -, -, -, -, -, - | 374 | 31 | 2495 | 80 | 142 | 28 | 22465 | 686 | 829 | 112 |
| DRB1*03:01, -, -, -, -, -, -, -, -, -, -, - | 264 | 20 | 182 | 22 | 6129 | 134 | 23891 | 2299 | 7907 | 778 |
| DRB1*03:02, -, -, -, -, -, -, -, -, -, -, - | 592 | 40 | 268 | 38 | 4394 | 104 | 22857 | 1681 | 5032 | 524 |
| DRB1*04:02, -, -, -, -, -, -, -, -, -, -, - | 13287 | 377 | 970 | 45 | 920 | 33 | 21202 | 1269 | 2770 | 330 |
| DRB1*04:03, -, -, -, -, -, -, -, -, -, -, - | 11768 | 304 | 927 | 79 | 762 | 41 | 22904 | 1174 | 2415 | 321 |
| DRB1*04:05, -, -, -, -, -, -, -, -, -, -, - | 13364 | 356 | 306 | 36 | 786 | 36 | 21299 | 1151 | 2439 | 318 |
| DRB1*04:04, -, -, -, -, -, -, -, -, -, -, - | 14417 | 431 | 1125 | 67 | 933 | 35 | 21760 | 1426 | 2682 | 369 |
| DRB1*04:01, -, -, -, -, -, -, -, -, -, -, - | 13713 | 413 | 807 | 60 | 897 | 36 | 21712 | 1323 | 2723 | 381 |
| -, -, DRB5*01:01, -, -, -, -, -, -, -, -, -, -, - | 13374 | 364 | 679 | 48 | 194 | 27 | 12086 | 140 | 147 | 37 |
| -, -, DRB5*02:02, -, -, -, -, -, -, -, -, -, -, - | 15426 | 490 | 1677 | 47 | 99 | 16 | 8798 | 241 | 692 | 37 |
| -, -, DRB3*03:01, -, -, -, -, -, -, -, -, -, -, - | 8925 | 415 | 927 | 95 | 667 | 103 | 22575 | 1013 | 1211 | 249 |
| -, -, DRB3*01:01, -, -, -, -, -, -, -, -, -, -, - | 8394 | 284 | 270 | 36 | 572 | 40 | 20467 | 1862 | 4190 | 479 |
| -, -, DRB3*02:02, -, -, -, -, -, -, -, -, -, -, - | 295 | 25 | 441 | 41 | 1203 | 45 | 22652 | 1251 | 1561 | 226 |
| -, -, DRB4*01:03, -, -, -, -, -, -, -, -, -, -, - | 21616 | 1327 | 247 | 32 | 104 | 32 | 23348 | 2341 | 439 | 213 |
| -, -, DRB4*01:01, -, -, -, -, -, -, -, -, -, -, - | 19130 | 944 | 686 | 64 | 304 | 22 | 23279 | 1917 | 870 | 196 |
| DRB1*07:01, -, -, -, -, -, -, -, -, -, - | 16524 | 691 | 25134 | 1957 | 107 | 16 | 24193 | 1793 | 2057 | 301 |
| DRB1*08:01, -, -, -, -, -, -, -, -, -, - | 171 | 29 | 2716 | 59 | 4588 | 100 | 22391 | 1101 | 4075 | 543 |
| DRB1*09:01, -, -, -, -, -, -, -, -, -, - | 17862 | 712 | 15740 | 648 | 199 | 42 | 22643 | 1466 | 1650 | 257 |
| DRB1*09:02, -, -, -, -, -, -, -, -, -, - | 20587 | 820 | 19870 | 1099 | 133 | 28 | 23199 | 1416 | 3767 | 351 |
| Sum | 319416 | 12223 | 119123 | 5831 | 67208 | 2080 | 723269 | 41992 | 84154 | 10522 |
| Reactivity (%) | 100% | 4% | 100% | 5% | 100% | 3% | 100% | 6% | 100% | 13% |

REFERENCES

Ding J W, Zhou T, Zeng H, Ma L, Verbeek J S, Yin D, m.fl. Hyperacute rejection by anti-Gal IgG1, IgG2a, and IgG2b is dependent on complement and Fc-gamma receptors. J Immunol. 1 Jan. 2008; 180 (1):261-8.

Jordan S C, Vo A, Bunnapradist S, Toyoda M, Peng A, Puliyanda D, Kamil E, Tyan D. Intravenous immune globulin treatment inhibits crossmatch positivity and allows for successful transplantation of incompatible organs in living-donor and cadaver recipients. Transplantation 2003 August; 76 (4):631-636.

Moll S and Pascual M. Humoral rejection of organ allografts. Am. J. Transplant 2005 November; 5(11):2611-2618.

Montgomery R A, Hardy M A, Jordan S C, Racusen L C, Ratner L E, Tyan D B, Zachary A A. Consensus opinion from the antibody working group on the diagnosis, reporting, and risk assessment for antibody-mediated rejection and desensitization protocols. Transplantation 2004 July; 78(2):181-185.

Organ Procurement and Transplantation Network (OPTN) Database. US Department of Health and Human Services, Health Resources and Services Administration; May 11, 2011.

Thomas B. Martins. Development of Internal Controls for the Luminex Instrument as Part of a Multiplex Seven-Analyte Viral Respiratory Antibody Profile Patel R, Terasaki P I. Significance of the positive crossmatch test in kidney transplantation. N. Engl. J. Med. 1969 April; 280(14):735-739.

Pierson R N 3rd. Antibody-mediated xenograft injury: mechanisms and protective strategies. Transpl Immunol. June 2009; 21(2):65-9.

Terasaki P I, Ozawa M. Predicting kidney graft failure by HLA antibodies: a prospective trial. Am. J. Transplant 2004 March; 4(3):438-443.

Vo A A, Petrozzino J, Yeung K, Sinha A, Kahwaji J, Peng A, m.fl. Efficacy, outcomes, and cost-effectiveness of desensitization using IVIG and rituximab. Transplantation. 27 Mar. 2013; 95(6):852-8.

von Pawel-Rammingen U, Johansson B P, Björck L. IdeS, a novel streptococcal cysteine proteinase with unique specificity for immunoglobulin G. EMBO J 2002 April; 21(7): 1607-1615.

Åkesson P, Moritz L, Truedsson M, Christensson B, von Pawel-Rammingen U. IdeS, a highly specific immunoglobulin G (IgG)-cleaving enzyme from Streptococcus pyogenes, is inhibited by specific IgG antibodies generated during infection. Infect. Immun 2006 January; 74(1): 497-503.

EXAMPLE 3

Introduction

As is demonstrated in Examples 1 and 2, IdeS rapidly cleaves all plasma IgG after intravenous administration to human subjects. The following in vitro and ex vivo data show that IdeS not only cleaves soluble IgG as previously shown, but also cuts off the F(ab')$_2$ part of the B-cell receptor complex from surface IgG-positive B-cells. The truncation of the BCR through IdeS has strong inhibiting effects on the induction of secreted IgG from R848 and IL-2 activated CD27 positive memory B-cells, while the IgM secretion of surface IgM-positive BCR cells are not reduced by the treatment with IdeS. This suggests that the treatment with IdeS of patients with donor specific antibodies not only removes said antibodies, but also renders donor-specific memory B cells (at least initially) incapable of responding to donor antigens. Thus, any initial activation of the memory B cells and generation of plasma cells which could produce more donor specific antibodies is also affected.

Material and Methods

Screening Cell Lines for Surface Immunoglobulin

Different human B-cell lymphoma cell lines i.e. U-2940 (ACC634), NU-DUL-1 (ACC579), Raji (CCL-86) and Daudi (CCL-213) were screened for the presence of membrane bound IgG or IgM. Briefly, cells were cultured at 37° C. in 5% $CO_2$ in RPMI1640 supplemented with 10% FCS and PEST. Cells were treated for 30 min at 37° C. with PBS or different concentrations of IdeS prior to acid wash (0.1 M glycine pH 2.7, 0.5 M NaCl) for 5 min on ice. Acid wash removes antibodies present in FcγR's or bound to antigen while leaving transmembrane molecules intact (Gilden et al., 1978, Jennings et al., 2011). Cells were stained with biotinylated antibodies specific for the F(ab')$_2$ part (#109-066-097, Jackson, cross-reacts with light chain present in all immunoglobulin subclasses) and the Fc-part of IgG (#109-066-098, Jackson, specific for IgG heavy chain) or IgM (GM-80A, ICL). Streptavidin-APC (#016-130-084, Jackson) was used to monitor cells in FL4 using an Accuri C6 flow cytometer.

Cell Proliferation and Viability Assays

Proliferation was measured by BrdU incorporation. Cells were treated with PBS or different concentrations of IdeS and 5×10$^4$ cells/well were seeded in 96-well plates and cultured for 24 hours. BrdU was added to cells and incubated for 6 hours prior to measuring proliferation according to the manufacturers recommendation (Cell Proliferation ELISA, BrdU colorimetric, Roche #11 647 229 001). Cytochalasin D (C2618, Sigma) and Puromycin (Invitrogen) were used at different concentrations as anti-proliferative controls.

A sensitive colorimetric assay (CCK-8) was used to measure cell viability. Cells were treated with PBS or 30 µg/ml IdeS and 2×10$^4$ cells/well were seeded in 96-well plates and cultured for 24 hours. CCK-8 (CCK-8 cell counting kit 8, Dojindo Laboratories, Japan) was added and the absorbance at 450 nm was followed at different time points. In experiments with Nu-DUL-1 cells they were treated with PBS or 30 µg/ml IdeS and different amount of cells were seeded in 96-well plates and cultured for 24 hours prior to addition of CCK-8. In experiments with enriched B-cells peripheral blood was collected in heparin tubes supplemented with IdeS at 30 µg/ml or PBS and incubated at 37° C., 5% $CO_2$ for 30 minutes. 250 µl RosetteSep® Human B cell Enrichment cocktail (#07905, StemCell Technologies) was added to 5 ml blood, mixed well and incubate for 20 minutes at room temperature. Samples were diluted with an equal volume of PBS supplemented with 2% FCS prior to density gradient separation (Ficoll-PaquePLUS). Harvested B-cells were counted and adjusted to 20×10$^4$ cells/ml in RPMI1640 supplemented with 10% FCS and PEST. 2×10$^4$ cells/well were seeded in triplicates in 96-well plates and cultured for 24 hours prior to addition of CCK-8.

Addressing IdeS Efficacy in Plasma by SDS-PAGE

Plasma collected during density gradient separation of heparin blood treated with PBS or different amounts of IdeS was used to verify IdeS efficacy on soluble IgG. The SDS-PAGE analyses were performed according to the manufacturer's instructions (Bio-Rad Laboratories, CA, USA). Briefly, 1 µl of plasma was separated on 4-20% Mini-PROTEAN®TGX™ precast gels (Bio-Rad) at 200 V for 40 minutes under non-reduced conditions. The gels were stained with GelCode Blue stain reagent (Pierce, Thermo Fisher Scientific, MA, USA) according to the manufacturer's instructions and the gels were scanned.

Recovery of Cleaved BCR

Nu-DUL-1 cells were treated with PBS or different amounts of IdeS for one hour at 37° C. prior to extensive washing in order to remove any remaining IdeS. The cells were seeded in 96-well plates in RPMI1640 supplemented with 10% FCS and PEST. One plate was immediately used for flow cytometry analysis of intact IgG and the other was cultured (37° C., 5% $CO_2$) for 24 hours prior to analysis. Cells were stained with a biotinylated antibody specific for the F(ab')$_2$ part (#109-066-097, Jackson) followed by Streptavidin-APC (#016-130-084, Jackson) and cells were monitored in FL4 using an Accuri C6 flow cytometer.

Peripheral blood was collected in heparin tubes (BD Vacutainer, #367876) from healthy volunteers and treated with either 30 µg/ml IdeS or PBS for one hour at 37° C. prior to isolating PBMC using density gradient separation (Ficoll-PaquePLUS). The PBMC interface was collected, washed in PBS and re-suspended in culture medium (RPMI1640 supplemented with 10% FCS and PEST). PBMCs were counted, adjusted to 2×10$^6$ cells/ml and a sample was removed, fixed in PFA, washed in PBS supplemented with 0.1% BSA and stored at 4° C. until flow cytometry analysis. The remaining cells were cultured and samples were removed and PFA fixed at indicated time points. For detection of the F(ab')$_2$ part of IgG, biotinylated anti-CH1-IgG (#710.3202.100, BAC) was used, for detection of the Fc-part of IgG goat anti-human Fc-specific F(ab')$_2$ fragment (#109-066-098, Jackson) was used. Cells were further double stained with PE-conjugated anti-CD19 (#IP-305-T100, ExBio) and Streptavidin-APC (#016-130-084, Jackson). The lymphocyte population was gated using forward-side scatter and double positive cells were monitored in FL2 and FL4 using an Accuri C6 flow cytometer.

Intracellular Phospho-Specific Flow Cytometry (BCR Signalling)

Nu-DUL-1 cells were cultured overnight in serum free medium in order to minimize background phosphorylation prior to start of signalling experiments. The next day PBS or 30 µg/ml IdeS was added and the cells were cultured (37° C., 5% $CO_2$) for 30 min. 1×10$^6$ cells were removed and fixed for 5 min in PFA followed by 10 min permeabilization in 70% ethanol on ice. Cells were washed in PBS supplemented with 0.1% BSA and stored at 4° C. until analysis (zero sample). After collection of the zero sample, the BCR of the remaining cells was cross-linked by addition of 10 µg/ml goat anti-human F(ab')$_2$ specific F(ab')$_2$ (Jackson #109-006-097) and cell-samples were collected at different time points, fixed and permeabilized. The fixed cells were stained for flow cytometry analysis using APC-conjugated phospho-specific ERK1/2 (#17-9109-42, eBioscience) and PE-conjugated phospho-specific PLC-γ2 (#558490, BD). Cells were monitored in FL2 and FL4 using an Accuri cytometer C6.

Memory B-Cell Differentiation

Peripheral blood was collected in heparin tubes (BD Vacutainer, #367876) from healthy volunteers and PBMC were isolated using density gradient separation (Ficoll-PaquePLUS). The PBMC interface was collected, washed in PBS and re-suspended in culture medium (RPMI1640 supplemented with 10% FCS and PEST). PBMCs were adjusted to $2 \times 10^6$ cells/ml and seeded either with IdeS (final concentration 0.3, 3 and 30 µg/ml) or PBS. Cells were stimulated with a mixture of R848 and rIL-2 according to the manufacturer's recommendation (MabTech) and cultured for 72-96 hours. Cells intended for the short time treatments were left in tubes supplemented with PBS or IdeS and incubated for one hour at 37° C. prior to washing 3×12 ml with PBS and 1×12 ml in culture medium. These cells were seeded and treated with R848/rIL-2 as above.

ELISpot filter plates were pre-wetted with 70% ethanol, washed with sterile water and incubated at 4° C. overnight with capture antibody (ELISpotPLUS Mabtech kit #3850-2HW-Plus for monitoring IgG producing cells, ELISpotPLUS Mabtech kit #3845-2HW-Plus for monitoring IgM producing cells and ELISpotBASIC Mabtech kit #3860-2H for monitoring IgA producing cells). The ELISpot filter plates were wash and blocked for at least 30 min with culture medium prior to seeding cells.

The cells were transferred to 15 ml tubes, extensively washed, counted and adjusted to $0.5 \times 10^6$ cells/ml and 2-fold dilutions were prepared before cells were seed in the prepared ELISpot filter plates and cultured for 24 hours. ELISpot-plates were washed and biotinylated detection antibodies for total IgG, IgM and IgA analysis (included in the named kits) were incubated for two hours at room temperature. Plates were wash and incubated for one hour at room temperature with Streptavidin-HRP before they were washed and incubated with TMB ready-to-use solution and developed until distinct spots emerged. The plates were washed in tap water and allowed to dry in the dark. The filters were photo documented and spots were manually counted.

B-Cell Enrichment and Flow Cytometry

For B-cell enrichment peripheral blood was collected in heparin tubes supplemented with IdeS at 30 µg/ml or PBS and incubated at 37° C., 5% $CO_2$ for 30 minutes. 250 µl RosetteSep® Human B cell Enrichment cocktail (#07905, StemCell Technologies) was added to 5 ml blood, mixed well and incubate for 20 minutes at room temperature. Samples were diluted with an equal volume of PBS supplemented with 2% FCS prior to density gradient separation (Ficoll-PaquePLUS). Harvested B-cells were counted and adjusted to $15 \times 10^4$ cells/ml in PBS supplemented 2% FCS prior to seeding in V-shaped 96-well plates for flow cytometry staining. Plates were cfg at 1500 rpm for 3 minutes and the supernatant was flicked off. For detection of the $F(ab')_2$ part of IgG, 10 µg/ml biotinylated anti-CH1-IgG (#710.3202.100, BAC) was used, for detection of the Fc-part of IgG 0.5 µg/ml goat anti-human Fc-specific $F(ab')_2$ fragment (#109-066-098, Jackson) was used. Cells were further double stained with either PE-conjugated anti-CD19 (#IP-305-T100, ExBio) or PE-conjugated anti-CD27 (#555441, Pharmingen) followed by Streptavidin-APC ((#016-130-084, Jackson). Cells were monitored in FL2 and FL4 using an Accuri cytometer C6.

IdeS Cleaves the IgG-Type of BCR in a First in Man Clinical Study

A phase I, double blind and randomized study with single ascending doses of IdeS was conducted at the Phase 1 Unit, Lund, after approval from Swedish regulatory and ethical authorities (ClinicalTrials.gov Identifier: NCT01802697). All subjects signed written informed consent before any study related procedures were initiated. As an exploratory part of the study, the integrity of the IgG-type of BCR on CD19$^-$ cells was monitored at different time-points after intravenous treatment with 0.12 or 0.24 mg/kg BW IdeS. Peripheral blood was collected in heparin tubes and PBMCs were isolated within 2 hours from collection using density gradient separation (Ficoll-PaquePLUS). The PBMC interface was collected, washed in PBS and fixed in PFA for 30 min on ice. Cells were washed and stored in PBS supplemented with 0.5% BSA until all time points were collected. Cells were stained with 10 µg/ml biotinylated anti-CH1-IgG (#710.3202.100, BAC) for detection of the $F(ab')_2$ part of IgG. For detection of the Fc-part of IgG 0.5 µg/ml goat anti-human Fc-specific $F(ab')_2$ fragment (#109-066-098, Jackson) was used. Cells were further double stained with PE-conjugated anti-CD19 (#21270194, Immunotools) and Streptavidin-APC (#016-130-084, Jackson). The lymphocyte population was gated in the pre-dose sample for each individual and this gate was then used for all time points for a subject. CD19$^+$ cells were monitored in FL2 and the $F(ab')_2$/Fc-signal was monitored in FL4. CD19$^+$ cells were monitored in M1 (FL2) and these cells were further monitored for presence of a signal upon anti-Fc and anti-Fab staining (FL4). In each sample the cell counts in upper right (UR) as well as mean fluorescent intensity (MFI) were collected.

Furthermore, the frequency of double positive cells was calculated using the following formula:

$$\text{MFI in } UR \times \text{cell counts in } UR/\text{cell counts in } M1$$

This formula was used to be able to appreciate the difference in MFI when only low cell counts were present in UR.

Results

IdeS Cleaves the IgG-Type of BCR with Similar Efficacy as Soluble IgG

Figure 20A:
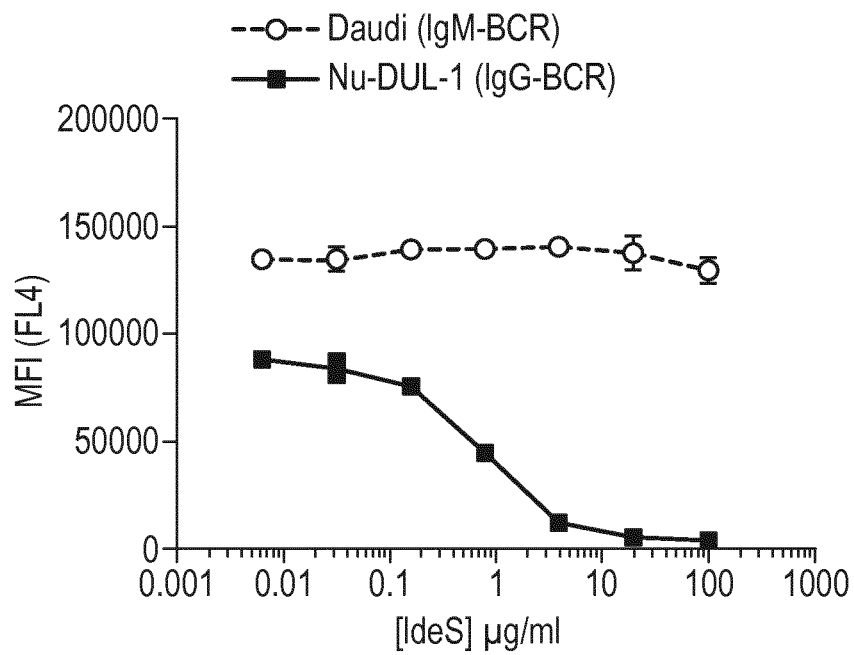
FIGS. 20A and 20B show that IdeS cleaves IgG-type but not IgM-type of BCR on B-cells.
Figure 20B:
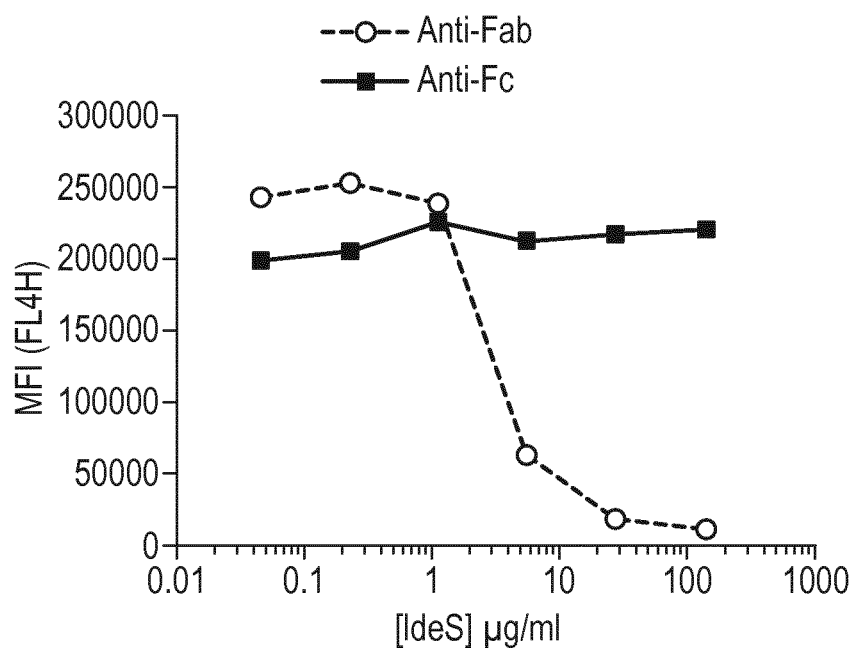

Four different B-lymphoma cell lines were screened for the presence of transmembrane IgG or IgM using a flow cytometry approach including an acid wash step to remove IgG or IgM not attached to the membrane via a transmembrane domain (Gilden et al., 1978, Jennings et al., 2011). After verifying the presence of IgG- or IgM-type of BCR on the cell lines, Nu-DUL-1 (IgG-type of BCR) and Daudi (IgM-type of BCR) were selected as models for further analysis. A Fab-fragment specific $F(ab')_2$ antibody was used to detect the presence of the Fab-part of BCR since the antibody cross-reacts with the light-chain present in both IgG and IgM. To detect the presence of the Fc-part, antibodies directed at the Fc-part of IgG was used. Intact membrane-bound IgG could not be detected on the cell surface at an IdeS concentrations above 4 µg/ml. Daudi cells having an IgM-type of BCR were not affected even at high concentrations of IdeS (FIG. 20A). Nu-DUL-1 cells were treated with different concentrations of IdeS and incubated at 37° C. for 30 min prior to FACS staining. IdeS was shown to efficiently remove the $F(ab')_2$ part of IgG present in the BCR leaving the cleaved Fc-part attached to the membrane (FIG. 20B).

Figure 21A:
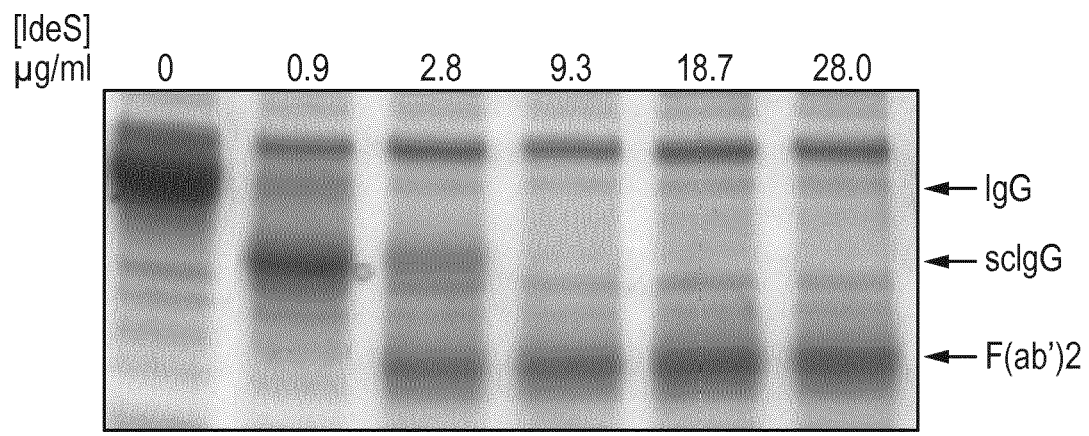
FIGS. 21A and 21B show that IdeS cleaves the IgG-type of BCR with similar efficacy as soluble IgG.

We next moved to addressing BCR cleavage on PBMCs purified from healthy volunteers. Due to the cross-reactivity of the Fab-specific antibody with light-chains on IgM, the anti-IgG-CH1-domain specific CaptureSelect fragment was used for staining the heterogenic PBMC population. Blood collected in heparin-tubes was treated for 30 minutes (37° C.) with different concentrations of IdeS. The PBMCs were density-gradient separated after IdeS treatment and both plasma and PBMCs were collected. The plasma was analysed on SDS-PAGE to confirm IdeS efficacy on soluble IgG (FIG. 21A). ScIgG was generated already at 0.9 µg/ml IdeS and full cleavage was achieved at 9 µg/ml.

Figure 21B:
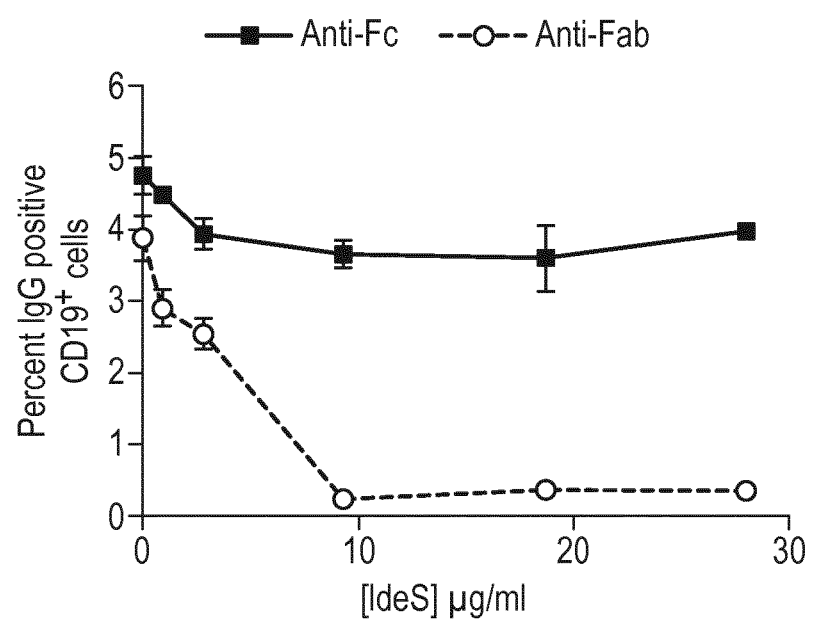

Since CD19 is a hallmark for B-cell linages the PBMCs were double stained with anti-CD19 and anti-Fab or anti-Fc in order to monitor the presence of intact IgG-BCR on B-cells. Flow cytometry showed that IdeS could remove the F(ab')$_2$ part of IgG from CD19$^-$ cells while leaving the Fc-part in the membrane (FIG. 21B). As single-cleaved membrane bound IgG present in the BCR is still attached to the membrane, the effect is not fully visible by flow cytometry as long as the scIgG product is present and attached to the membrane. Full effect was reached on membrane bound IgG at 9 µg/ml IdeS. Thus these results show for the first time that there is a direct correlation between IdeS efficacy on free IgG and membrane bound IgG correspondingly present in B-cell receptors.

Figure 22A:
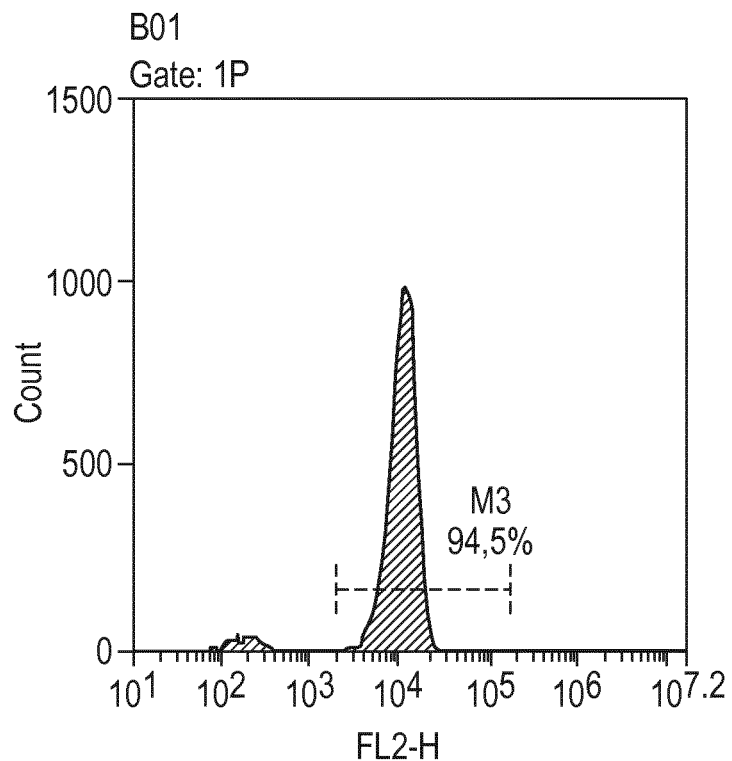
FIGS. 22A and 22B show that IdeS cleaves surface IgG on memory B-cells.
Figure 22B:
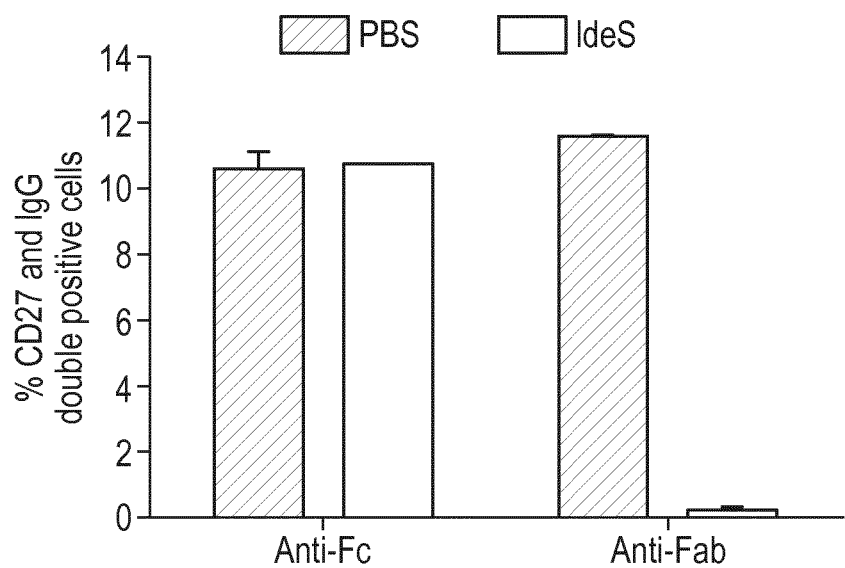

In order to further define the effect of IdeS on the memory subset of B-cells the effect on CD19$^+$/CD27$^+$ memory B-cells was investigated. CD19$^+$ B-cells only constitute a few percent of the total PBMC population. Hence, CD19$^+$ B-cells were enriched using negative selection (RosetteSep), which generated >90% CD19$^+$ cells (FIG. 22A). Approximately 10% of this population stained double positive for surface IgG and CD27 prior to IdeS treatment (FIG. 22B). After IdeS treatment less than 1% of the CD19$^+$/CD27$^+$ cells stained positive for cell surface IgG (FIG. 22B). Thus, these data show for the first time that the BCR on class-switched memory B cells i.e. CD19$^+$/CD27$^+$/surface IgG$^+$ cells is efficiently cleaved by IdeS.

Figure 23A:
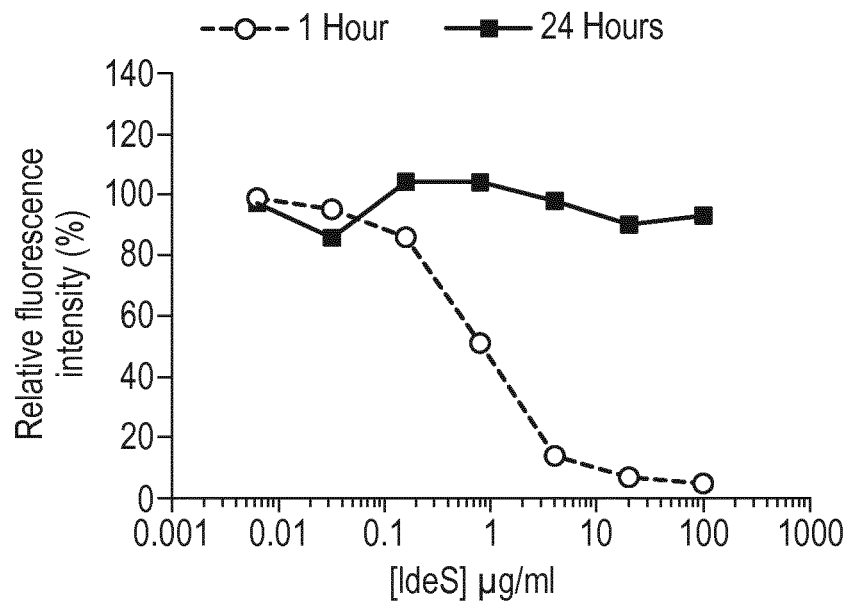
Figure 23B:
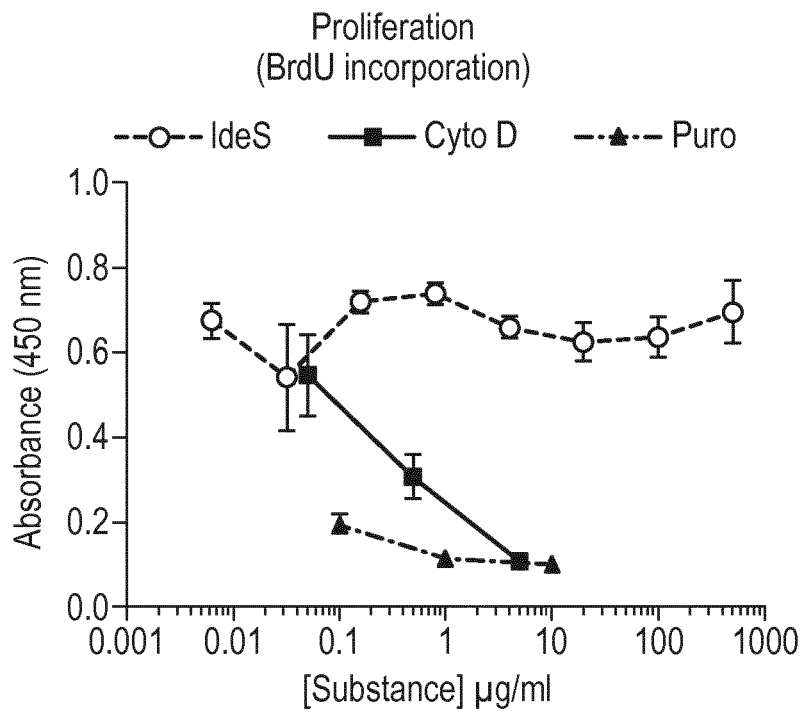

Cleaved BCR is Rapidly Regenerated on Both Cell Lines and PBMCs and has No Effect on Cell Viability In order to investigate the membrane turnover of the IgG-type of BCR the Nu-DUL-1 cells were treated with different concentrations of IdeS, washed to remove IdeS and cultured. Fractions of cells were removed one and 24 hours after treatment and analysed for membrane bound IgG by flow cytometry. One hour after treatment there was no detectable IgG at IdeS concentrations >4 µg/ml but 24 hours after treatment, the Fab specific signal was back at the original levels demonstrating that the membrane bound IgG had recovered (FIG. 23A). Nu-DUL-1 cells were also analysed for proliferative capacity using BrdU incorporation and there was no difference in proliferation after cleaving the IgG-type of BCR even when IdeS treatment was continued over 24 hours (FIG. 23B). Substances with known antiproliferative capacity (puromycin and cytochalasin D) had a strong anti-proliferative effect on the cells. The viability of Nu-DUL-1 cells was also investigated by treating cells with a high dose of IdeS (30 µg/ml) for 24 hours and viability was analysed using the CCK-8 assay and there was no effect on cell viability after IdeS treatment (FIG. 23C).

Figure 24A:
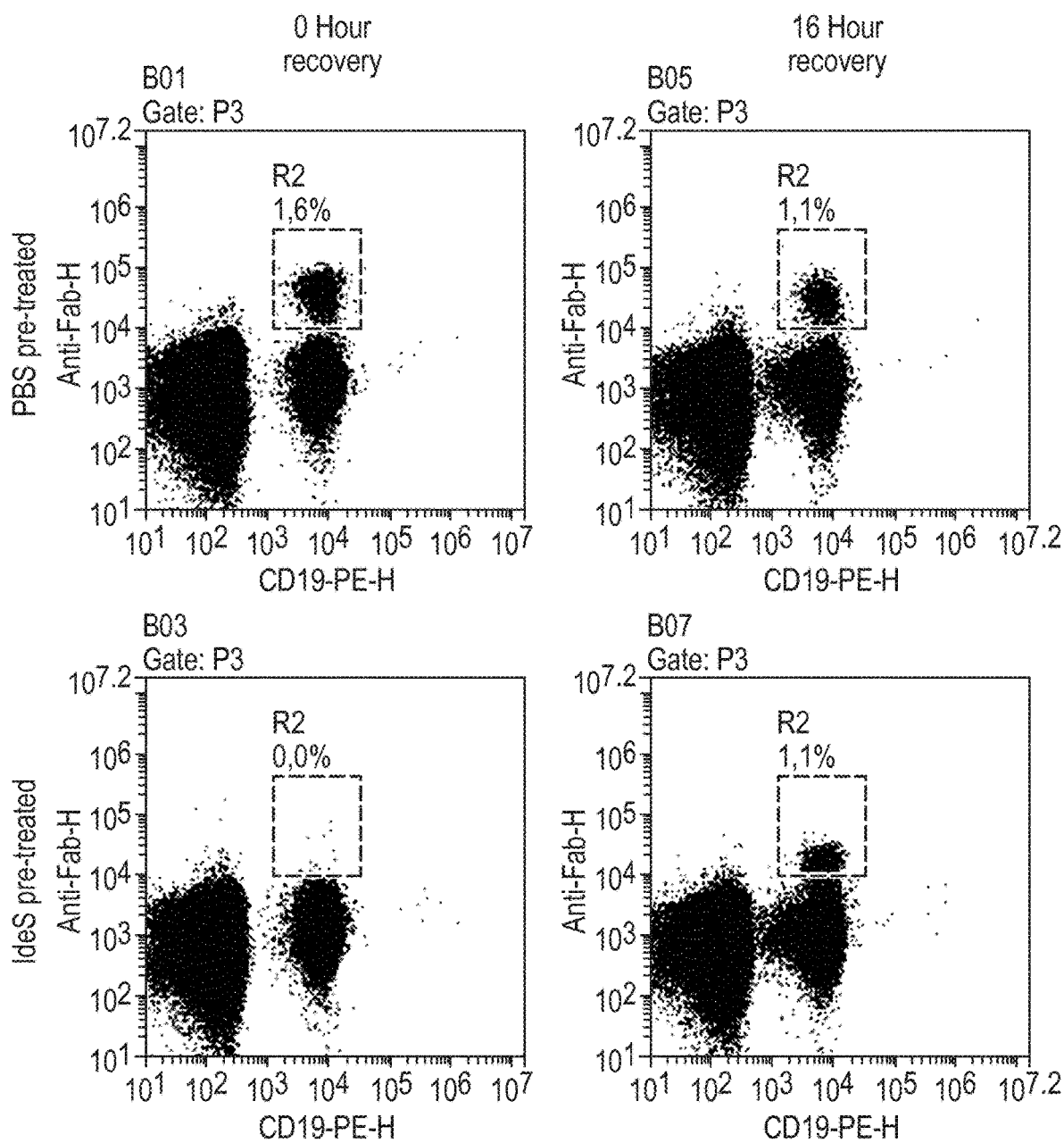
FIGS. 24A and 24B show the recovery of IgG-type BCR expression on ex vivo IdeS treated PBMC's.
Figure 24B:
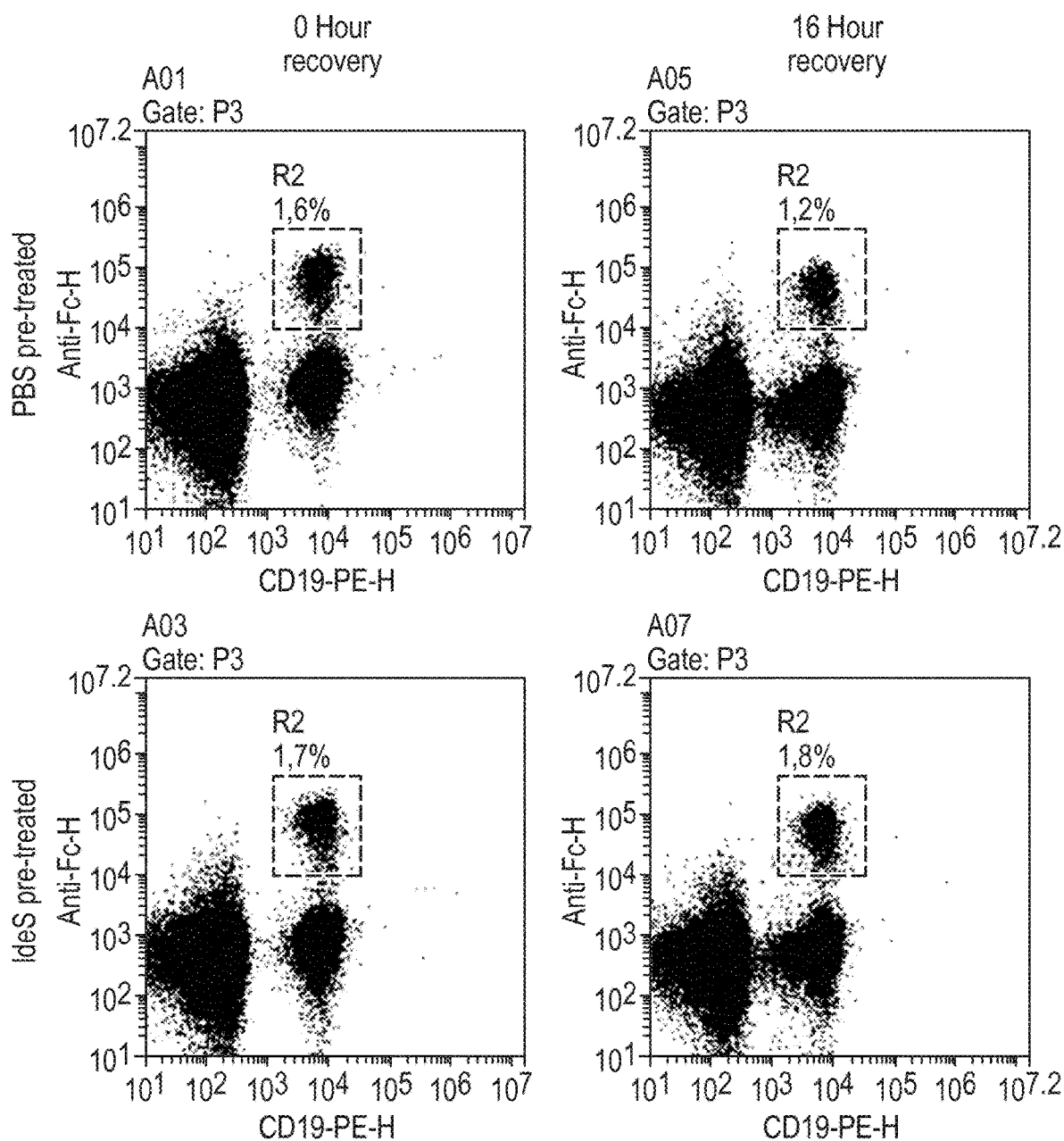
Figure 25A:
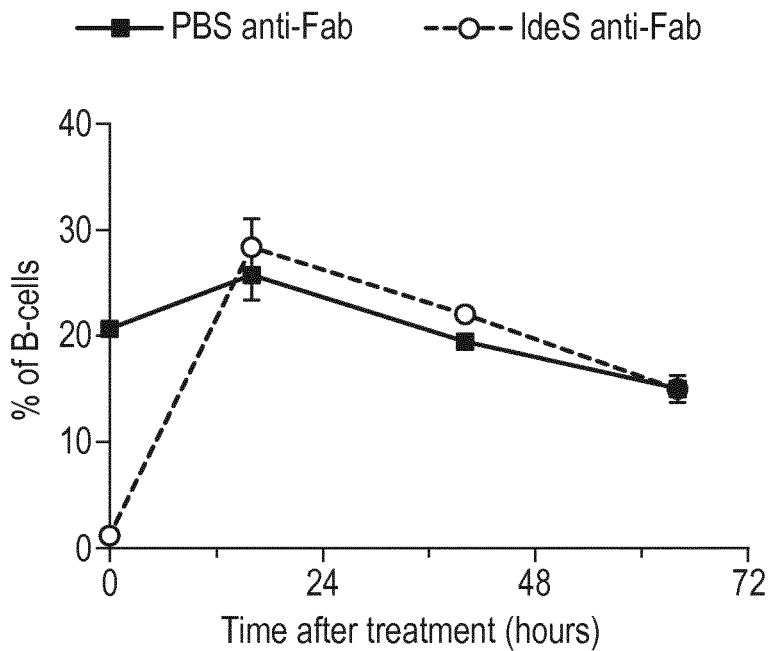
FIGS. 25A and 25B show recovery of IgG-type of BCR on enriched B-cells (RosetteSep, >90% CD19$^+$ cells).
Figure 25B:
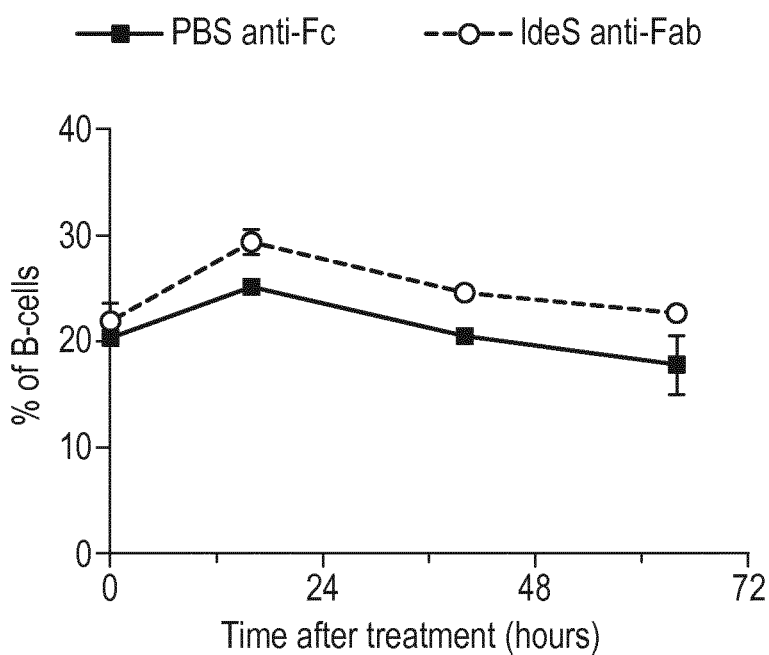

The findings that the IgG-type of BCR was regenerated within 24 hours on a highly proliferating lymphoma cell line could be expected since membrane turn-over on proliferating cells is usually very high. PBMCs from healthy volunteers were subjected to a similar treatment in order to further investigate the turn-over of the IgG-type of BCR on primary cells. Blood was collected in heparin-tubes and treated with a high dose (30 µg/ml) of IdeS. After treatment of the blood the PBMCs were separated on Ficoll. The PBMCs were washed with large volumes of buffer in order to remove all IdeS prior to culturing. A fraction of cells were removed at different time points, fixed and stained with anti-CD19 for B-cell linage and further stained with anti-Fab or anti-Fc to monitor IgG-BCR. The IgG-type of BCR was rapidly regenerated also on normal human CD19$^-$ cells and already within 16 hours after cleavage the number of anti-Fab positive cells was back to pre-treatment levels though still not reaching the full MFI. This indicates that 16 hours post IdeS treatment of PBMCs the cells again have intact IgG-BCR on the surface even though all IgG-BCR are not yet replaced (FIG. 24A). The anti-Fc signal was not affected by the treatment demonstrating that IdeS treatment shed the F(ab')$_2$ from the IgG-type of BCR (FIG. 24B). Because B-cells only account for a few percent of the total PBMC population we also used a B-cell enrichment kit (RosetteSep), which generated >90% CD19$^+$ cells. Approximately 20% of the CD19 enriched cell population stained positive for IgG using both the F(ab')$_2$ and the Fc specific reagents (FIG. 25). The cell surface recovery experiment was repeated using these purified cells and IdeS treatment efficiently removed the F(ab')$_2$ part of the membrane bound IgG leaving the Fc-part intact (FIGS. 25A and 25B). Again, the turn-over was rapid and already 16 hours after treatment the cell surface IgG had recovered (FIG. 25A). Cell viability was followed for several days using the CCK-8 assay in order to evaluate survival of primary human B-cells with or without an intact BCR. There was no significant effect on cell viability when temporally removing the IgG-type of BCR from the CD19 enriched cells by IdeS treatment (FIG. 26).

IdeS Treatment Inhibits BCR Signalling

Figure 27A:
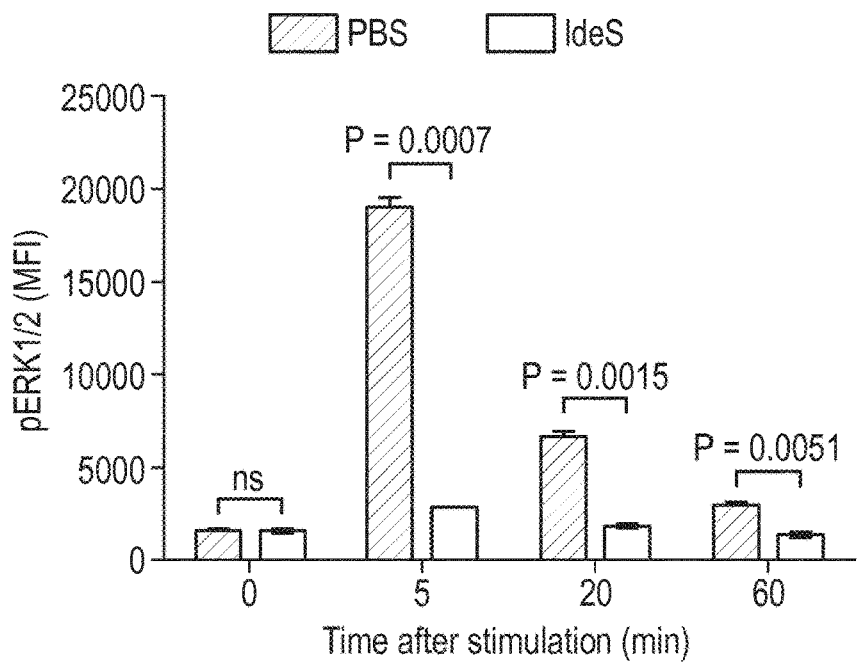
FIGS. 27A and 27B show IdeS treatment inhibits BCR signalling. Nu-DUL-1 cells were treated with PBS or IdeS (30 µg/ml) prior to cross-linking using a F(ab')$_2$ specific antibody.
Figure 27B:
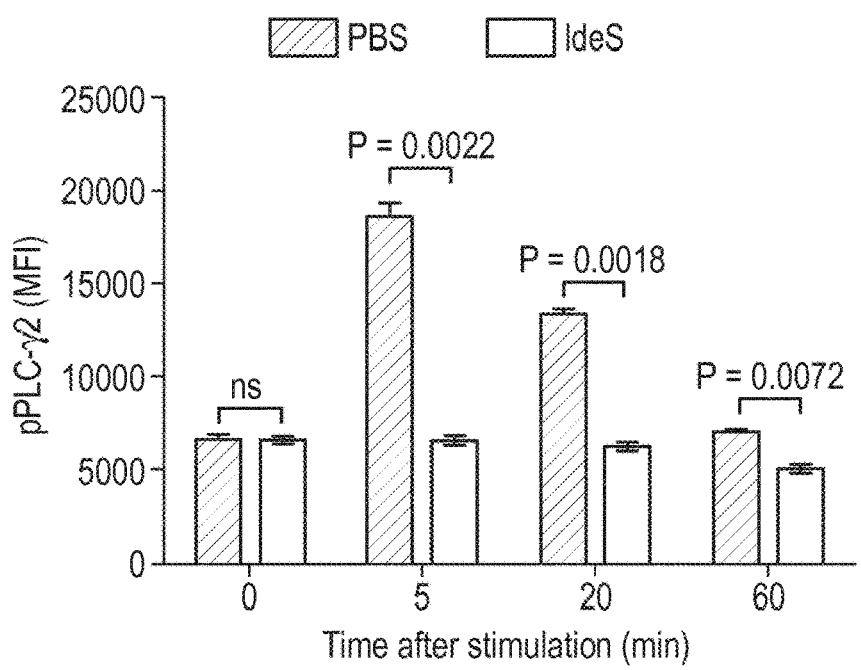

BCR signalling is important in the activation, survival, and differentiation of B lymphocytes. The initial event after BCR engagement is the activation of Lyn and Syk, which is then further propagated into activation of PLC-γ2 and ERK1/2. The described experiments clearly showed that IdeS could cleave the IgG-type of BCR, which should have implications on the BCR signalling. To verify this PLC-γ2 and ERK 1/2 phosphorylation were monitored as downstream indicators for the BCR signalling cascade. In a series of experiments where the BCR on Nu-DUL-1 cells was cross-linked using a F(ab')$_2$ specific antibody it was shown that the cells were unable to signal through the BCR after IdeS treatment (FIGS. 27A and 27B). Neither PLC-γ2 nor ERK 1/2, were phosphorylated in response to attempted BCR ligation using a F(ab')$_2$ specific antibody after IdeS treatment. The mock treated cells responded normally. These data demonstrate that IdeS treated cells with a cleaved IgG-type of BCR cannot respond to antigenic stimulation.

IdeS Blocks B-Cell Maturation

Figure 28A:
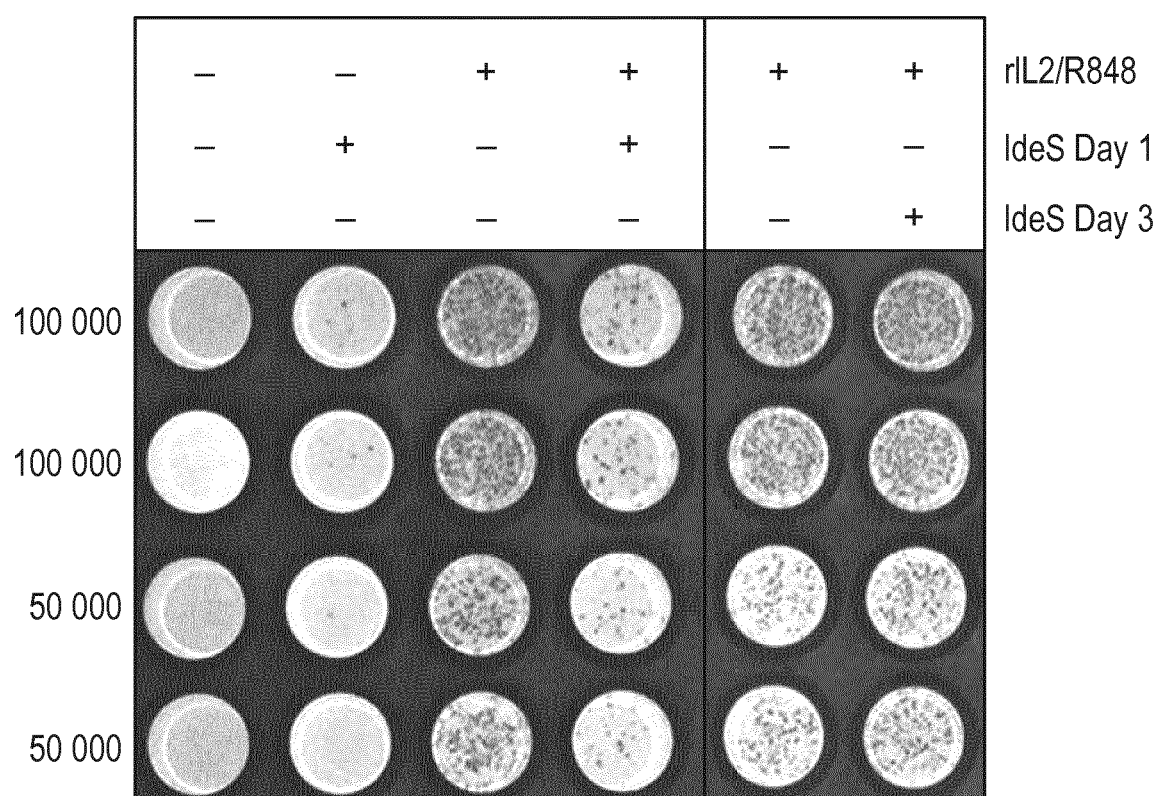
FIGS. 28A-28D show IdeS specifically blocks B-cell maturation of IgG-producing cells. PBMC's were treated with IdeS and stimulated with recombinant IL2 and R848 in order to activate memory B-cells and differentiate them into Ig-producing cells. ELISPOT filter plates were evaluated for number of IgG-producing cells.
Figure 28B:
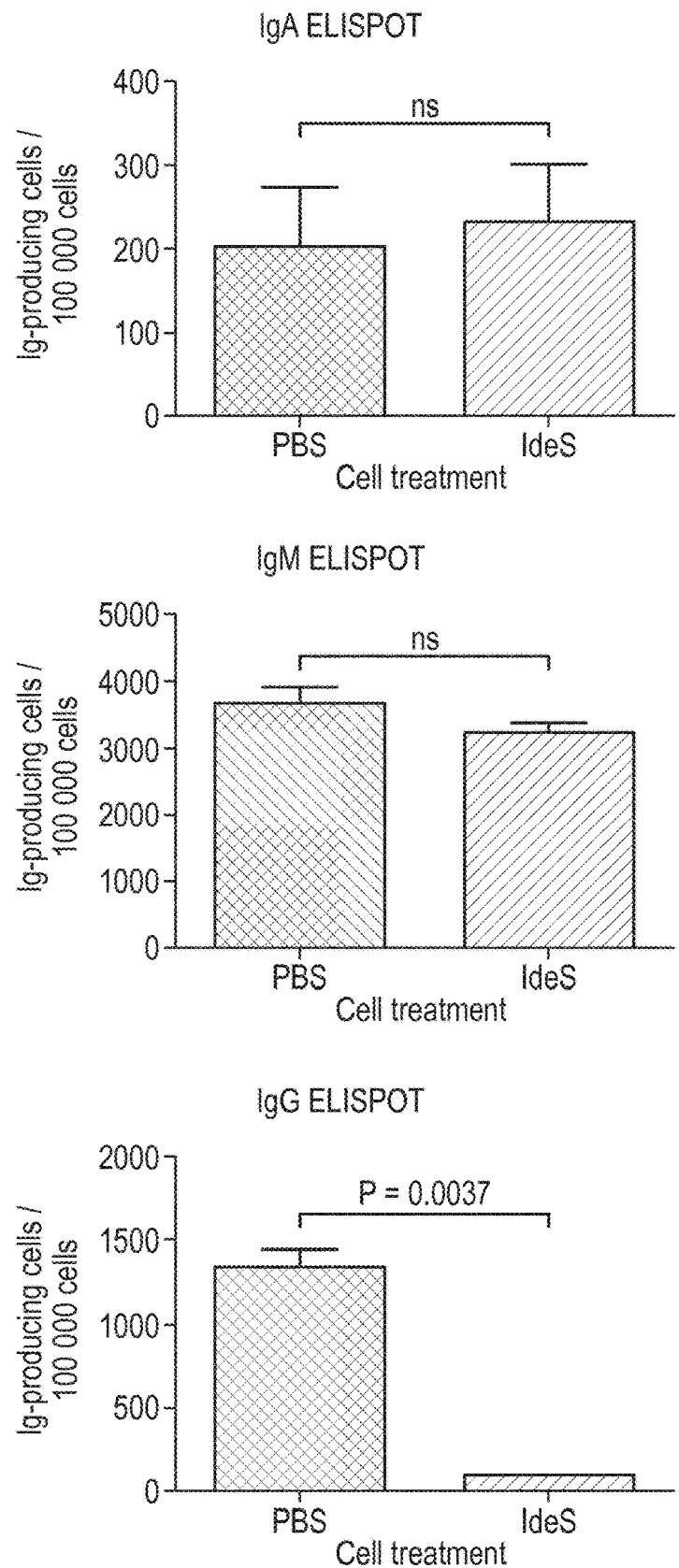
Figure 28C:
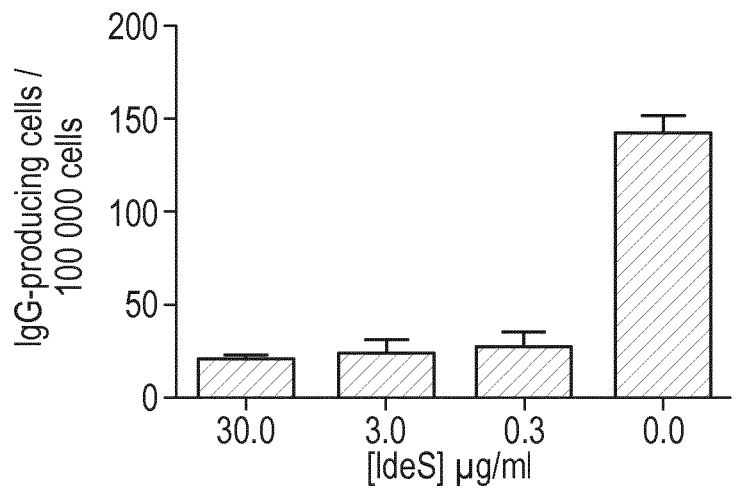
Figure 28D:
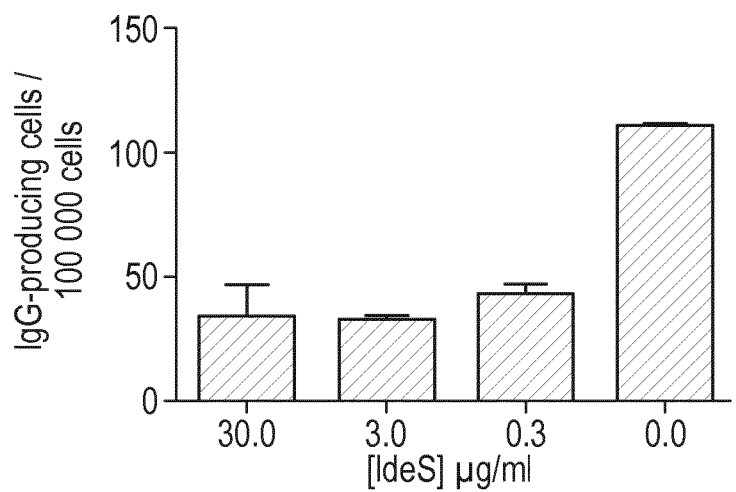

Due to the finding that IdeS does not affect the viability of cell lines or primary B-cells but renders them unable to respond to antigen, we decided to further explore the functionality of primary memory B-cells. Thus, PBMCs were collected, treated with IdeS and stimulated with recombinant IL2 and R848 in order to activate memory B-cells and differentiate them into Ig-producing cells (Jahnmatz et al., 2013). After 72-96 hours the cells were extensively washed in order to remove IdeS and analysed for frequency of Ig-producing cells. IdeS was also added on day three of IL2/R848 culture as additional control. At this time point it is not possible to stop the secretion of IgG of IL2/R848 differentiated B-cells. This control also shows that the loss of signal is not due to a carryover effect of IdeS interfering with the antibodies of the ELISPOT assay (FIG. 28A). In most experiments, IdeS was present throughout the stimulation period (96 hours) and the results showed that IdeS treatment inhibited memory B-cell differentiation and the number of IgG-producing cells while it had no effect on the maturation of IgM- or IgA-producing cells (FIGS. 28A and 28B). There was a significant effect on B-cell differentiation at all tested IdeS concentrations from 0.3 to 30 µg/ml (FIG. 28C). A second set of experiments where IdeS was washed away prior to stimulation with IL2 and R848 also resulted in a significant reduction in the number of IgG-producing cells (FIG. 28D) showing that the initial removal of the antigen-binding part of IgG-BCR is an important step in inhibiting memory B-cell activation into Ig-producing cells.

IdeS Cleaves the IgG-Type of BCR In Vivo in Humans

Figure 29:
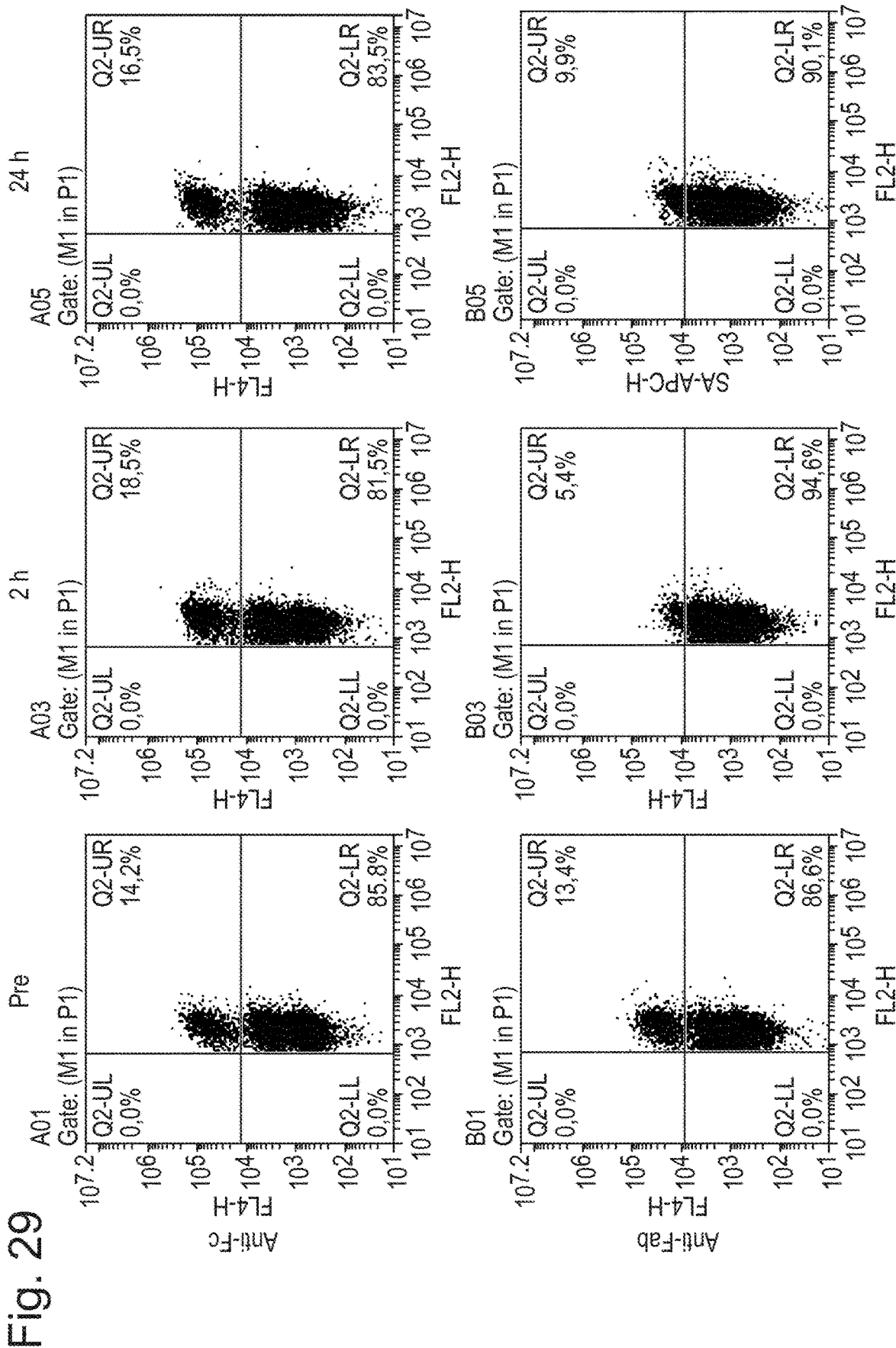
FIG. 29 shows Flow cytometry analysis of CD19$^+$/IgG$^+$ cells at different time points after IdeS treatment in a human healthy subject after a single i.v. dose of 0.24 mg/kg BW of IdeS. Purified PBMCs were gated using forward-side scatter (P1) and the B-cells (CD19$^+$) were monitored as M1n P1. The upper panel shows double positive cells for CD19 (FL2) and the Fc-part of IgG (FL4) pre-dose and up to 96 hours post dosing. The lower panel shows double positive cells for CD19 (FL2) and the Fab-part of IgG (FL4) pre-dose and up to 96 hours post dosing.
Figure 29:
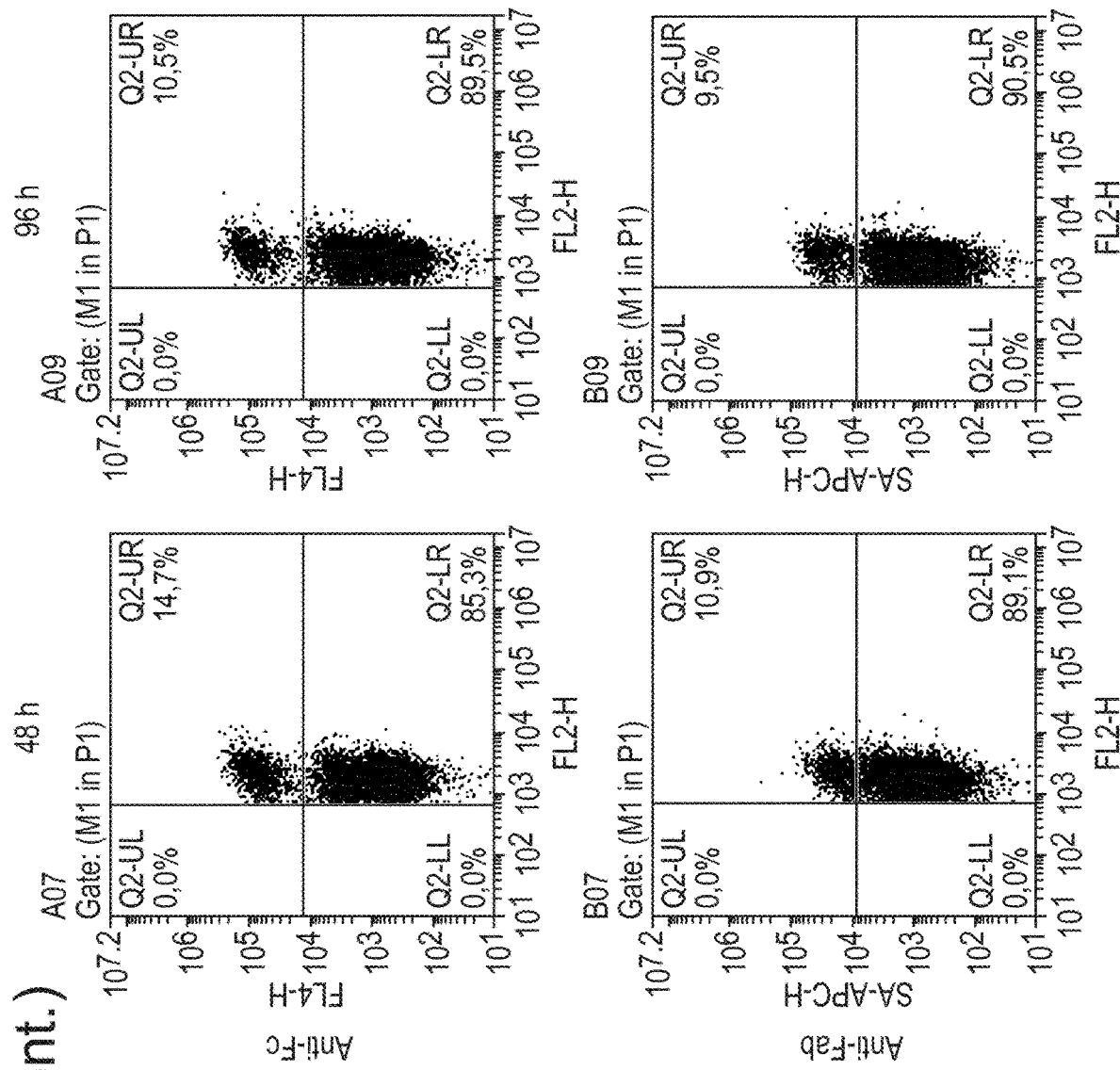
Figure 30:
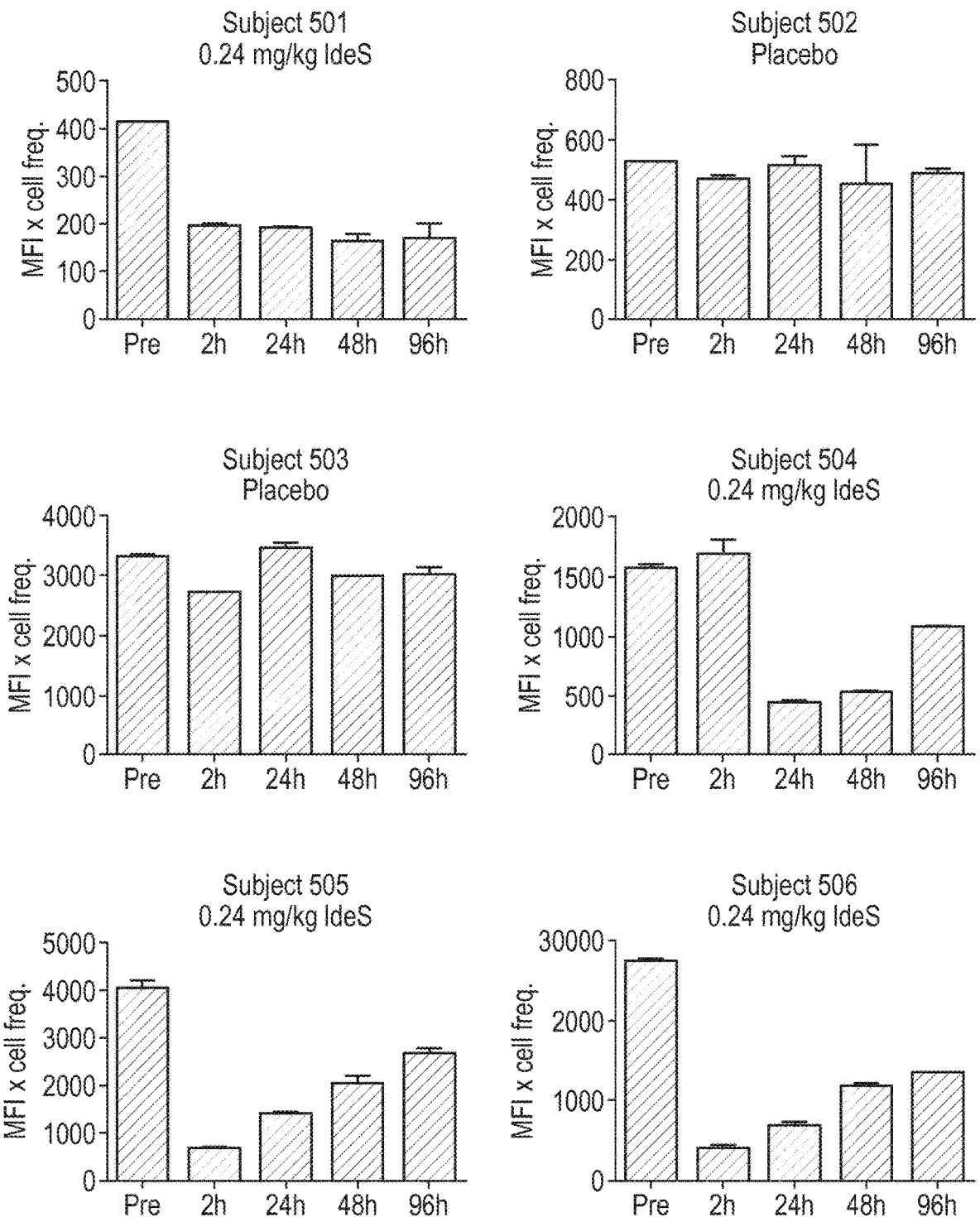
FIG. 30 shows IdeS cleaves the IgG-type of BCR in vivo in humans. Healthy human subjects were dosed with 0.24 mg/kg BW IdeS and PBMCs were collected at different time point after dosing. The percentage of double positive cells for CD19 and F(ab')$_2$ was analyzed using flow cytometry. Hours post-dosing is shown on the x-axis and MFI x cell frequency on the y-axis.

IdeS has recently been tested in a first in man study where healthy human subjects were given single ascending i.v. doses (ClinicalTrials.gov Identifier: NCT01802697) (submitted manuscript). The highest tested dose given to four subjects was 0.24 mg/kg BW. An exploratory part of the trial was to analyse the integrity of the IgG-type of BCR on circulating CD19+ lymphocytes at different time-points after IdeS administration. Peripheral blood was collected and PBMCs were purified at pre-dose, 2 h, 24 h, 48 h and 96 h post administration. Cells were immediately fixed to prevent further cell metabolism and stored until all time-points from a subject could be analysed. The PBMCs were double-stained for CD19 and F(ab')$_2$ respectively Fc-fragments and analysed using flow cytometry. The method can measure the frequency and mean fluorescence intensity of cells having F(ab')$_2$ (i.e. intact IgG-type of BCR) and Fc on their cell-surface. However, the method does not discriminate between intact and single-cleaved BCR. The results demonstrated that the number of CD19+ cells that stained positive for F(ab')$_2$ was reduced already 2 h after treatment with IdeS (0.24 mg/kg BW IdeS) while the number of cells that stained positive for Fc was not reduced (FIG. 29). This clearly demonstrates that IdeS in vivo cleaved the surface IgG on CD19+ cells. Data from the four subjects, plus two placebos demonstrate that IdeS efficiently cleaved the IgG-type of BCR in humans and that the frequency of CD19+ cells that were positive for surface IgG gradually recovered over the days following treatment (FIG. 30).

DISCUSSION

The data presented here clearly show that IdeS cleaves the IgG-type of BCR and completely inhibits BCR signalling in response to receptor ligation. Thus, B-cells with IdeS cleaved IgG-type of BCR are rendered incapable of antigen binding resulting in loss of the major cellular events downstream of receptor ligation i.e. internalization, processing and presentation on MHC class II molecules. B-cells are very potent antigen-presenting cells (Lanzavecchia 1990, Avalos & Plough 2015) and can with high efficiency present an antigen on HLA after specific BCR-mediated endocytosis, therefore the loss of the antigen-binding fragment of the BCR upon IdeS cleavage is likely to have an impact on antigen presentation to CD4+ T-cells.

Cleaving the IgG-type of BCR has no impact on cell viability neither on cell lines nor on B-cells purified from healthy human subjects (FIGS. 23, 24 and 26). However, cells seem to recover from the treatment slightly slower in vivo than in vitro (FIG. 30). Due to very limited amounts of cells available for analysis from the human phase 1 study, other B-cell markers could not be followed in this exploratory study. Hence, it is not possible to draw conclusions regarding the fate of any specific subpopulation of B-cells. The evidence is consistent with recovery of IgG-type of BCR on the cleaved cells by means of membrane turnover as we have seen in vitro, but it cannot be ruled out that the slight delay in recovery seen in vivo is due to maturation of new B-cells rather than mere membrane turnover.

The results presented here show that IdeS blocks development of IgG but not IgA or IgM antibody secreting cells if IdeS is used prior to activation with polyclonal stimulation (IL2 and R848). However, if IdeS is used later on it has no blocking effect. Upon in vitro stimulation of PBMCs in culture antigens bound to the BCR are internalized and loaded on MHCII molecules and presented to T-cells which induce B-cell proliferation and differentiation (Tangye & Tralington 2009). In the absence of antigen stimulation i.e. as in the case when the IgG-BCR is cleaved by IdeS, the B-cell will not get a second signal and proliferate.

Additionally, this indicates an important role for the IgG-BCR complex in responding to stimulation even in the absence of antigen, i.e. in maintaining tonic signal. It has been published that a single amino acid mutation in the extracellular region of CD79b of the BCR results in agammaglobulia (Dobbs et al., 2007). This finding indicates that the interaction between the proteins in the BCR on the extracellular part is important for cell activation and we speculate that the interaction between CD79a/b and the IgG is important for the generation of a proper signalosome in response to external stimuli. Further support for this theory comes from a publication targeting CD79b extracellular domain using a non-lytic antibody (Hardy et al., 2014). They found that binding to CD79b resulted in B-cell anergy and loss of IgG producing cells both in vitro and in vivo. We propose that disassembling the BCR by cleaving of the F(ab')$_2$ part of IgG results in unresponsiveness to antigen-dependent activation due to loss of proper intracellular protein assembling and generation of a functional signalosome.

IdeS is currently developed for desensitisation of highly sensitized patients on the waiting list for kidney transplantation. These patients have developed antibodies against most donors and there is little chance of finding a matching donor. By removing donor specific antibodies (DSA) using IdeS prior to transplantation patients can be made eligible for transplantation despite a positive cross-match before treatment. An additional effect of IdeS treatment is the instant generation of free F(ab')$_2$ fragments from DSA with retained binding capacity. These F(ab')$_2$ fragments may bind and block epitopes in the graft and since the F(ab')$_2$ fragments have lost their Fc-mediated functions such as complement fixation (CDC), antibody dependant cellular cytotoxicity (ADCC) and antibody dependant cellular phagocytosis (ADCP) the F(ab')$_2$ fragments may have the capacity to block out IgM and newly formed IgG DSA and thereby provide an additional protection of the graft. The results presented here show that IdeS also cleaves the IgG-type of BCR on CD27+ positive memory B-cells and renders them incapable of answering to antigenic stimulation. Thus, not only are DSA removed by IdeS, but furthermore, the DSA-specific memory B-cells are initially not capable of responding to donor antigens. This may potentially have long term effects on the outcome of graft survival as the initial activation of memory B-cells and generation of long-lived plasma cells is likely to be affected by IdeS treatment.

REFERENCES

Avalos A. M. & Ploegh H. (2014) Early BCR Events and Antigen Capture, Processing and Loading on MHC Class II on B cells. *Front. Immunol. March* 10:5:92

Dal Porto J M, Gauld S B, Merrell K T, Mills D, Pugh-Bernard A E, Cambier J. B cell antigen receptor signaling 101. *Mol. Immunol.* 41 (6-7), 599-613 (2004).

Dobbs A K, Yang T, Farmer D, Kager L, Parolini O, Conley M E. (2007) Cutting edge: a hypomorphic mutation in Igbeta (CD79b) in a patient with immunodeficiency and a leaky defect in B cell development. *J Immunol.* 15; 179(4):2055-9

Hardy I, Anceriz N, Rousseau F, Seefeldt M, Irla M et al. (2014) Anti-CD79 Antibody Induces B Cell Anergy That Protects against Autoimmunity. *J Immunol.* 192:1641-1650

Jahnmatz M, Kesa G, Netterlid E, Buisman A M, Thorstensson R, et al. (2013) Optimization of a human IgG B-cell ELISpot assay for the analysis of vaccine-induced B-cell responses. *J Immunol Methods* 391:50-59

Johansson B P, Shannon O, Björck L (2008) IdeS: a bacterial proteolytic enzyme with therapeutic potential. *PLoS One* 3: e1692

Johnson G L and Lapadat R. (2002). Mitogen-activated protein kinase pathways mediated by ERK, JNK, and p38 protein kinases. *Science,* 298, 1911-1912

Kurosaki T. Regulation of B-cell signal transduction by adaptor proteins. *Nat. Rev. Immunol.* 2 (5), 354-363 (2002)

Lanzavecchia A. Receptor-mediated antigen uptake and its effect on antigen presentation to class II-restricted T lymphocytes. *Annu Rev Immunol* (1990) 8:773-93

Manz R, Hauser A, Hiepe F, Radbruch A. (2005) Maintenance Of Serum Antibody Levels. *Annu. Rev. Immunol.* 2005. 23:367-86

Nandakumar K S, Johansson B P, Björck L, Holmdahl R (2007) Blocking of experimental arthritis by cleavage of IgG antibodies in vivo. *Arthritis Rheum* 56:3253-3260

Rajewsky K. Clonal selection and learning in the antibody system. *Nature* 1996: 381 (6585): 751-8

Reth M. Antigen receptor tail clue. *Nature* 338 (6214), 383-384 (1989)

Reth M, Wienands J. Initiation and processing of signals from the B cell antigen receptor. *Annu. Rev. Immunol.* 15, 453-479 (1997)

Scharenberg A M, Humphries L A, Rawlings D J. Calcium signalling and cell-fate choice in B cells. *Nat. Rev. Immunol.* 7 (10), 778-789 (2007)

Stuart G. Tangye and Kim L. Good Human IgM+CD27+ B Cells: Memory B Cells or "Memory" B Cells? *The Journal of Immunology,* 2007, 179:13-19

Su Y F, Chuang W J, Wang S M, Chen W Y, Chiang-Ni C, Lin Y S, Wu J J, Liu C C. (2011) The deficient cleavage of M protein-bound IgG by IdeS: insight into the escape of *Streptococcus pyogenes* from antibody-mediated immunity. *Mol Immunol.* 49 (1-2): 134-42

Tangye & Tralington. (2009) Memory B cells: Effectors of long-lived immune responses. *Eur. J. Immunol.* 39:2065-2075

Tradtrantip L, Asavapanumas N, Verkman A S (2013) Therapeutic cleavage of anti-aquaporin-4 autoantibody in neuromyelitis optica by an IgG-selective proteinase. *Mol Pharmacol* 83:1268-1275

Vincents B, von Pawel-Rammingen U, Björck L and Abrahamson M, (2004). Enzymatic characterization of the streptococcal endopeptidase, IdeS, reveals that it is a cysteine protease with strict specificity for IgG cleavage due to exosite binding. *Biochemistry* 43:15540-9 von Pawel-Rammingen U, Johansson B P and Björck L, (2002). IdeS, a novel streptococcal cysteine proteinase with unique specificity for immunoglobulin G. *EMBO J* 21:1607-15

Wenig K, Chatwell L, von Pawel-Rammingen U, Björck L, Huber R and Sondermann P, (2004). Structure of the streptococcal endopeptidase IdeS, a cysteine proteinase with strict specificity for IgG. *Proc Natl Acad Sci USA* 101:17371-6

Yang R, Otten M A, Hellmark T, Collin M, Björck L, et al. (2010) Successful treatment of experimental glomerulonephritis with IdeS and EndoS, IgG-degrading streptococcal enzymes. *Nephrol Dial Transplant* 25:2479-2486

EXAMPLE 4

The following study was conducted to determine whether it is possible to target the BCR of a B cell which has been treated with IdeS.

Materials and Methods

Briefly, two-step dilutions of cells (Nu-DUL-1, B-cell lymphoma with IgG-type of BCR; ACC 579 from DSMZ) from 80 000/well to 1250/well in R10 medium (RPMI1640, PEST and 10% FCS) were seeded in duplicates in a 96-well flat bottom polystyrene plate and used as a calibrator for viable cells. 20 000 cells/well were seeded in the plate and incubated with or without 30 µg/ml IdeS at 37° C. in the $CO_2$-incubator for 1 hour. Anti-Fab, Anti-Fc, or control was added to the test wells to a final conc. of 10 µg/ml and the plate was incubated at 37° C. in the $CO_2$-incubator. The first plate was removed after 3 hours, the second after 24 hours and the third after 48 hours. After removing the plate from the incubator, CCK-8 reagent (from CCK-8 cell counting kit; Dojindo Laboratories, Japan) was added and continued incubation for 1 hour prior to reading the plate at 450 nm in an ELISA-plate reader (spectrophotometer). The CCK-8 assay allows sensitive colorimetric assays for the determination of cell viability in cell proliferation and cytotoxicity assays. The anti-Fab agent used was F(ab')$_2$ specific goat F(ab')$_2$ fragment (Jackson #109-006-097, 1.3 mg/ml). The anti-Fc agent used was Fc specific goat F(ab')$_2$ fragment (Jackson #109-006-098, 1.3 mg/ml). The control was mouse gamma globulin (Jackson #015-000-002, 11.4 mg/ml). The control was selected to be from the same manufacturer as the tested anti-Fab and anti-Fc and because mouse IgG is not cleaved by IdeS.

| Results and conclusions | | | | | | | | | | |
|---|---|---|---|---|---|---|---|---|---|---|
| | Anti-Fab | | | Anti-FC | | | Ctrl IgG | | | |
| | 3 h | 24 h | 48 h | 3 h | 24 h | 48 h | 3 h | 24 h | 48 h | |
| PBS | 25665 | 18514 | 7969 | 21569 | 8568 | 3112 | 21569 | 23598 | 24386 | Mean no of |
| IdeS | 25026 | 29347 | 25211 | 23005 | 9104 | 979 | 21569 | 21583 | 22469 | viable cells |
| PBS | 1013 | 288 | 212 | 1015 | 332 | 446 | 884 | 504 | 1114 | StDEV |
| IdeS | 1718 | 664 | 355 | 1940 | 1780 | 427 | 1665 | 489 | 374 | |

The results show that cross-linking the BCR on a target cell expressing the IgG-type of BCR (in this case a B-cell lymphoma cell line) induces cell death using antibodies directed against either the F(ab')$_2$ or the Fc-part. Making direct use of the BCR as a target is however not possible in a human prior to IdeS treatment due to the presence of normal IgG-levels (~10 mg/mL) in circulation. However, pre-treatment with IdeS can decrease the antibody levels left in circulation while leaving an Fc-fragment on target cells still available for therapeutic intervention. Targeting the Fc-fragment after IdeS cleavage is at least as efficient on IdeS treated cells as on mock treated cells. Therapeutic intervention can be accomplished by means of an antibody targeting an epitope which is created in the BCR as a consequence of IdeS cleavage or even by targeting a common epitope on the Fc (as shown here). The therapeutic antibody is preferably one that is not cleaved by IdeS and has high degree of Fc-effector functions i.e. CDC, ADCC and ADCP. The antibody could also be coupled to a cytotoxic agent i.e. radioisotope or toxin.

Another possibility is provided by the considerably quicker recovery of intact IgG on membrane bound BCR compared to recovery of IgG in circulation. This makes it possible to use the F(ab')$_2$ part as target and not only the Fc-part. Recovery of the IgG-BCR on memory B-cells opens up the possibility to use antigens (linked to toxins or radioisotopes) to specifically target memory B-cells with particular non-desired specificities (i.e. anti-HLA or anti-insulin).

The invention claimed is:

1. A method for improving the benefit to a subject of a therapy or therapeutic agent, the method comprising (a) administering to the subject an agent which reduces Fc receptor binding of serum IgG molecules in the subject; and (b) subsequently administering said therapy or said therapeutic agent to the subject; wherein:

the amount of said agent administered is sufficient to eliminate Fc receptor binding by IgG molecules present in the serum of the subject; and steps (a) and (b) are separated by a time interval which is sufficient for Fc receptor binding by IgG molecules present in the serum of the subject to be eliminated;

wherein the agent is a protein having IgG cysteine protease activity from *Streptococcus pyogenes* which is IgG-degrading enzyme of *Streptococcus pyogenes* (IdeS), which agent comprises of the amino acid sequence of SEQ ID NO: 1, or a variant thereof comprising of an amino acid sequence having at least 90% sequence identity with SEQ ID NO: 1, which variant does not comprise deletions and any amino acid substitutions in the variant are conservative substitutions which conserve amino acid charge.

2. The method according to claim 1, wherein said agent is administered by intravenous infusion and/or the amount of said agent that is administered is between 0.01 mg/kg BW and 2 mg/kg BW, between 0.04 and 2 mg/kg BW, between 0.12 mg/kg BW and 2 mg/kg BW, between 0.24 mg/kg BW and 2 mg/kg BW, or between 1 mg/kg BW and 2 mg/kgBW.

3. The method according to claim 1 wherein:
the time interval comprises a lower and an upper limit, wherein:
the lower limit of the time interval between steps (a) and (b) is selected from: at least 30 minutes, at least 1 hour, at least 2 hours, at least 3 hours, at least 4 hours, at least 5 hours, or at least 6 hours; and
the upper limit of the time interval between steps (a) and (b) is independently selected from: at most 21 days, at most 18 days, at most 14 days, at most 13 days, at most 12 days, at most 11 days, at most 10 days, at most 9 days, at most 8 days, at most 7 days, at most 6 days, at most 5 days, at most 4 days, at most 3 days, at most 2 days, at most 24 hours, at most 18 hours, at most 12 hours, at most 10 hours, at most 8 hours, at most 7 hours or at most 6 hours.

4. The method according to claim 1, wherein the time interval between steps (a) and (b) is of 30 minutes to 1 hour, 30 minutes to 2 hours, 30 minutes to 3 hours, 30 minutes to 4 hours, 30 minutes to 5 hours, 30 minutes to 6 hours, 1 to 2 hours, 1 to 3 hours, 1 to 4 hours, 1 to 5 hours, 1 to 6 hours, 2 to 3 hours, 2 to 4 hours, 2 to 5 hours, 2 to 6 hours, 3 to 4 hours, 3 to 5 hours, 3 to 6 hours, 4 to 5 hours, 4 to 6 hours, or 5 to 6 hours.

5. The method according to claim 1, wherein said therapeutic agent is an antibody which is administered for the treatment of cancer or another disease, optionally wherein said cancer is breast cancer.

6. The method according to claim 1, wherein said therapeutic agent is Trastuzumab.

7. The method according to claim 1, wherein said therapy is an organ transplant.

8. The method according to claim 7, further comprising induction of T cell and/or B cell suppression in the subject concurrently or immediately prior to transplantation.

9. The method according to claim 8, wherein said induction suppression comprises administering an effective amount of at least one of Muromonab, Basiliximab, Daclizumab, an antithymocyte anti-thymocyte globulin (ATG) antibody, a lymphocyte immune globulin, anti-thymocyte globulin preparation (ATGAM), or Rituximab.

10. The method of claim 1, wherein the agent consists of the amino acid sequence of SEQ ID NO: 1, or a variant thereof consisting of an amino acid sequence having at least 90% sequence identity with SEQ ID NO: 1, which variant does not comprise deletions and any amino acid substitutions in the variant are conservative substitutions which conserve amino acid charge.

11. The method of claim 7, wherein the organ is kidney, liver, heart, pancreas, lung, or small intestine.

* * * * *

SEQUENCE LISTING

<160> NUMBER OF SEQ ID NOS: 7

<210> SEQ ID NO 1
<211> LENGTH: 310
<212> TYPE: PRT
<213> ORGANISM: Streptococcus pyogenes

<400> SEQUENCE: 1

```
Asp Ser Phe Ser Ala Asn Gln Glu Ile Arg Tyr Ser Glu Val Thr Pro
1               5                   10                  15

Tyr His Val Thr Ser Val Trp Thr Lys Gly Val Thr Pro Pro Ala Asn
                20                  25                  30

Phe Thr Gln Gly Glu Asp Val Phe His Ala Pro Tyr Val Ala Asn Gln
            35                  40                  45

Gly Trp Tyr Asp Ile Thr Lys Thr Phe Asn Gly Lys Asp Asp Leu Leu
        50                  55                  60

Cys Gly Ala Ala Thr Ala Gly Asn Met Leu His Trp Trp Phe Asp Gln
65                  70                  75                  80

Asn Lys Asp Gln Ile Lys Arg Tyr Leu Glu Glu His Pro Glu Lys Gln
                85                  90                  95

Lys Ile Asn Phe Asn Gly Glu Gln Met Phe Asp Val Lys Glu Ala Ile
            100                 105                 110

Asp Thr Lys Asn His Gln Leu Asp Ser Lys Leu Phe Glu Tyr Phe Lys
        115                 120                 125

Glu Lys Ala Phe Pro Tyr Leu Ser Thr Lys His Leu Gly Val Phe Pro
    130                 135                 140

Asp His Val Ile Asp Met Phe Ile Asn Gly Tyr Arg Leu Ser Leu Thr
145                 150                 155                 160

Asn His Gly Pro Thr Pro Val Lys Glu Gly Ser Lys Asp Pro Arg Gly
                165                 170                 175

Gly Ile Phe Asp Ala Val Phe Thr Arg Gly Asp Gln Ser Lys Leu Leu
            180                 185                 190

Thr Ser Arg His Asp Phe Lys Glu Lys Asn Leu Lys Glu Ile Ser Asp
        195                 200                 205

Leu Ile Lys Lys Glu Leu Thr Glu Gly Lys Ala Leu Gly Leu Ser His
    210                 215                 220

Thr Tyr Ala Asn Val Arg Ile Asn His Val Ile Asn Leu Trp Gly Ala
225                 230                 235                 240

Asp Phe Asp Ser Asn Gly Asn Leu Lys Ala Ile Tyr Val Thr Asp Ser
                245                 250                 255

Asp Ser Asn Ala Ser Ile Gly Met Lys Lys Tyr Phe Val Gly Val Asn
            260                 265                 270
```

Ser Ala Gly Lys Val Ala Ile Ser Ala Lys Glu Ile Lys Glu Asp Asn
         275                 280                 285

Ile Gly Ala Gln Val Leu Gly Leu Phe Thr Leu Ser Thr Gly Gln Asp
         290                 295                 300

Ser Trp Asn Gln Thr Asn
305                 310

<210> SEQ ID NO 2
<211> LENGTH: 959
<212> TYPE: PRT
<213> ORGANISM: Streptococcus pyogenes

<400> SEQUENCE: 2

Glu Glu Lys Thr Val Gln Val Gln Lys Gly Leu Pro Ser Ile Asp Ser
1               5                   10                  15

Leu His Tyr Leu Ser Glu Asn Ser Lys Lys Glu Phe Lys Glu Glu Leu
            20                  25                  30

Ser Lys Ala Gly Gln Glu Ser Gln Lys Val Lys Glu Ile Leu Ala Lys
        35                  40                  45

Ala Gln Gln Ala Asp Lys Gln Ala Gln Glu Leu Ala Lys Met Lys Ile
    50                  55                  60

Pro Glu Lys Ile Pro Met Lys Pro Leu His Gly Pro Leu Tyr Gly Gly
65                  70                  75                  80

Tyr Phe Arg Thr Trp His Asp Lys Thr Ser Asp Pro Thr Glu Lys Asp
                85                  90                  95

Lys Val Asn Ser Met Gly Glu Leu Pro Lys Glu Val Asp Leu Ala Phe
            100                 105                 110

Ile Phe His Asp Trp Thr Lys Asp Tyr Ser Leu Phe Trp Lys Glu Leu
        115                 120                 125

Ala Thr Lys His Val Pro Lys Leu Asn Lys Gln Gly Thr Arg Val Ile
    130                 135                 140

Arg Thr Ile Pro Trp Arg Phe Leu Ala Gly Gly Asp Asn Ser Gly Ile
145                 150                 155                 160

Ala Glu Asp Thr Ser Lys Tyr Pro Asn Thr Pro Glu Gly Asn Lys Ala
                165                 170                 175

Leu Ala Lys Ala Ile Val Asp Glu Tyr Val Tyr Lys Tyr Asn Leu Asp
            180                 185                 190

Gly Leu Asp Val Asp Val Glu His Asp Ser Ile Pro Lys Val Asp Lys
        195                 200                 205

Lys Glu Asp Thr Ala Gly Val Glu Arg Ser Ile Gln Val Phe Glu Glu
    210                 215                 220

Ile Gly Lys Leu Ile Gly Pro Lys Gly Val Asp Lys Ser Arg Leu Phe
225                 230                 235                 240

Ile Met Asp Ser Thr Tyr Met Ala Asp Lys Asn Pro Leu Ile Glu Arg
                245                 250                 255

Gly Ala Pro Tyr Ile Asn Leu Leu Leu Val Gln Val Tyr Gly Ser Gln
            260                 265                 270

Gly Glu Lys Gly Gly Trp Glu Pro Val Ser Asn Arg Pro Glu Lys Thr
        275                 280                 285

Met Glu Glu Arg Trp Gln Gly Tyr Ser Lys Tyr Ile Arg Pro Glu Gln
    290                 295                 300

Tyr Met Ile Gly Phe Ser Phe Tyr Glu Glu Asn Ala Gln Glu Gly Asn
305                 310                 315                 320

Leu Trp Tyr Asp Ile Asn Ser Arg Lys Asp Glu Asp Lys Ala Asn Gly

```
                    325                 330                 335
Ile Asn Thr Asp Ile Thr Gly Thr Arg Ala Glu Arg Tyr Ala Arg Trp
                340                 345                 350
Gln Pro Lys Thr Gly Gly Val Lys Gly Gly Ile Phe Ser Tyr Ala Ile
                355                 360                 365
Asp Arg Asp Gly Val Ala His Gln Pro Lys Lys Tyr Ala Lys Gln Lys
            370                 375                 380
Glu Phe Lys Asp Ala Thr Asp Asn Ile Phe His Ser Asp Tyr Ser Val
385                 390                 395                 400
Ser Lys Ala Leu Lys Thr Val Met Leu Lys Asp Lys Ser Tyr Asp Leu
                405                 410                 415
Ile Asp Glu Lys Asp Phe Pro Asp Lys Ala Leu Arg Glu Ala Val Met
                420                 425                 430
Ala Gln Val Gly Thr Arg Lys Gly Asp Leu Glu Arg Phe Asn Gly Thr
                435                 440                 445
Leu Arg Leu Asp Asn Pro Ala Ile Gln Ser Leu Glu Gly Leu Asn Lys
            450                 455                 460
Phe Lys Lys Leu Ala Gln Leu Asp Leu Ile Gly Leu Ser Arg Ile Thr
465                 470                 475                 480
Lys Leu Asp Arg Ser Val Leu Pro Ala Asn Met Lys Pro Gly Lys Asp
                485                 490                 495
Thr Leu Glu Thr Val Leu Glu Thr Tyr Lys Lys Asp Asn Lys Glu Glu
                500                 505                 510
Pro Ala Thr Ile Pro Pro Val Ser Leu Lys Val Ser Gly Leu Thr Gly
                515                 520                 525
Leu Lys Glu Leu Asp Leu Ser Gly Phe Asp Arg Glu Thr Leu Ala Gly
            530                 535                 540
Leu Asp Ala Ala Thr Leu Thr Ser Leu Glu Lys Val Asp Ile Ser Gly
545                 550                 555                 560
Asn Lys Leu Asp Leu Ala Pro Gly Thr Glu Asn Arg Gln Ile Phe Asp
                565                 570                 575
Thr Met Leu Ser Thr Ile Ser Asn His Val Gly Ser Asn Glu Gln Thr
                580                 585                 590
Val Lys Phe Asp Lys Gln Lys Pro Thr Gly His Tyr Pro Asp Thr Tyr
                595                 600                 605
Gly Lys Thr Ser Leu Arg Leu Pro Val Ala Asn Glu Lys Val Asp Leu
            610                 615                 620
Gln Ser Gln Leu Leu Phe Gly Thr Val Thr Asn Gln Gly Thr Leu Ile
625                 630                 635                 640
Asn Ser Glu Ala Asp Tyr Lys Ala Tyr Gln Asn His Lys Ile Ala Gly
                645                 650                 655
Arg Ser Phe Val Asp Ser Asn Tyr His Tyr Asn Phe Lys Val Ser
                660                 665                 670
Tyr Glu Asn Tyr Thr Val Lys Val Thr Asp Ser Thr Leu Gly Thr Thr
            675                 680                 685
Thr Asp Lys Thr Leu Ala Thr Asp Lys Glu Glu Thr Tyr Lys Val Asp
            690                 695                 700
Phe Phe Ser Pro Ala Asp Lys Thr Lys Ala Val His Thr Ala Lys Val
705                 710                 715                 720
Ile Val Gly Asp Glu Lys Thr Met Met Val Asn Leu Ala Glu Gly Ala
                725                 730                 735
Thr Val Ile Gly Gly Ser Ala Asp Pro Val Asn Ala Arg Lys Val Phe
            740                 745                 750
```

```
Asp Gly Gln Leu Gly Ser Glu Thr Asp Asn Ile Ser Leu Gly Trp Asp
            755                 760                 765

Ser Lys Gln Ser Ile Ile Phe Lys Leu Lys Glu Asp Gly Leu Ile Lys
    770                 775                 780

His Trp Arg Phe Phe Asn Asp Ser Ala Arg Asn Pro Glu Thr Thr Asn
785                 790                 795                 800

Lys Pro Ile Gln Glu Ala Ser Leu Gln Ile Phe Asn Ile Lys Asp Tyr
            805                 810                 815

Asn Leu Asp Asn Leu Leu Glu Asn Pro Asn Lys Phe Asp Asp Glu Lys
            820                 825                 830

Tyr Trp Ile Thr Val Asp Thr Tyr Ser Ala Gln Gly Glu Arg Ala Thr
            835                 840                 845

Ala Phe Ser Asn Thr Leu Asn Asn Ile Thr Ser Lys Tyr Trp Arg Val
            850                 855                 860

Val Phe Asp Thr Lys Gly Asp Arg Tyr Ser Ser Pro Val Val Pro Glu
865                 870                 875                 880

Leu Gln Ile Leu Gly Tyr Pro Leu Pro Asn Ala Asp Thr Ile Met Lys
            885                 890                 895

Thr Val Thr Thr Ala Lys Glu Leu Ser Gln Gln Lys Asp Lys Phe Ser
            900                 905                 910

Gln Lys Met Leu Asp Glu Leu Lys Ile Lys Glu Met Ala Leu Glu Thr
            915                 920                 925

Ser Leu Asn Ser Lys Ile Phe Asp Val Thr Ala Ile Asn Ala Asn Ala
            930                 935                 940

Gly Val Leu Lys Asp Cys Ile Glu Lys Arg Gln Leu Leu Lys Lys
945                 950                 955

<210> SEQ ID NO 3
<211> LENGTH: 312
<212> TYPE: PRT
<213> ORGANISM: Streptococcus pyogenes

<400> SEQUENCE: 3

Asp Ser Phe Ser Ala Asn Gln Glu Ile Arg Tyr Ser Glu Val Thr Pro
1               5                   10                  15

Tyr His Val Thr Ser Val Trp Thr Lys Gly Val Thr Pro Pro Ala Lys
            20                  25                  30

Phe Thr Gln Gly Glu Asp Val Phe His Ala Pro Tyr Val Ala Asn Gln
        35                  40                  45

Gly Trp Tyr Asp Ile Thr Lys Thr Phe Asn Gly Lys Asp Asp Leu Leu
    50                  55                  60

Cys Gly Ala Ala Thr Ala Gly Asn Met Leu His Trp Trp Phe Asp Gln
65                  70                  75                  80

Asn Asn Glu Lys Ile Glu Ala Tyr Leu Lys Lys His Pro Asp Lys Gln
                85                  90                  95

Lys Ile Met Phe Gly Asp Gln Glu Leu Leu Asp Val Arg Lys Val Ile
            100                 105                 110

Asn Thr Lys Gly Asp Gln Thr Asn Ser Glu Leu Phe Asn Tyr Phe Arg
        115                 120                 125

Asp Lys Ala Phe Pro Gly Leu Ser Ala Arg Arg Ile Gly Val Met Pro
    130                 135                 140

Asp Leu Val Leu Asp Met Phe Ile Asn Gly Tyr Tyr Leu Asn Val Tyr
145                 150                 155                 160

Lys Thr Gln Thr Thr Asp Val Asn Arg Thr Tyr Gln Glu Lys Asp Arg
```

```
                        165                 170                 175
Arg Gly Gly Ile Phe Asp Ala Val Phe Thr Arg Gly Asp Gln Ser Lys
                180                 185                 190

Leu Leu Thr Ser Arg His Asp Phe Lys Glu Lys Thr Leu Lys Glu Ile
            195                 200                 205

Ser Asp Leu Ile Lys Lys Glu Leu Thr Glu Gly Lys Ala Leu Gly Leu
    210                 215                 220

Ser His Thr Tyr Ala Asn Val Arg Ile Asn His Val Ile Asn Leu Trp
225                 230                 235                 240

Gly Ala Asp Phe Asp Ser Asn Gly Asn Leu Glu Ala Ile Tyr Val Thr
                245                 250                 255

Asp Ser Asp Ser Asn Ala Ser Ile Gly Met Lys Lys Tyr Phe Val Gly
                260                 265                 270

Val Asn Ser Ala Gly Lys Val Ala Ile Ser Ala Lys Glu Ile Lys Glu
                275                 280                 285

Asp Asn Ile Gly Ala Gln Val Leu Gly Leu Phe Thr Leu Ser Thr Gly
            290                 295                 300

Gln Asp Ser Trp Asn Gln Thr Asn
305                 310

<210> SEQ ID NO 4
<211> LENGTH: 6
<212> TYPE: PRT
<213> ORGANISM: Streptococcus pyogenes

<400> SEQUENCE: 4

Leu Phe Glu Tyr Phe Lys
1               5

<210> SEQ ID NO 5
<211> LENGTH: 8
<212> TYPE: PRT
<213> ORGANISM: Streptococcus pyogenes

<400> SEQUENCE: 5

Ala Phe Pro Tyr Leu Ser Thr Lys
1               5

<210> SEQ ID NO 6
<211> LENGTH: 16
<212> TYPE: PRT
<213> ORGANISM: Streptococcus pyogenes

<400> SEQUENCE: 6

Ala Ile Tyr Val Thr Asp Ser Asp Ser Asn Ala Ser Ile Gly Met Lys
1               5                   10                  15

<210> SEQ ID NO 7
<211> LENGTH: 10
<212> TYPE: PRT
<213> ORGANISM: Streptococcus pyogenes

<400> SEQUENCE: 7

Gly Gly Ile Phe Asp Ala Val Phe Thr Arg
1               5                   10
```